United States Patent
Filippova et al.

(10) Patent No.: US 11,929,148 B2
(45) Date of Patent: Mar. 12, 2024

(54) SYSTEMS AND METHODS FOR ENRICHING FOR CANCER-DERIVED FRAGMENTS USING FRAGMENT SIZE

(71) Applicant: GRAIL, LLC, Menlo Park, CA (US)

(72) Inventors: Darya Filippova, Sunnyvale, CA (US); Matthew H. Larson, San Francisco, CA (US); M. Cyrus Maher, San Mateo, CA (US); Monica Portela dos Santos Pimentel, San Jose, CA (US); Robert Abe Paine Calef, Redwood City, CA (US)

(73) Assignee: GRAIL, LLC, Menlo Park, CA (US)

( * ) Notice: Subject to any disclaimer, the term of this patent is extended or adjusted under 35 U.S.C. 154(b) by 715 days.

(21) Appl. No.: 16/816,918

(22) Filed: Mar. 12, 2020

(65) Prior Publication Data
US 2020/0294624 A1    Sep. 17, 2020

Related U.S. Application Data

(60) Provisional application No. 62/854,888, filed on May 30, 2019, provisional application No. 62/818,013, filed on Mar. 13, 2019.

(51) Int. Cl.
| | |
|---|---|
| *G16B 30/00* | (2019.01) |
| *C12Q 1/6886* | (2018.01) |
| *G06N 20/00* | (2019.01) |
| *G16B 20/10* | (2019.01) |
| *G16H 10/40* | (2018.01) |
| *G16H 10/60* | (2018.01) |
| *G16H 50/20* | (2018.01) |
| *G16H 50/50* | (2018.01) |
| *G16H 50/70* | (2018.01) |

(52) U.S. Cl.
CPC ........... *G16B 30/00* (2019.02); *C12Q 1/6886* (2013.01); *G06N 20/00* (2019.01); *G16B 20/10* (2019.02); *G16H 10/40* (2018.01); *G16H 10/60* (2018.01); *G16H 50/20* (2018.01); *G16H 50/50* (2018.01); *G16H 50/70* (2018.01); *C12Q 2600/112* (2013.01)

(58) Field of Classification Search
CPC ...... G16B 30/00; G16B 20/10; C12Q 1/6886; C12Q 2600/112; C12Q 2600/158; C12Q 1/6806; G06N 20/00; G06N 3/0454; G06N 5/003; G06N 7/005; G06N 20/10; G06N 20/20; G16H 10/40; G16H 10/60; G16H 50/20; G16H 50/50; G16H 50/70
See application file for complete search history.

(56) References Cited

U.S. PATENT DOCUMENTS

| | | | |
|---|---|---|---|
| 9,892,230 B2 | 2/2018 | Lo et al. | |
| 9,965,585 B2 | 5/2018 | Lo et al. | |
| 2015/0005176 A1 | 1/2015 | Kim et al. | |
| 2016/0201142 A1 | 7/2016 | Lo et al. | |
| 2017/0029900 A1* | 2/2017 | Lo | C12Q 1/6886 |
| 2017/0218450 A1 | 8/2017 | Lo et al. | |
| 2017/0240973 A1* | 8/2017 | Eltoukhy | C12Q 1/6809 |
| 2018/0087105 A1 | 3/2018 | Larson et al. | |
| 2018/0208999 A1* | 7/2018 | Lo | C12Q 1/6879 |
| 2019/0256924 A1* | 8/2019 | Vogelstein | C12Q 1/6858 |

FOREIGN PATENT DOCUMENTS

EP    3421613 A1    1/2019

OTHER PUBLICATIONS

U.S. Appl. No. 62/642,461 entitled "Method and system for selecting, managing and analyzing data of high dimensionality".
U.S. Appl. No. 62/777,693 entitled "Systems and Methods for Classifying Patients with Respect to Multiple Cancer Classes".
U.S. Appl. No. 62/679,347, filed Jun. 1, 2018.
Adalsteinsson, V.A et al., Nat. Commun., 8(1324) (2017).
Belie, J. et al., Clin. Chem., 61 :838-49 (2015).
Casadio et al., 2013, "Urine cell-free DNA integrity as a marker for early bladder cancer diagnosis: preliminary data," Urol Oncol. 2013;31(8): 1744-1750.
Chan et al., "Clinical Sciences Reviews Committee of the Association of Clinical Biochemists Cell-free nucleic acids in plasma, serum and urine: a new tool in molecular diagnosis," Ann Clin Biochem. 2003;40(Pt 2): 122-130.
Cook, "Use and Misuse of the Receiver Operating Characteristic Curve in Risk Prediction," Circulation 2007, 115: 928-935.
De Mattos-Arruda and Caldas, 2016, "Cell-free circulating tumour DNA as a liquid biopsy in breast cancer," Mol Oncol. 2016; 10(3):464-474.
Epub and Zhang et al., "Tumor markers CA19-9, CA242 and CEA in the diagnosis of pancreatic cancer: a metaanalysis," Int J Clin Exp Med. 2015;8(7):11683-11691.
Fernandes et al., 2017, "Transfer Learning with Partial Observability Applied to Cervical Cancer Screening," Pattern Recognition and Image Analysis: 8th Iberian Conference Proceedings, 243-250.

(Continued)

*Primary Examiner* — Jerry Lin
(74) *Attorney, Agent, or Firm* — Sheppard Mullin Richter & Hampton LLP

(57) ABSTRACT

Systems and methods for determining a cancer class of a subject are provided in which a plurality of sequence reads, in electronic form, are obtained from a biological sample of the subject. The sample comprises a plurality of cell-free DNA molecules including respective DNA molecules longer than a threshold length of less than 160 nucleotides. The plurality of sequence reads excludes sequence reads of cell-free DNA molecules in the plurality of cell-free DNA molecules longer than the threshold length. The plurality of sequence reads is used to identify a relative copy number at each respective genomic location in a plurality of genomic locations in the genome of the subject. The genetic information about the subject obtained from the sample and the genetic information consisting of the identification of the relative copy number at each respective genomic location, is applied to a classifier that determines the cancer class of the subject.

15 Claims, 54 Drawing Sheets

(56) References Cited

OTHER PUBLICATIONS

Frenel et al., 2015, Serial next-generation sequencing of circulating cell-free DNA evaluating tumor clone response to molecularly targeted drug administration. Clin Cancer Res. 21(20):4586-4596.
Goessl et al., "Fluorescent methylation-specific polymerase chain reaction for DNA-based detection of prostate cancer in bodily fluids," Cancer Res. 2000;60(21):5941-5945.
Hao et al., "Circulating cell-free DNA in serum as a biomarker for diagnosis and prognostic prediction of colorectal cancer," Br J Cancer. 2014; 111(8): 1482-1489.
Heitzer, E. et al., Genome Med. 5(30) (2013).
Heitzer et al., 2013, "Establishment of tumor-specific copy number alterations from plasma DNA of patients with cancer," Int J Cancer. 133(2):346-356.
Heitzer et al., 2015, "Circulating tumor DNA as a liquid biopsy for cancer," Clin Chem. 61(1):112-123.
Kim et al., 2014, "Circulating cell-free DNA as a promising biomarker in patients with gastric cancer: diagnostic validity and significant reduction of cfDNA after surgical resection," Ann Surg Treat Res. 2014;86(3): 136-142.
Lo et al., 2010, "Maternal plasma DNA sequencing reveals the genome-wide genetic and mutational profile of the fetus," Sci Transl Med. 2(61):61ra91.
Mouliere et al., Sci Transl Med., 10(466) (2018).
Murtaza, M. et al., Nature, 497: 108-12 (2013).
O'Marcaigh and Jacobson, 1993, "Estimating the Predictive Value of a Diagnostic Test, How to Prevent Misleading or Confusing Results," Clin. Ped. 32(8): 485-491.
Pepe et al., "Limitations of the Odds Ratio in Gauging the Performance of a Diagnostic, Prognostic, or Screening Marker," Am. J. Epidemiol 2004, 159 (9): 882-890.
Raptis and Menard, 1980, "Quantitation and characterization of plasma DNA in normals and patients with systemic lupus erythematosus," J Clin Invest. 66(6): 1391-1399.
Salvi et al., 2016, "Cell-free DNA as a diagnostic marker for cancer: current insights," Onco Targets Ther. 9:6549-6559.
Shao et al. 2015 "Quantitative analysis of cell-free DNA in ovarian cancer," Oncol Lett. 2015; 10(6):3478-3482.
Shapiro et al., 1983, "Determination of circulating DNA levels in patients with benign or malignant gastrointestinal disease," Cancer. 51(11):2116-2120.
Siegel et al., 2015, "Cancer statistics," CA Cancer J Clin. 65(1):5-29.
Sozzi et al., 2003 "Quantification of free circulating DNA as a diagnostic marker in lung cancer," J Clin Oncol. 21(21):3902-3908.
Stroun et al., "Neoplastic characteristics of the DNA found in the plasma of cancer patients," Oncology. 1989;46(5):318-322).
Terry et al., 2016, "A prospective evaluation of early detection biomarkers for ovarian cancer in the European EPIC cohort," Clin Cancer Res. Apr. 8, 2016.
Zonta et al., "Assessment of DNA integrity, applications for cancer research," Adv Clin Chem. 2015;70: 197-246.
International Search Report and Written Opinion dated Aug. 11, 2020, for International Patent Application No. PCT/US2020/022330.
Underhill, et al., "Fragment Length of Circulating Tumor DNA. PLoS Genetics", 2016, vol. 12, No. 7, e1006162, 24 pages.

* cited by examiner

2000

2001

Extract cfDNA sample
2002

↓

Ligate adaptor and prepare library
2004

↓

Pool ligated cfDNA from multiple subjects
2006

↓

In vitro size selection of the cfDNA
2008

↓

Generate sequence reads of the cfDNA
2010

↓

Process sequence reads to generate genetic data
2012

↓

Apply genetic data to classifier to determine cancer status
2016

3002 Obtain a first plurality of sequence reads, in electronic form, from a biological sample of the subject, where the biological sample includes a first plurality of cell-free DNA molecules including respective DNA molecules that are longer than a first threshold length, where the first threshold length is less than 160 nucleotides, and the first plurality of sequence reads excludes sequence reads of cell-free DNA molecules in the first plurality of cell-free DNA molecules longer than the first threshold length

3004 The subject is a human

3006 The subject has not been diagnosed as having cancer

3008 The biological sample includes blood, whole blood, plasma, serum, urine, cerebrospinal fluid, fecal material, saliva, sweat, tears, pleural fluid, pericardial fluid, or peritoneal fluid of the subject

3010 The biological sample is a blood sample

3012 The biological sample is a blood plasma sample

3014 The first threshold length is 150 nucleotides or less

3016 The first threshold length is 140 nucleotides or less

3018 The first threshold length is 130 nucleotides or less

3020 The first threshold length is between 140 nucleotides and 150 nucleotides

3022 The first threshold length is 140 nucleotides (B)

3024 The first plurality of sequence reads includes sequence reads of cell-free DNA molecules in the first plurality of cell-free DNA molecules having a length falling between a second threshold length and a third threshold length, where: the second threshold length is from 240 nucleotides to 260 nucleotides, and the third threshold length is from 290 nucleotides to 310 nucleotides 3026 The second threshold length is 250 nucleotides 3028 The third threshold length is 300 nucleotides 3030 The plurality of sequence reads is more than 5000 sequence reads 3032 The first plurality of sequence reads is obtained by:
generating a precursor plurality of sequence reads, in electronic form, for cell-free nucleic acid molecules in the biological sample, and
applying a length filter to the precursor plurality of sequence reads, thereby obtaining the first plurality of sequence reads 3034 The first plurality of sequence reads is obtained by:
separating cell-free DNA molecules in the biological sample that are no longer than the first threshold length from cell-free DNA molecules in the biological sample that are longer than the first threshold length, and
generating sequence reads from the separated cell-free DNA molecules that are no longer than the first threshold length, thereby obtaining the first plurality of sequence reads (C)

3036 Prior to the separating of the cell-free DNA molecules:
(i) adding a nucleic acid fragment having a fixed length of x nucleotides to the cell-free DNA molecules of the subject, where the nucleic acid fragment includes an identifier unique to the subject, and
(ii) after the adding (i), pooling the cell-free DNA molecules of the biological sample of the subject with cell-free DNA molecules from a plurality of other subjects, where the cell-free DNA molecules of each respective other subject in the plurality of other subjects comprise an added corresponding nucleic acid fragment having a fixed length of x nucleotides, where the added corresponding nucleic acid fragment includes an identifier unique to the respective other subject

3038 The fixed length x of the added nucleic acid fragment is from 100 nucleotides to 200 nucleotides

3040 The first plurality of sequence reads is generated by whole genome sequencing

3042 Use the first plurality of sequence reads to identify a relative copy number at each respective genomic location in a plurality of predetermined genomic locations in the genome of the subject, where the plurality of genomic locations comprises at least fifty genomic locations

3044 The subject is human and a genomic location in the plurality of genomic locations is a predetermined exon in a reference human genome

3046 The subject is human and each genomic location in the plurality of genomic locations is a bin in plurality of bins and where each bin in the plurality of bins represents a predetermined portion of a human reference genome (D)

3048 An average coverage rate of the plurality of sequence reads across the plurality of genomic locations is at least 3x

3050 An average coverage rate of the plurality of sequence reads across the plurality of genomic locations is at least 5x

3052 An average coverage rate of the plurality of sequence reads across the plurality of genomic locations is at least 10x

3054 The plurality of predetermined genomic locations are selected from a precursor set of genomic regions by a method comprising removing respective genomic locations in the precursor set having a variance that exceeds a threshold variance in relative copy number within a training set of electronic sequence reads

3056 Classify the subject, where the classifying includes applying genetic information about the subject obtained from the biological sample, where the genetic information is the identification of the relative copy number at each respective genomic location, to a classifier, thereby determining the cancer class of the subject

3058 Determining the cancer class of the subject includes determining whether or not the subject has cancer

3060 Determining the cancer class of the subject includes determining a stage of a cancer in the subject

3062 The stage of the cancer is a stage of a breast cancer, a stage of a lung cancer, a stage of a prostate cancer, a stage of a colorectal cancer, a stage of a renal cancer, a stage of a uterine cancer, a stage of a pancreatic cancer, a stage of a cancer of the esophagus, a stage of a lymphoma, a stage of a head/neck cancer, a stage of an ovarian cancer, a stage of a hepatobiliary cancer, a stage of a melanoma, a stage of a cervical cancer, a stage of a multiple myeloma, a stage of a leukemia, a stage of a thyroid cancer, a stage of a bladder cancer, or a stage of a gastric cancer (E)

3064 Determining the cancer class of the subject includes determining a type of a cancer present in the subject 3066 The type of cancer is breast cancer, lung cancer, prostate cancer, colorectal cancer, renal cancer, uterine cancer, pancreatic cancer, cancer of the esophagus, a lymphoma, head/neck cancer, ovarian cancer, a hepatobiliary cancer, a melanoma, cervical cancer, multiple myeloma, leukemia, thyroid cancer, bladder cancer, or gastric cancer 3068 Determining the cancer class of the subject includes determining a prognosis for a cancer in the subject 3070 The classifier is a multinomial classifier that provides a plurality of likelihoods responsive to the identification of the relative copy number at each respective genomic location, where each respective likelihood in the plurality of likelihoods is a likelihood that the test subject has a corresponding cancer class in a plurality of cancer classes 3072 The classifier is a multivariate logistic regression algorithm, a neural network algorithm, or a convolutional neural network algorithm 3074 The classifier is a neural network algorithm, a support vector machine algorithm, a Naive Bayes algorithm, a nearest neighbor algorithm, a boosted trees algorithm, a random forest algorithm, a convolutional neural network algorithm, a decision tree algorithm, a regression algorithm, or a clustering algorithm

3076 The classifier uses a linear or non-linear combination of the relative copy number at two or more respective genomic locations in the plurality of genomic locations 3078 Identifying the linear or non-linear combination of the relative copy number at two or more respective genomic locations by subjecting the relative copy number at each respective genomic position in the precursor set across a training set of electronic sequence reads to a dimension reduction technique 3080 The dimension reduction algorithm is a linear dimension reduction algorithm or a non-linear dimension reduction algorithm 3082 The dimension reduction algorithm is a linear dimension reduction algorithm selected from the group consisting of a principal component analysis algorithm and a factor analysis algorithm 3084 The dimension reduction algorithm is a non-linear dimension reduction algorithm selected from the group consisting of Sammon mapping, curvilinear components analysis, a stochastic neighbor embedding (SNE) algorithm, an Isomap algorithm, a maximum variance unfolding algorithm, a locally linear embedding algorithm, and a t-SNE algorithm 3086 The dimension reduction algorithm is a non-negative matrix factorization algorithm, a kernel principal component analysis algorithm, a graph-based kernel principal component analysis algorithm, a linear discriminant analysis algorithm, or a generalized discriminant analysis algorithm 3088 The dimension reduction algorithm is uniform manifold approximation and projection (UMAP) algorithm, a LargeVis algorithm, a Laplacian Eigenmap algorithm, or a Fisher's linear discriminant analysis algorithm (G)

3090 The classifying further includes applying the identity of an allele at a locus in the genome of the subject to the classifier 3092 The classifying further includes applying a methylation state at a locus in the genome of the subject to the classifier 3094 The cancer class of the subject is determined with a first degree of confidence.
The first degree of confidence is greater than a second degree of confidence obtainable by application of genetic information consisting of relative copy number at each respective genomic location in the plurality of genomic locations obtained from a second plurality of sequence reads from the biological sample, to the classifier.
The second plurality of sequence reads encodes (i) cell-free DNA molecules that are shorter than the first threshold length and (ii) cell-free DNA molecules that are longer than the first threshold length 3096 Obtaining the second plurality of sequence reads from the biological sample, using the second plurality of sequence reads to identify a relative copy number at each respective genomic location in the plurality of genomic locations in the genome of the subject.
Classifying the subject, where the classifying includes applying genetic information about the subject obtained from the biological sample, where the genetic information is the relative copy number at each respective genomic location in the plurality of genomic locations obtained from a second plurality of sequence reads from the biological sample, to the classifier, thereby determining the cancer class of the subject with the second confidence

4002 Obtain a respective plurality of cell-free DNA molecules from each corresponding biological sample in a plurality of biological samples, where each corresponding biological sample in the plurality of biological samples is from a different subject in a plurality of subjects of a single species, thereby forming a set of pluralities of cell-free DNA molecules 4004 Each biological sample in the plurality of biological sample includes blood, whole blood, plasma, serum, urine, cerebrospinal fluid, fecal material, saliva, sweat, tears, pleural fluid, pericardial fluid, or peritoneal fluid of the corresponding subject 4006 Each biological sample in the plurality of biological sample is a blood sample 4008 Each biological sample in the plurality of biological sample is a blood plasma sample 4010 Each subject in the plurality of subjects is human 4012 One or more respective subject in the plurality of subjects has not been diagnosed as having cancer 4014 Add, for each respective subject in the plurality of subjects, a nucleic acid fragment having a fixed length of x nucleotides to the cell-free DNA molecules of the respective subject, where the nucleic acid fragment includes an identifier unique to the respective subject 4016 The fixed length x of the added nucleic acid fragment is from 100 nucleotides to 200 nucleotides 4018 Pool cell-free DNA molecules from each respective subject in the plurality of subjects, thereby forming a pool of cell-free DNA molecules (B)

Fig. 4A

4020 Isolate cell-free DNA molecules in the pool of cell-free DNA molecules having a length that is no longer than a first threshold length, where the first threshold length is less than 160 + x, thereby forming a length-selected pool of cell-free DNA molecules

4022 The first threshold length is 150 + x nucleotides or less

4024 The first threshold length is 140 + x nucleotides or less

4026 The first threshold length is 130 + x nucleotides or less

4028 The first threshold length is from 140 + x nucleotides to 150 + x nucleotides

4030 The first threshold length is 140 + x nucleotides

4032 Isolating cell-free DNA molecules having a length falling between a second threshold length and a third threshold length, where:
the second threshold length is from 240 + x nucleotides to 260 + x nucleotides, and
the third threshold length is from 290 + x nucleotides to 310 + x nucleotides

4034 The second threshold length is 250 + x nucleotides

4036 The third threshold length is 300 + x nucleotides

4038 Sequence cell-free DNA molecules in the length-selected pool of cell-free DNA molecules, thereby generating a plurality of sequence reads in electronic form

4040 The plurality of sequence reads is more than 5000 sequence reads

Fig. 4B

4042 Determine the relative copy number at each respective genomic location in a plurality of predetermined genomic locations of the cell-free DNA molecules in the length-selected pool of cell-free DNA molecules

4044 The plurality of predetermined genomic locations includes at least fifty genomic locations

4046 The subject is human and a genomic location in the plurality of genomic locations is a predetermined exon in a reference human genome

4048 The subject is human and each genomic location in the plurality of genomic locations is a bin in plurality of bins and wherein each bin in the plurality of bins represents a predetermined portion of a human reference genome

4050 An average coverage rate of the plurality of sequence reads across the plurality of genomic locations is at least 3x

4052 An average coverage rate of the plurality of sequence reads across the plurality of genomic locations is at least 5x

4054 An average coverage rate of the plurality of sequence reads across the plurality of genomic locations is at least 10x

4056 The plurality of predetermined genomic locations are selected from a precursor set of genomic regions by a method including removing respective genomic locations in the precursor set having a variance that exceeds a threshold variance in relative copy number within a training set of electronic sequence reads

4058 Classify the cancer class of each respective subject in the plurality of subjects by applying genetic information about the subject obtained from the biological sample from the respective subject, where the genetic information is the analyzed relative copy number at each respective genomic location, to a classifier

4060 Classifying the cancer class of each respective subject includes determining whether or not the respective subject has cancer

4062 Classifying the cancer class of each respective subject includes determining a stage of a cancer in the respective subject

4064 The stage of the cancer is a stage of a breast cancer, a stage of a lung cancer, a stage of a prostate cancer, a stage of a colorectal cancer, a stage of a renal cancer, a stage of a uterine cancer, a stage of a pancreatic cancer, a stage of a cancer of the esophagus, a stage of a lymphoma, a stage of a head/neck cancer, a stage of an ovarian cancer, a stage of a hepatobiliary cancer, a stage of a melanoma, a stage of a cervical cancer, a stage of a multiple myeloma, a stage of a leukemia, a stage of a thyroid cancer, a stage of a bladder cancer, or a stage of a gastric cancer

4066 Classifying the cancer class of each respective subject includes determining a type of a cancer present in the respective subject

4068 The type of cancer is breast cancer, lung cancer, prostate cancer, colorectal cancer, renal cancer, uterine cancer, pancreatic cancer, cancer of the esophagus, a lymphoma, head/neck cancer, ovarian cancer, a hepatobiliary cancer, a melanoma, cervical cancer, multiple myeloma, leukemia, thyroid cancer, bladder cancer, or gastric cancer

4070 Classifying the cancer class of each respective subject includes determining a prognosis for a cancer in the respective subject

4072 The classifier is a multinomial classifier that provides a plurality of likelihoods responsive to the identification of the relative copy number at each respective genomic location, where each respective likelihood in the plurality of likelihoods is a likelihood that the test subject has a corresponding cancer class in a plurality of cancer classes

4074 The classifier is multivariate logistic regression algorithm, a neural network algorithm, or a convolutional neural network algorithm

4076 The classifier is a neural network algorithm, a support vector machine algorithm, a Naive Bayes algorithm, a nearest neighbor algorithm, a boosted trees algorithm, a random forest algorithm, a convolutional neural network algorithm, a decision tree algorithm, a regression algorithm, or a clustering algorithm (E)

4078 The classifier uses a linear or non-linear combination of the relative copy number at two or more respective genomic locations in the plurality of genomic locations

4080 Identifying the linear or non-linear combination of the relative copy number at two or more respective genomic locations by subjecting the relative copy number at each respective genomic position in the precursor set across a training set of electronic sequence reads to a dimension reduction technique

4082 The dimension reduction algorithm is a linear dimension reduction algorithm or a non-linear dimension reduction algorithm

4084 The dimension reduction algorithm is a linear dimension reduction algorithm selected from the group consisting of a principal component analysis algorithm and a factor analysis algorithm

4086 The dimension reduction algorithm is a non-linear dimension reduction algorithm selected from the group consisting of Sammon mapping, curvilinear components analysis, a stochastic neighbor embedding (SNE) algorithm, an Isomap algorithm, a maximum variance unfolding algorithm, a locally linear embedding algorithm, and a t-SNE algorithm

4088 The dimension reduction algorithm is a non-negative matrix factorization algorithm, a kernel principal component analysis algorithm, a graph-based kernel principal component analysis algorithm, a linear discriminant analysis algorithm, or a generalized discriminant analysis algorithm

4090 The dimension reduction algorithm is uniform manifold approximation and projection (UMAP) algorithm, a LargeVis algorithm, a Laplacian Eigenmap algorithm, or a Fisher's linear discriminant analysis algorithm (F)

4092 The classifying further includes applying the identity of an allele at a locus in the genome of the subject to the classifier 4094 The classifying further includes applying a methylation state at a locus in the genome of the subject to the classifier 4096 The cancer class of the subject is determined with a first degree of confidence.
The first degree of confidence is greater than a second degree of confidence obtainable by application of genetic information consisting of relative copy number at each respective genomic location in the plurality of genomic locations obtained from a second plurality of sequence reads from the biological sample, to the classifier.
The second plurality of sequence reads encodes (i) cell-free DNA molecules that are shorter than the first threshold length and (ii) cell-free DNA molecules that are longer than the first threshold length 4098 Obtaining the second plurality of sequence reads from the biological sample, using the second plurality of sequence reads to identify a relative copy number at each respective genomic location in the plurality of genomic locations in the genome of the subject.
Classifying the subject, where the classifying includes applying genetic information about the subject obtained from the biological sample, where the genetic information is the relative copy number at each respective genomic location in the plurality of genomic locations obtained from a second plurality of sequence reads from the biological sample, to the classifier, thereby determining the cancer class of the subject with the second confidence

Fig. 4F

| Size select vs | Subsample | Full depth | Subsample | Full Depth | Subsample | Full depth | Subsample | Full depth | Subsample | Full depth |
|---|---|---|---|---|---|---|---|---|---|---|
| Stage | 0 | | I | | II | | III | | IV | |
| p-value | 0.08 | 0.01 | 0.24 | 0.85 | 2e-6 | 0.06 | 3e-7 | 8e-3 | 3e-4 | 0.5 |
| mean change (2.5%, 97.5% CI) | 0.036 (-0.005, 0.072) | 0.044 (0.010, 0.079) | 0.014 (-0.010, 0.039) | 0.002 (-0.024, 0.028) | 0.086 (0.055, 0.118) | 0.026 (-0.001, 0.055) | 0.105 (0.071, 0.141) | 0.035 (0.009, 0.061) | 0.047 (0.023, 0.071) | 0.006 (-0.012, 0.024) | sens@ 95% spec

| Size select vs | Subsample | Full depth | Subsample | Full Depth | Subsample | Full depth | Subsample | Full depth | Subsample | Full depth |
|---|---|---|---|---|---|---|---|---|---|---|
| Stage | 0 | | I | | II | | III | | IV | |
| p-value | 0.08 | 0.07 | 0.04 | 0.48 | 6e-6 | 7e-3 | 4e-8 | 6e-3 | 2e-5 | 4e-3 |
| mean change (2.5%, 97.5% CI) | 0.025 (-0.003, 0.052) | 0.025 (-0.003, 0.052) | 0.015 (0.000, 0.027) | 0.005 (-0.009, 0.018) | 0.063 (0.038, 0.087) | 0.031 (0.009, 0.053) | 0.123 (0.086, 0.160) | 0.059 (0.017, 0.099) | 0.061 (0.035, 0.087) | 0.030 (0.010, 0.051) | sens@ 99% spec

Fig. 8E sens@ 95% spec

| Size select vs | Subsample | Full depth | Subsample | Full Depth | Subsample | Full depth | Subsample | Full depth | Subsample | Full depth |
|---|---|---|---|---|---|---|---|---|---|---|
| Stage | 0 | 0 | I | I | II | II | III | III | IV | IV |
| p-value | 0.34 | 0.01 | 0.15 | 0.82 | 3e-6 | 2e-3 | 1e-7 | 2e-3 | 8e-4 | 0.51 |
| mean change (2.5%, 97.5% CI) | 0.021 (-0.023, 0.065) | 0.044 (0.010, 0.079) | 0.028 (-0.010, 0.066) | 0.005 (-0.039, 0.049) | 0.144 (0.091, 0.198) | 0.070 (0.028, 0.112) | 0.115 (0.079, 0.151) | 0.043 (0.017, 0.069) | 0.047 (0.021, 0.074) | 0.006 (-0.013, 0.025) | sens@ 99% spec

| Size select vs | Subsample | Full depth | Subsample | Full Depth | Subsample | Full depth | Subsample | Full depth | Subsample | Full depth |
|---|---|---|---|---|---|---|---|---|---|---|
| Stage | 0 | 0 | I | I | II | II | III | III | IV | IV |
| p-value | 0.05 | 0.05 | 0.02 | 0.26 | 2e-5 | 2e-4 | 5e-10 | 4e-4 | 3e-5 | 2e-4 |
| mean change (2.5%, 97.5% CI) | 0.029 (0.001, 0.059) | 0.029 (0.001, 0.059) | 0.035 (0.005, 0.065) | 0.019 (-0.014, 0.052) | 0.121 (0.070, 0.171) | 0.085 (0.042, 0.128) | 0.142 (0.107, 0.178) | 0.075 (0.036, 0.114) | 0.070 (0.040, 0.100) | 0.040 (0.020, 0.059) |

Fig. 8H

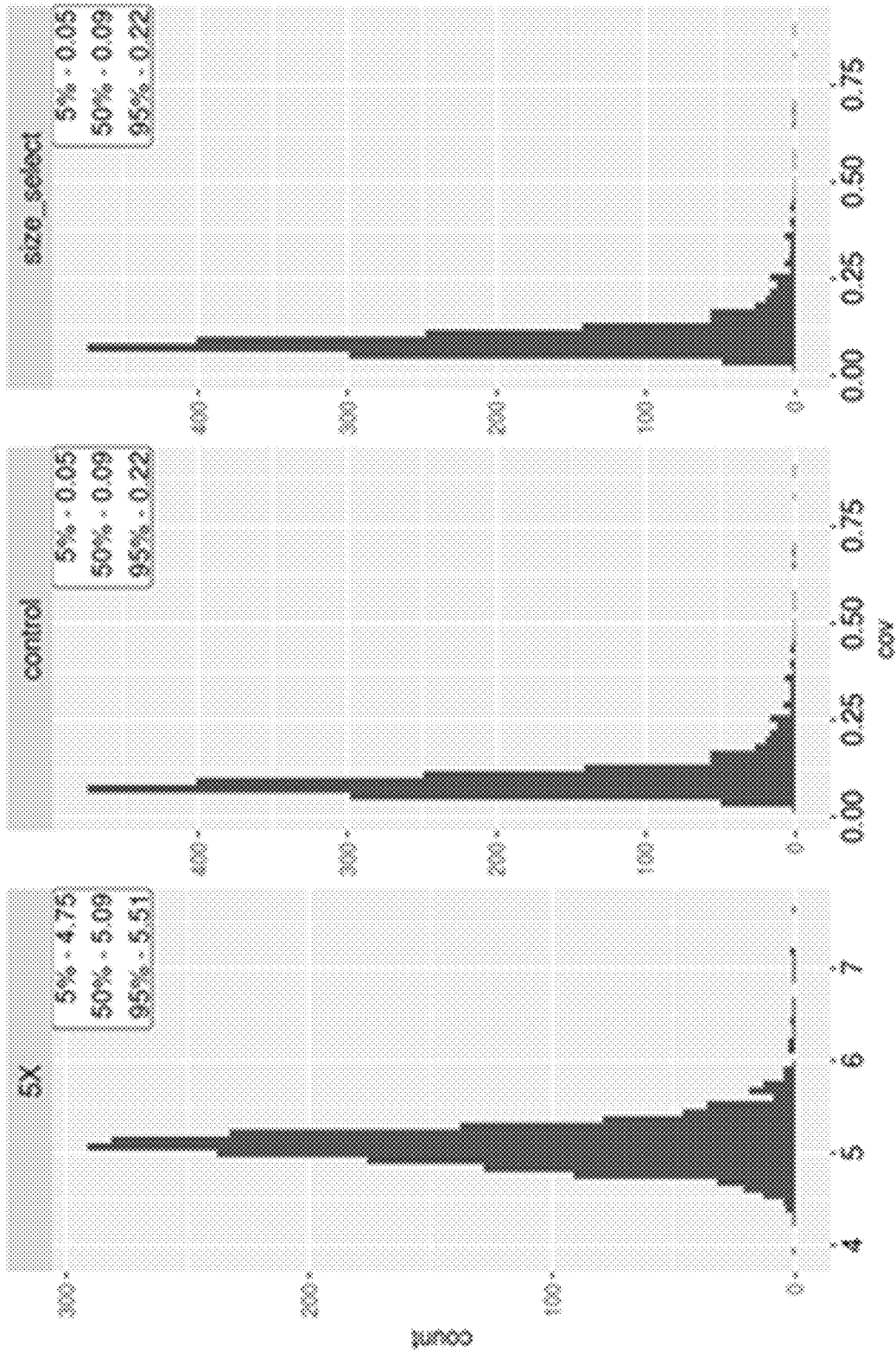

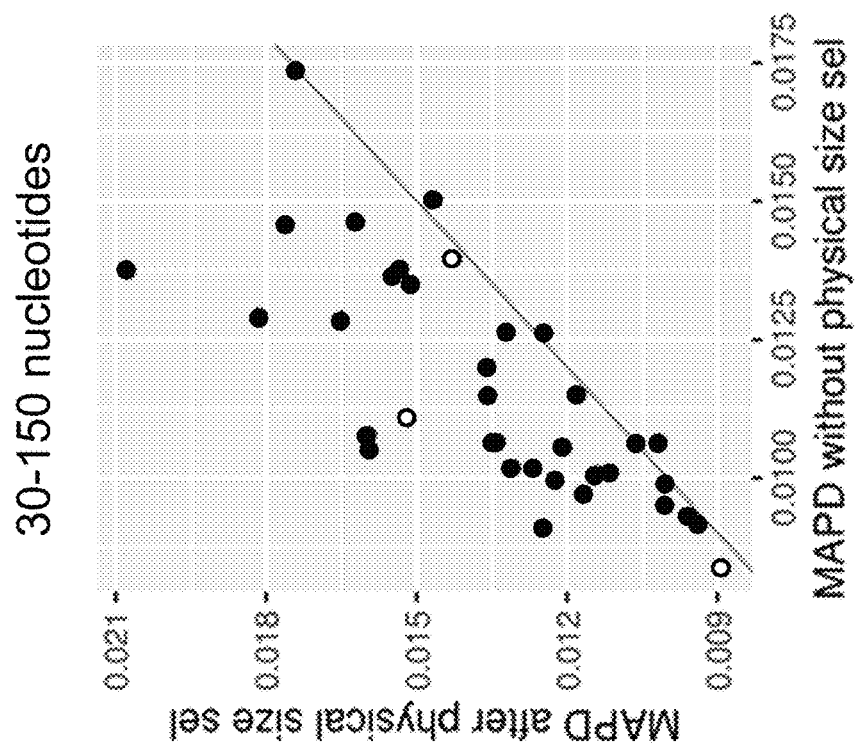
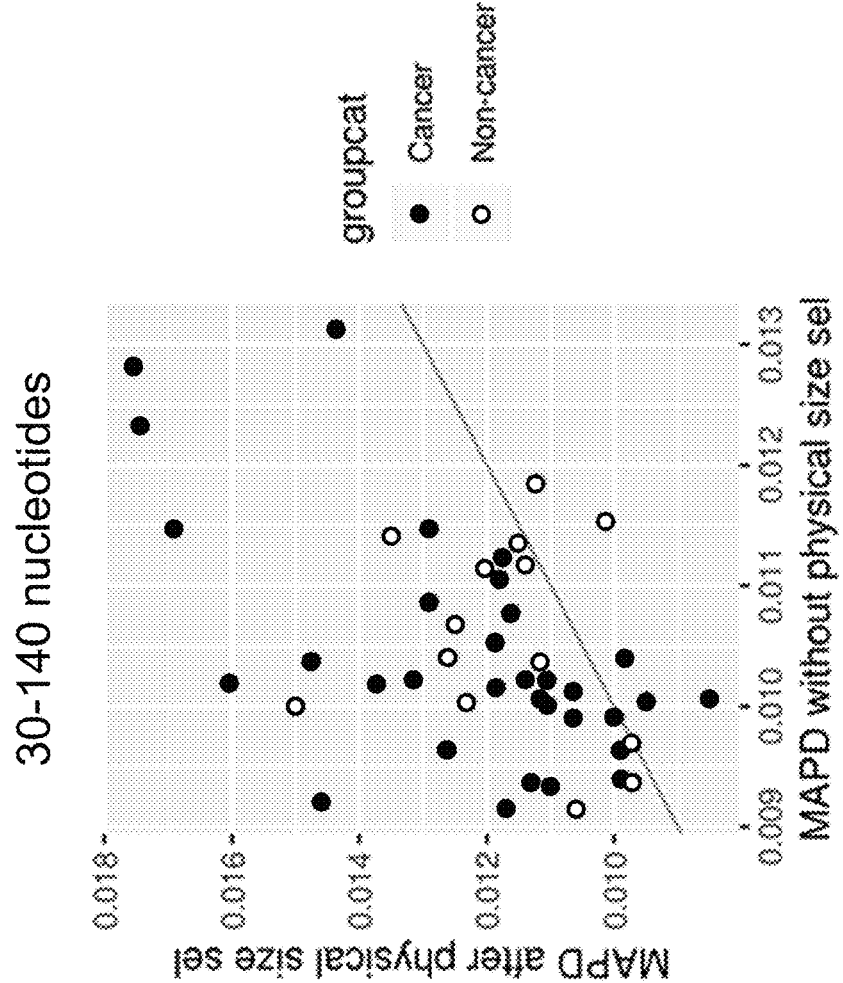
Fig. 22

SYSTEMS AND METHODS FOR ENRICHING FOR CANCER-DERIVED FRAGMENTS USING FRAGMENT SIZE

CROSS REFERENCE TO RELATED APPLICATIONS

This application claims priority to U.S. Provisional Patent Application No. 62/818,013, filed Mar. 13, 2019, and U.S. Provisional Patent Application No. 62/854,888, filed May 30, 2019, the contents of which are hereby incorporated by reference in their entireties for all purposes.

TECHNICAL FIELD

The present disclosure relates generally to using cell-free DNA sequencing data to classify a cancer state or condition of a subject.

BACKGROUND

The increasing knowledge of the molecular pathogenesis of cancer and the rapid development of next generation sequencing techniques are advancing the study of early molecular alterations involved in cancer development in body fluids. Specific genetic and epigenetic alterations associated with such cancer development are found in cell-free DNA (cfDNA) in plasma, serum, and urine. Such alterations could potentially be used as diagnostic biomarkers for several types of cancers. See Salvi et al., 2016, "Cell-free DNA as a diagnostic marker for cancer: current insights," Onco Targets Ther. 9:6549-6559.

Cancer represents a prominent worldwide public health problem. The United States alone in 2015 had a total of 1,658,370 cases reported. See, Siegel et al., 2015, "Cancer statistics," CA Cancer J Clin. 65(1):5-29. Screening programs and early diagnosis have an important impact in improving disease-free survival and reducing mortality in cancer patients. As noninvasive approaches for early diagnosis foster patient compliance, they can be included in screening programs.

Noninvasive serum-based biomarkers used in clinical practice include carcinoma antigen 125 (CA 125), carcinoembryonic antigen, carbohydrate antigen 19-9 (CA19-9), and prostate-specific antigen (PSA) for the detection of ovarian, colon, and prostate cancers, respectively. See, Terry et al., 2016, "A prospective evaluation of early detection biomarkers for ovarian cancer in the European EPIC cohort," Clin Cancer Res. 2016 Apr. 8; Epub and Zhang et al., "Tumor markers CA19-9, CA242 and CEA in the diagnosis of pancreatic cancer: a meta-analysis," Int J Clin Exp Med. 2015; 8(7):11683-11691.

These biomarkers generally have low specificity (high number of false-positive results). Thus, new noninvasive biomarkers are actively being sought. The increasing knowledge of the molecular pathogenesis of cancer and the rapid development of new molecular techniques such as next generation nucleic acid sequencing techniques is promoting the study of early molecular alterations in body fluids.

Cell-free DNA (cfDNA) can be found in serum, plasma, urine, and other body fluids (Chan et al., "Clinical Sciences Reviews Committee of the Association of Clinical Biochemists Cell-free nucleic acids in plasma, serum and urine: a new tool in molecular diagnosis," Ann Clin Biochem. 2003; 40(Pt 2):122-130) representing a "liquid biopsy," which is a circulating picture of a specific disease. See, De Mattos-Arruda and Caldas, 2016, "Cell-free circulating tumour DNA as a liquid biopsy in breast cancer," Mol Oncol. 2016; 10(3):464-474.

The existence of cfDNA was demonstrated by Mandel and Metais (Mandel and Metais), "P. Les acides nucleiques du plasma sanguin chez 1' homme [The nucleic acids in blood plasma in humans]," C R Seances Soc Biol Fil. 1948; 142(3-4):241-243). cfDNA originates from necrotic or apoptotic cells, and it is generally released by all types of cells. Stroun et al. showed that specific cancer alterations could be found in the cfDNA of patients. See, Stroun et al., "Neoplastic characteristics of the DNA found in the plasma of cancer patients," Oncology. 1989; 46(5):318-322). A number of following papers confirmed that cfDNA contains specific tumor-related alterations, such as mutations, methylation, and copy number variations (CNVs), thus confirming the existence of circulating tumor DNA (ctDNA). See, Goessl et al., "Fluorescent methylation-specific polymerase chain reaction for DNA-based detection of prostate cancer in bodily fluids," Cancer Res. 2000; 60(21):5941-5945 and Frenel et al., 2015, "Serial next-generation sequencing of circulating cell-free DNA evaluating tumor clone response to molecularly targeted drug administration. Clin Cancer Res. 21(20):4586-4596.

cfDNA in plasma or serum is well characterized, while urine cfDNA (ucfDNA) has been traditionally less characterized. However, recent studies demonstrated that ucfDNA could also be a promising source of biomarkers. See, Casadio et al., 2013, "Urine cell-free DNA integrity as a marker for early bladder cancer diagnosis: preliminary data," Urol Oncol. 2013; 31(8):1744-1750.

In blood, apoptosis is a frequent event that determines the amount of cfDNA. In cancer patients, however, the amount of cfDNA seems to be also influenced by necrosis. See Hao et al., "Circulating cell-free DNA in serum as a biomarker for diagnosis and prognostic prediction of colorectal cancer," Br J Cancer. 2014; 111(8):1482-1489 and Zonta et al., "Assessment of DNA integrity, applications for cancer research," Adv Clin Chem. 2015; 70:197-246. Since apoptosis seems to be the main release mechanism, circulating cfDNA has a size distribution that reveals an enrichment in short fragments of about 167 bp, (see, Heitzer et al., 2015, "Circulating tumor DNA as a liquid biopsy for cancer," Clin Chem. 61(1):112-123 and Lo et al., 2010, "Maternal plasma DNA sequencing reveals the genome-wide genetic and mutational profile of the fetus," Sci Transl Med. 2(61): 61ra91) corresponding to nucleosomes generated by apoptotic cells.

The amount of circulating cfDNA in serum and plasma seems to be significantly higher in patients with tumors than in healthy controls, especially in those with advanced-stage tumors than in early-stage tumors. See, Sozzi et al., 2003 "Quantification of free circulating DNA as a diagnostic marker in lung cancer," J Clin Oncol. 21(21):3902-3908, Kim et al., 2014, "Circulating cell-free DNA as a promising biomarker in patients with gastric cancer: diagnostic validity and significant reduction of cfDNA after surgical resection," Ann Surg Treat Res. 2014; 86(3):136-142; and Shao et al. 2015 "Quantitative analysis of cell-free DNA in ovarian cancer," Oncol Lett. 2015; 10(6):3478-3482). The variability of the amount of circulating cfDNA is higher in cancer patients than in healthy individuals, (Heitzer et al., 2013, "Establishment of tumor-specific copy number alterations from plasma DNA of patients with cancer," Int J Cancer. 133(2):346-356) and the amount of circulating cfDNA is influenced by several physiological and pathological conditions, including proinflammatory diseases. See, Raptis and Menard, 1980, "Quantitation and characterization of plasma DNA in normals and patients with systemic lupus erythematosus," J Clin Invest. 66(6):1391-1399, and Shapiro et al., 1983, "Determination of circulating DNA levels in patients with benign or malignant gastrointestinal disease," Cancer. 51(11):2116-2120.

Mouliere et al., Sci Transl Med., 10(466) (2018), the content of which is incorporated herein by reference, in its entirety, for all purposes, recognized differences in the fragment length of cfDNA fragments derived from tumors and cfDNA fragments derived from non-cancerous cells. Further, Mouliere et al. identified that certain features relating to the differences in the size distribution of tumor-derived cfDNA fragment could be diagnostic of the presence of advanced cancers. For instance, Mouliere et al. performed predictive analysis using ten features relating to fragment size distribution: five features based on the based on the proportion (P) of fragments in defined size ranges: P(20 to 150), P(100 to 150), P(160 to 180), P(180 to 220), and P(250 to 320); three features based on ratios of those proportions: P(20 to 150)/P(160 to 180), P(100 to 150)/P(163 to 169), and P(20 to 150)/P(180 to 220); one feature based on the amplitude of oscillations having 10-bp periodicity observed below 150 bp; and a statistic (t-MAD; trimmed median absolute deviation from copy number neutrality) relating to the level of copy number variation across the entire genome. Specifically, Mouliere et al. found that the best feature set for classifying cancer by logistic regression included t-MAD, 10-bp amplitude, P(160 to 180), P(180 to 220), and P(250 to 320). Further analysis revealed that the cfDNA fragmentation pattern, as opposed to the t-MAD statistic, was the most important predictive feature.

Mouliere et al., also found that in certain, high ctDNA cancers, but not low ctDNA cancers such as renal cancer, glioblastoma, bladder, and pancreatic cancers, the proportion of tumor-derived cfDNA fragments was higher in cfDNA fragments 150 nucleotides or less in length. And that by selecting cfDNA fragments having these smaller lengths, the t-MAD global statistic had some prognostic power to distinguish between healthy samples and high ctDNA cancers, but not low ctDNA cancers such as renal cancer, glioblastoma, bladder, and pancreatic cancers. Mouliere et al. warns in several places, however, that although selecting smaller cfDNA fragments may increase the sensitivity of detecting tumor-derived cfDNA molecules, it results in the loss of informative cfDNA, including tumor-derived cfDNA fragments which are larger than 150 nucleotides.

Whole genome sequencing (WGS) and whole exome sequencing (WES) may be beneficial to cancer classification. However, these methodologies are relatively slow and expensive. Moreover, these techniques have only been found to be viable in samples having tumor fractions above about 5%. See, for example, Adalsteinsson, V. A. et al., Nat. Commun., 8(1324) (2017); Belic, J. et al., Clin. Chem., 61:838-49 (2015); Heitzer, E. et al., Genome Med. 5(30) (2013); and Murtaza, M. et al., Nature, 497:108-12 (2013), the contents of which are incorporated by reference, in their entireties, for all purposes.

SUMMARY

Improved methods for classifying cancer in a subject are needed. The present disclosure addressed the shortcomings identified in the background by providing more sensitive, faster, and less expensive methods for classifying a cancer using size-selected cell-free DNA (cfDNA) sequence reads, e.g., where the size selection occurs in vitro, i.e., prior to sequencing, or in silico, i.e., after sequencing. These methodologies are based, in part, on the discovery that size-selected cfDNA sequencing reads provide higher diagnostic power at lower sequence coverage, and despite containing sequence reads from fewer cancer-derived cfDNA fragments than non-size-selected cfDNA sequencing reads. The disclosure also provides improved methods for classifying cancers based on tumor-derived cfDNA using the size-selection methodology described herein. Significantly, the methods disclosed herein enrich the fraction of cancer-derived cfDNA fragments in cancer samples from all types of cancers, including low tumor-derived cfDNA cancers. Further, the methodologies described herein facilitate classification of cancers having very low tumor fractions (e.g., early stage cancers and low ctDNA cancers), even below 1% tumor fraction.

One aspect of the present disclosure provides methods, and systems for performing methods, of evaluating size-selected cell-free DNA sequence reads (where the size selection occurs in vitro, i.e., prior to sequencing, or in silico, i.e., after sequencing) to determine a cancer class of a subject. The method includes obtaining, at a computer system, sequence reads, in electronic form, from a biological sample of the subject that includes cell-free DNA molecules that are longer than a first threshold length that is less than 160 nucleotides. The sequence reads exclude most or all sequence reads of cell-free DNA molecules longer than the first threshold length. The method then includes using the sequence reads to identify a relative copy number either randomly across the genome or at predetermined genomic locations in the genome of the subject. Generally, this includes at least fifty genomic locations. The method then includes classifying the subject, which includes applying genetic information about the subject obtained from the biological sample, where the genetic information is the identification of the relative copy number at each respective genomic location, to a classifier, thereby determining the cancer class of the subject.

One aspect of the present disclosure provides methods, and systems for performing methods, of determining the relative copy number at a plurality of genomic locations in a pool of size-selected cell-free DNA molecules. The method includes obtaining cell-free DNA molecules from biological samples of a plurality of subjects. The method then includes adding a nucleic acid fragment having a fixed length of x nucleotides to the cell-free DNA molecules of each respective subject, where the nucleic acid fragment includes an identifier unique to the respective subject. The method then includes pooling the cell-free DNA molecules from each respective subject before isolating cell-free DNA molecules in the pool having a length that is no longer than a first threshold length, which is less than 160+x, thereby forming a length-selected pool of cell-free DNA molecules. The method then includes determining the relative copy number either randomly across the genome or at predetermined genomic locations of the cell-free DNA molecules in the length-selected pool of cell-free DNA molecules.

One aspect of the present disclosure provides methods, and systems for performing methods, of classifying the cancer status of a patient with renal cancer, glioblastoma, bladder cancer, or pancreatic cancer. The method includes obtaining sequence reads, in electronic form, from a biological sample of the subject containing cell-free DNA molecules that are longer than a threshold length which is less than 160 nucleotides. The sequence reads excluding sequence reads of cell-free DNA molecules that are longer than the first threshold length. The method then includes using the sequence reads to identify the copy number of a plurality of genomic locations in the genome of the subject, e.g., at least one hundred genomic locations. The method then includes classifying the subject by applying the copy numbers to a classifier. Advantageously, as compared to prior reports, size-selection of cfDNA fragments from cancers that tend to shed less into the bloodstream does improve the diagnostic power of the data, e.g., by increasing the tumor fraction of the sequence reads.

One aspect of the present disclosure provides methods, and systems for performing methods, of determining whether an undiagnosed subject has cancer. The method includes obtaining a first plurality of sequence reads, in electronic form, from a biological sample of the subject. The biological sample includes a first plurality of cell-free DNA molecules including respective DNA molecules that are longer than a first threshold length, where the first threshold length is less than 160 nucleotides. The first plurality of sequence reads excludes sequence reads of cell-free DNA molecules in the first plurality of cell-free DNA molecules longer than the first threshold length. The method then includes using the first plurality of sequence reads to identify a relative copy number at each respective genomic location in a plurality of genomic locations in the genome of the subject, e.g., where the plurality of genomic locations includes at least one hundred genomic locations. The method then includes classifying the subject by applying the identification of the relative copy number at each respective genomic location to a classifier, thereby determining a cancer class of the subject, where the cancer class of the subject is a presence or absence of a cancer selected from a set of cancers, where the set of cancers includes renal cancer, glioblastoma, bladder cancer, or pancreatic cancer. Advantageously, and contrary to the reports of others, it was discovered that size-selection of sequence reads actually improved the diagnostic power of sequence reads from cfDNA fragments from samples from subjects with cancers that tend to shed less into the bloodstream. Accordingly, the present disclosure enables methods for classifying a wide range of cancers, including those cancers, such as renal cancer, glioblastoma, bladder cancer, or pancreatic cancer, using a single classifier that leverages size-selected sequence reads.

Other embodiments are directed to systems, portable consumer devices, and computer readable media associated with methods described herein.

As disclosed herein, any embodiment disclosed herein when applicable can be applied to any aspect, alone or in combination with one or more other embodiments.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

BRIEF DESCRIPTION OF THE DRAWINGS

FIG. 2A provides a flow chart for a method of determining a cancer status of a subject using in vitro size-selected cell-free DNA from a biological sample of the subject, in accordance with various embodiments of the present disclosure.

FIGS. 3A, 3B, 3C, 3D, 3E, 3F, and 3G collectively provide a flow chart of processes and features for determining a cancer status of a subject using sequence reads of in vitro size-selected cell-free DNA molecules, or in silico size-selected sequence reads of total cell-free DNA, from a biological sample of the subject, in accordance with various embodiments of the present disclosure, in accordance with various embodiments of the present disclosure.

FIGS. 4A, 4B, 4C, 4E, and 4F collectively provide a flow chart of processes and features for determining the relative copy number at a plurality of genomic locations in a pool of size-selected cell-free DNA molecules, in accordance with various embodiments of the present disclosure.

FIG. 8E shows cancer-stage dependent statistics for the classifications shown in FIGS. 8C and 8D using in silico size-selected sequence reads.

FIG. 8H shows cancer-stage dependent statistics for classifications shown in FIGS. 8F and 8G using in silico size-selected sequence reads.

FIGS. 9A, 9B, and 9C illustrate histograms of sequencing coverage obtained from sub-sampling 35×CCGA data sets to approximately 5× sequence coverage (FIG. 9A), filtered in silico to only include sequences from cfDNA fragments having a size of from 100 nucleotides or less from the sub-sampled 5× data set (FIG. 9C), and random sampling of the 5× data set to achieve the same sequence coverage as the corresponding size-selected data set (FIG. 9B).

FIG. 22 illustrates a plot of MAPD for the copy number of adjacent genomic locations of sequencing data generated from cfDNA fragments following size-selection as a function of MAPD for the sequence reads generated from the matched non-size-selected cfDNA sample, as described in Example 12.

Like reference numerals refer to corresponding parts throughout the several views of the drawings.

DETAILED DESCRIPTION

The present disclosure provides systems and methods for classifying a subject for a cancer condition based on analysis of sequence reads from cell-free DNA fragments, in a biological fluid from the subject, that are shorter than a threshold length that is determined such that, if the subject has cancer, the sequence reads are enriched for those from cell-free DNA fragments originating from the cancer. Advantageously, as described herein, Applicants have developed various methodologies that improve the confidence with which a cancer classification is made. In fact, some of these methodologies not only improve the confidence with which the cancer classification is made, but also reduce the amount of DNA sequencing data required for the classification which, in turn, improves the speed of the process while reducing the cost and computational burden of the analysis.

Figure 11:
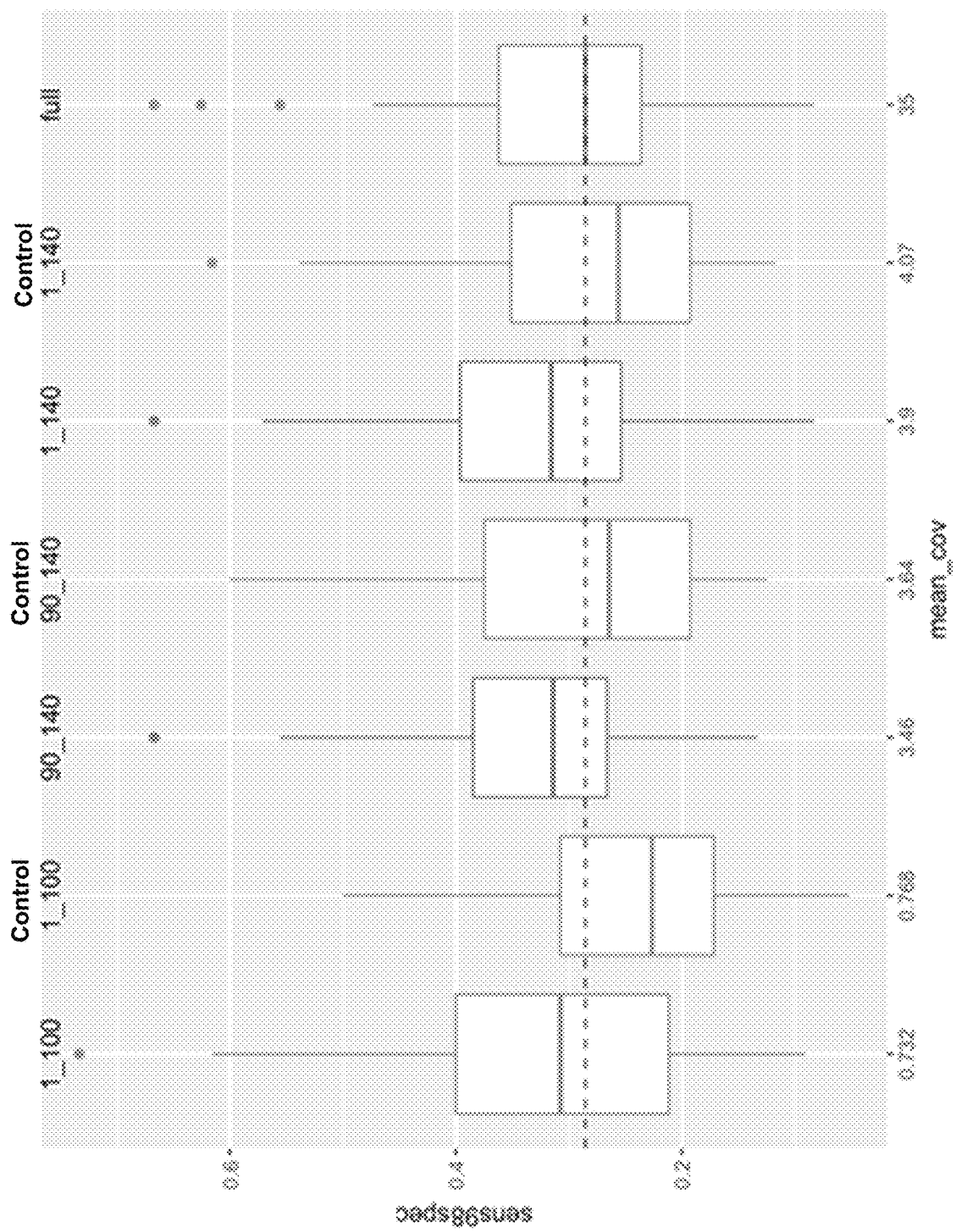
FIG. 11 illustrates box plots of the specificity of cancer classification using full (unfiltered) CCGA WGS data sets, size-selected (filtered) CCGA WGS data sets at 100 nucleotides or less, 90-140 nucleotides, and 140 or less nucleotides, and control data sets with randomly selected sequence reads from the full (unfiltered) CCG AWGS data sets to match the sequence coverage of the seize-selected (filtered) CCG AWGS data sets, as described in Example 7. The corresponding plots generated for the same size-selection in the full 35× samples, as shown in FIG. 8, is displayed for comparison purposes.
Figure 12A:
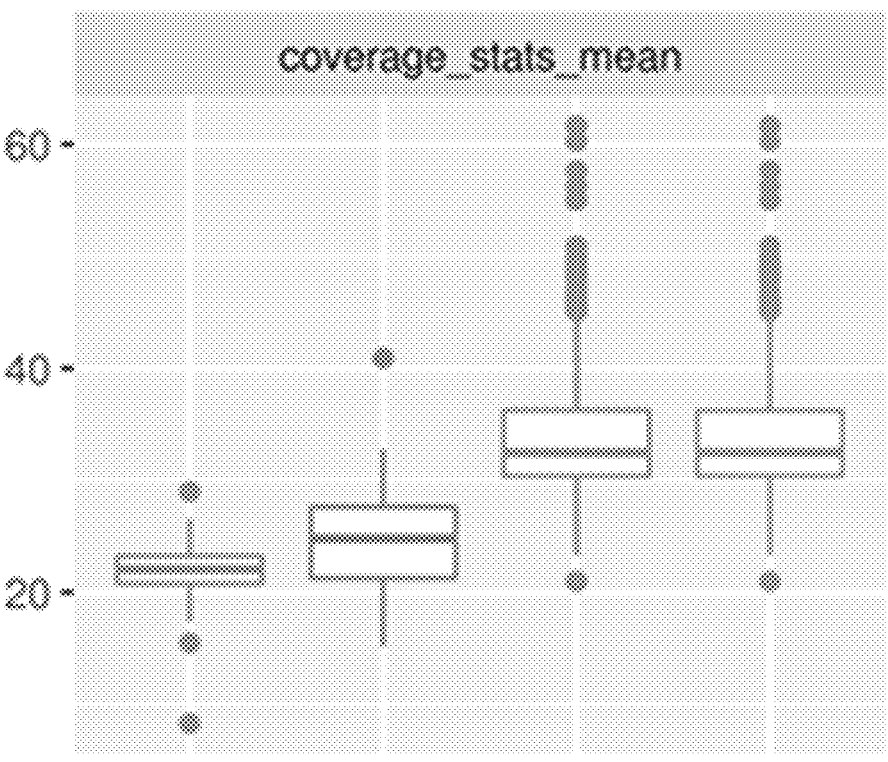
FIGS. 12A, 12B, 12C, and 12D illustrate metrics for sequencing reactions performed using in vitro size-selected cfDNA fragments, as described in Example 9.
Figure 12B:
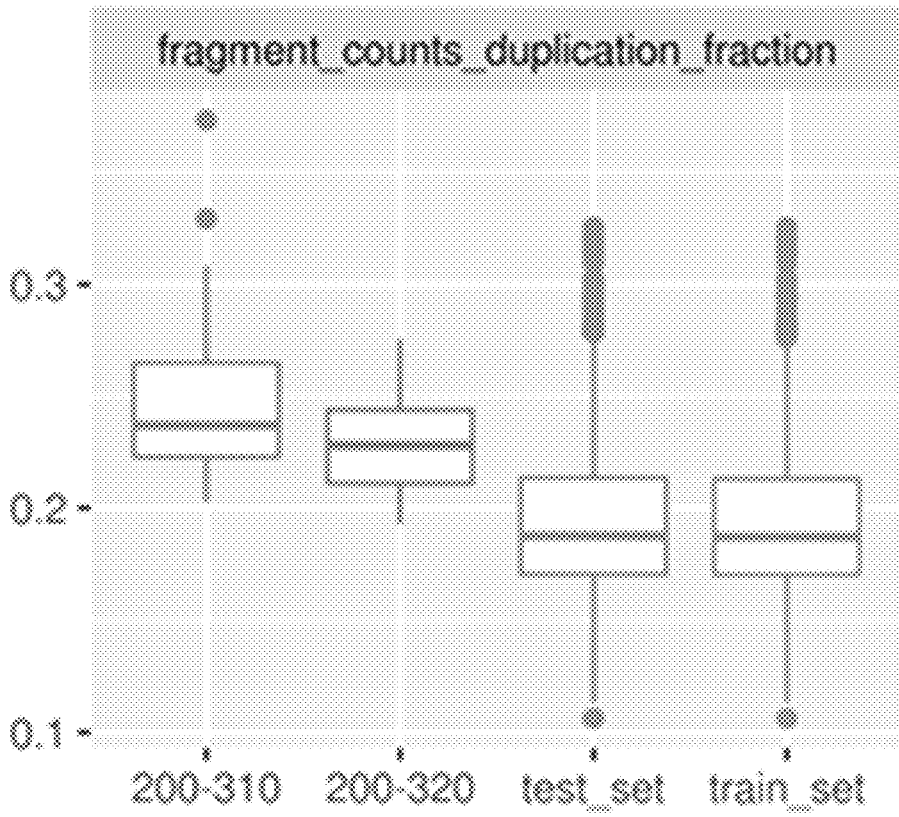
Figure 12C:
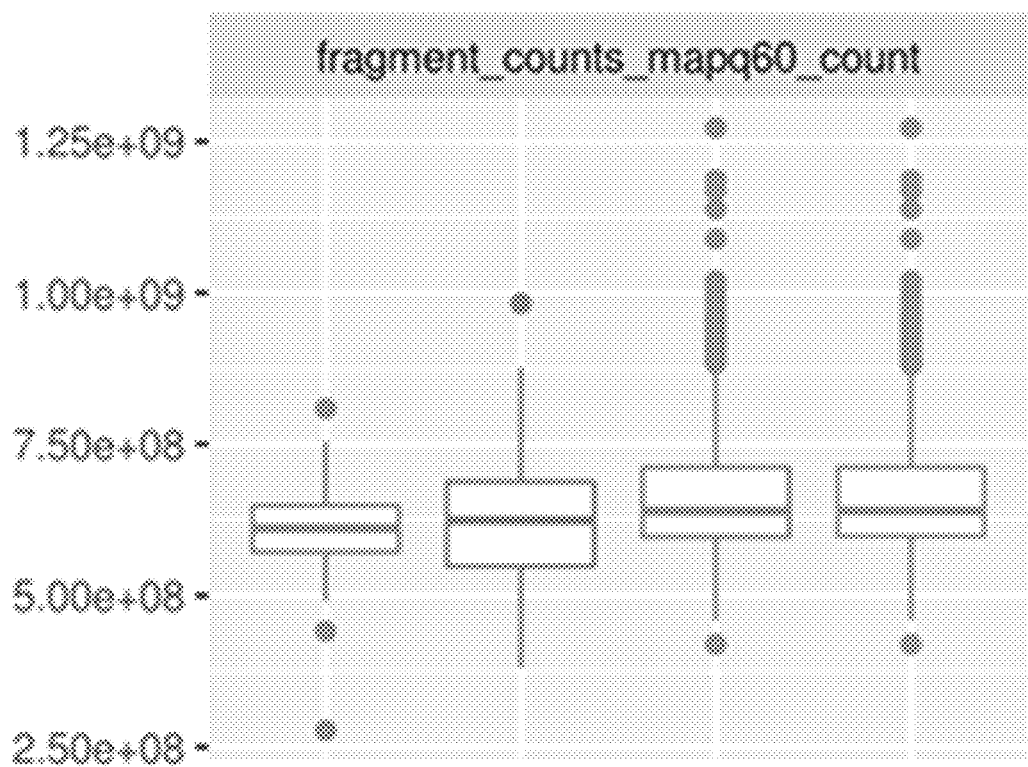
Figure 12D:
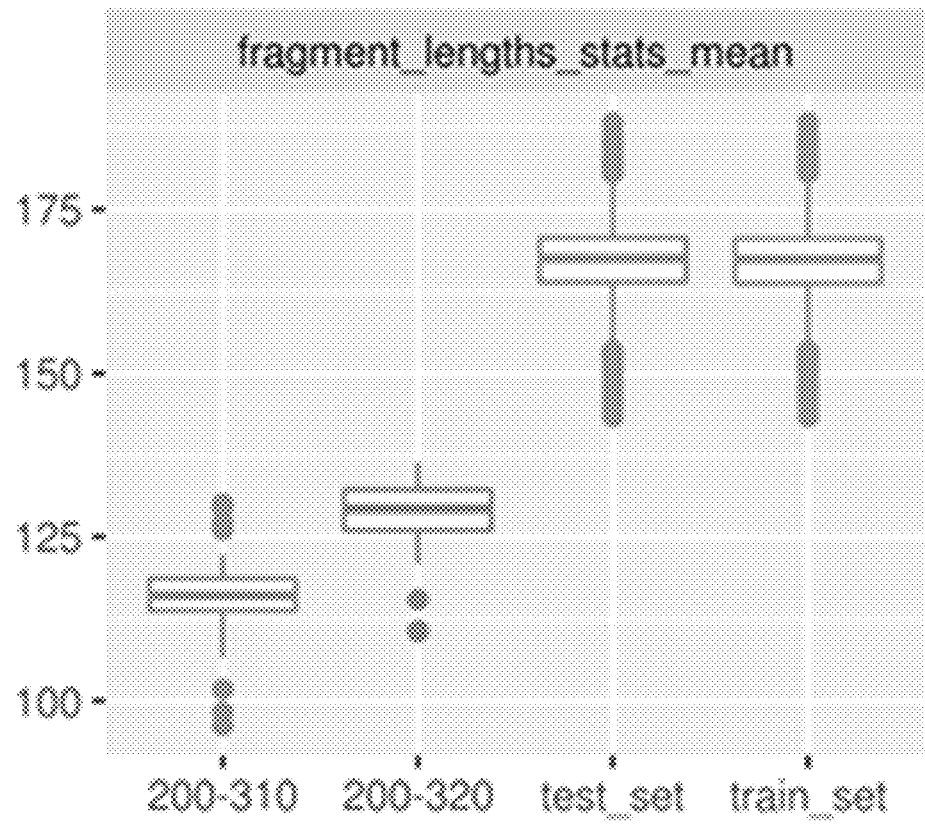

In one aspect, the disclosure provides improved systems and methods for classifying a subject for a cancer condition based on analysis of sequence reads of cell-free DNA, from a biological sample of the subject, that are filtered in silico to enrich for sequence reads from cancer cell-derived fragments, e.g., by removing sequence reads of cell-free DNA fragments that are larger than a threshold length that is less than 160 nucleotides. Advantageously, because the filtered set of sequence reads includes fewer sequence reads than the full set of sequence reads obtained from sequencing the cell-free DNA from the sample, the computational burden of processing the data set and applying the processed data to a classifier is reduced, improving the efficiency of computer systems used to classify the cancer state of a subject and reducing the overall time. Moreover, it was unexpectedly found that the confidence with which the classifications are made were improved by using the filtered data sets, despite that a significant portion of the available data is removed through the filtration process. For instance, as described in Examples 4-7, the use of sequencing data that is filtered in silico to remove sequence reads from cfDNA molecules having lengths of more than 150 nucleotides improves the sensitivity of cancer detection using a classifier based on copy number variation of a predetermined number of genomic bins. Specifically, FIGS. 8 and 11 show increased sensitivity of the classification at 95%, 98%, and 99% specificity, using sequencing data from cfDNA fragments of 1-100 nucleotides, 0-140 nucleotides, 90-140, and 90-150 nucleotides.

Figure 14:
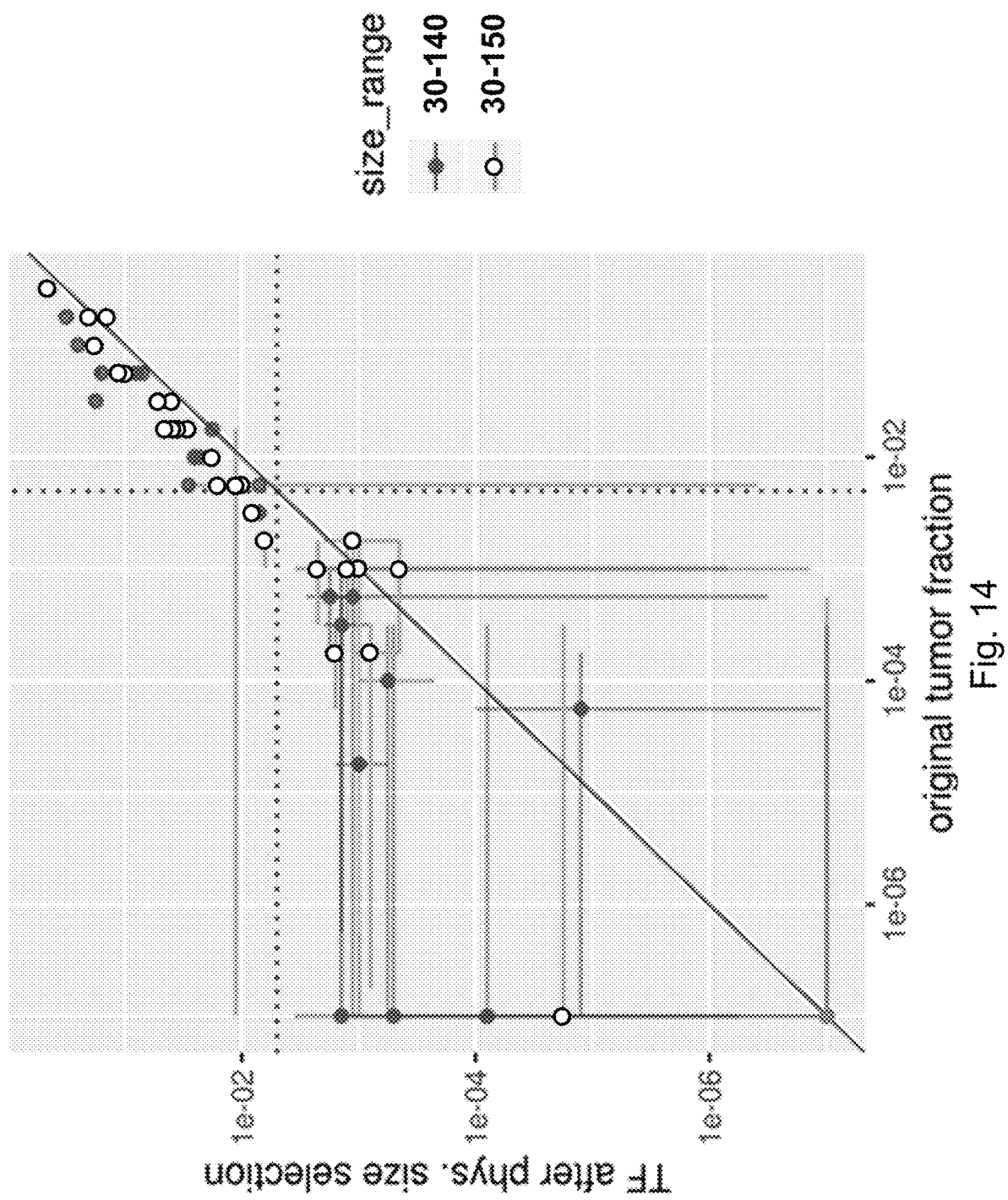
FIG. 14 illustrates the estimated fraction of cancer-derived cfDNA fragments (tumor fraction) in samples before (x-axis) and after (y-axis) in vitro size selection, as described in Example 10.

In one aspect, the disclosure provides improved systems and methods for classifying a subject for a cancer condition based on analysis of sequence reads of cell-free DNA, from a biological sample of the subject, that are size selected in vitro to remove cell-free DNA fragments that are larger than a threshold length, e.g., that is less than 160 nucleotides. Advantageously, because the cell-free DNA from the biological sample is size selected, the total amount of DNA that needs to be sequenced is reduced. In turn, more samples can be combined in a single sequencing reaction, reducing the sequencing cost and time per sample. Further, because fewer sequence reads are generated from each sample, the computational burden of processing the data set and applying the processed data to a classifier is reduced, improving the efficiency of computer systems used to classify the cancer state of a subject and reducing the overall time. Moreover, it was unexpectedly found that the confidence with which the classifications are made were improved by using the small data set, despite that a significant portion of potential sequencing data from the sample is not obtained. For instance, as described in Example 10, the fraction of sequence reads originating from cancer-derived cfDNA fragments is enriched in sequencing data generated from cfDNA samples following size selection of cfDNA fragments in the 30-140 and 30-150 nucleotide ranges. Specifically, FIG. 14 shows that in vitro size selection increases tumor fraction in almost every sample one of 65 samples from subjects diagnosed with one of ten cancers and representing a distribution of all cancer stages. Further, Example 11 suggests the use of sequencing data generated from in vitro size selected cfDNA fragments improves the sensitivity of cancer detection using a classifier based on copy number variation of a predetermined number of genomic bins. Specifically, it is reported in Table 6 that in vitro size selection of the cfDNA fragments improved the sensitivity of the classifier by about 20-30% at 95%, 98%, and 95% specificity In one aspect, the disclosure provides improved systems and methods for classifying renal cancer, glioblastoma, bladder cancer, or pancreatic cancer using sequencing data from cell-free DNA. Advantageously, it was discovered that excluding sequencing data from cell-free DNA fragments that are longer than a predetermined threshold, e.g., that is less than 160 nucleotides, increased the percentage of sequence reads from renal cancer, glioblastoma, bladder cancer, or pancreatic cancer-derived cell-free DNA fragments. Further, because the filtered set of sequence reads includes fewer sequence reads, the computational burden of processing the data set and applying the processed data to a classifier is reduced, improving the efficiency of computer systems used to classify the cancer state of a subject and reducing the overall time. Moreover, it was unexpectedly found that the confidence with which the classifications are made were improved by using the filtered data sets, despite that a significant portion of the available data is removed through the filtration process. For instance, as described in Example 5, in silico size selection across all cancer types in the CCGA data set, which include renal cancer, bladder cancer, and pancreatic cancer, provided improvements in classification sensitivity at both 95% specificity and 99% specificity, against both the full data sets and the sequence coverage-matched control data sets. The classification statistics for this analysis are presented in Table 1.

Definitions

The terminology used in the present disclosure is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Furthermore, to the extent that the terms "including," "includes," "having," "has," "with," or variants thereof are used in either the detailed description and/or the claims, such terms are intended to be inclusive in a manner similar to the term "comprising."

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject. Furthermore, the terms "subject," "user," and "patient" are used interchangeably herein.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

As used herein, the term "about" or "approximately" mean within an acceptable error range for the particular value as determined by one of ordinary skill in the art, which depends in part on how the value is measured or determined, e.g., the limitations of the measurement system. For example, in some embodiments "about" mean within 1 or more than 1 standard deviation, per the practice in the art. In some embodiments, "about" means a range of ±20%, ±10%, ±5%, or ±1% of a given value. In some embodiments, the term "about" or "approximately" means within an order of magnitude, within 5-fold, or within 2-fold, of a value. Where particular values are described in the application and claims, unless otherwise stated the term "about" meaning within an acceptable error range for the particular value should be assumed. The term "about" can have the meaning as commonly understood by one of ordinary skill in the art. In some embodiments, the term "about" refers to ±10%. In some embodiments, the term "about" refers to ±5%.

As used herein, the term "subject" refers to any living or non-living organism, including but not limited to a human (e.g., a male human, female human, fetus, pregnant female, child, or the like), a non-human animal, a plant, a bacterium, a fungus or a protist. Any human or non-human animal can serve as a subject, including but not limited to mammal, reptile, avian, amphibian, fish, ungulate, ruminant, bovine (e.g., cattle), equine (e.g., horse), caprine and ovine (e.g., sheep, goat), swine (e.g., pig), camelid (e.g., camel, llama, alpaca), monkey, ape (e.g., gorilla, chimpanzee), ursid (e.g., bear), poultry, dog, cat, mouse, rat, fish, dolphin, whale and shark. In some embodiments, a subject is a male or female of any stage (e.g., a man, a women or a child). In one embodiment, the subject is a human.

As used herein, the phrase "healthy" refers to a subject possessing good health. A healthy subject can demonstrate an absence of any malignant or non-malignant disease. A "healthy individual" can have other diseases or conditions, unrelated to the condition being assayed, which can normally not be considered "healthy."

As used herein, the term "biological fluid sample," "biological sample," "patient sample," or "sample" refers to any sample taken from a subject, which can reflect a biological state associated with the subject, and that includes cell free DNA. Examples of biological samples include, but are not limited to, blood, whole blood, plasma, serum, urine, cerebrospinal fluid, fecal, saliva, sweat, tears, pleural fluid, pericardial fluid, or peritoneal fluid of the subject. In some embodiments, the biological sample consists of blood, whole blood, plasma, serum, urine, cerebrospinal fluid, fecal, saliva, sweat, tears, pleural fluid, pericardial fluid, or peritoneal fluid of the subject. In such embodiments, the biological sample is limited to blood, whole blood, plasma, serum, urine, cerebrospinal fluid, fecal, saliva, sweat, tears, pleural fluid, pericardial fluid, or peritoneal fluid of the subject and does not contain other components (e.g., solid tissues, etc.) of the subject. A biological sample can include any tissue or material derived from a living or dead subject.

A biological sample can be a cell-free sample. A biological sample can comprise a nucleic acid (e.g., DNA or RNA) or a fragment thereof. The term "nucleic acid" can refer to deoxyribonucleic acid (DNA), ribonucleic acid (RNA) or any hybrid or fragment thereof. The nucleic acid in the sample can be a cell-free nucleic acid. A sample can be a liquid sample or a solid sample (e.g., a cell or tissue sample). A biological sample can be a bodily fluid, such as blood, plasma, serum, urine, vaginal fluid, fluid from a hydrocele (e.g., of the testis), vaginal flushing fluids, pleural fluid, ascitic fluid, cerebrospinal fluid, saliva, sweat, tears, sputum, bronchoalveolar lavage fluid, discharge fluid from the nipple, aspiration fluid from different parts of the body (e.g., thyroid, breast), etc. A biological sample can be a stool sample. In various embodiments, the majority of DNA in a biological sample that has been enriched for cell-free DNA (e.g., a plasma sample obtained via a centrifugation protocol) can be cell-free (e.g., greater than 50%, 60%, 70%, 80%, 90%, 95%, or 99% of the DNA can be cell-free). A biological sample can be treated to physically disrupt tissue or cell structure (e.g., centrifugation and/or cell lysis), thus releasing intracellular components into a solution which can further contain enzymes, buffers, salts, detergents, and the like which can be used to prepare the sample for analysis. A biological sample can be obtained from a subject invasively (e.g., surgical means) or non-invasively (e.g., a blood draw, a swab, or collection of a discharged sample).

As used herein, the terms "control," "control sample," "reference," "reference sample," "normal," and "normal sample" describe a sample from a subject that does not have a particular condition, or is otherwise healthy. In an example, a method as disclosed herein can be performed on a subject having a tumor, where the reference sample is a sample taken from a healthy tissue of the subject. A reference sample can be obtained from the subject, or from a database. The reference can be, e.g., a reference genome that is used to map sequence reads obtained from sequencing a sample from the subject. A reference genome can refer to a haploid or diploid genome to which sequence reads from the biological sample and a constitutional sample can be aligned and compared. An example of a constitutional sample can be DNA of white blood cells obtained from the subject. For a haploid genome, there can be only one nucleotide at each locus. For a diploid genome, heterozygous loci can be identified; each heterozygous locus can have two alleles, where either allele can allow a match for alignment to the locus.

As used herein, the terms "nucleic acid" and "nucleic acid molecule" are used interchangeably. The terms refer to nucleic acids of any composition form, such as deoxyribonucleic acid (DNA, e.g., complementary DNA (cDNA), genomic DNA (gDNA) and the like), and/or DNA analogs (e.g., containing base analogs, sugar analogs and/or a non-native backbone and the like), all of which can be in single- or double-stranded form. Unless otherwise limited, a nucleic acid can comprise known analogs of natural nucleotides, some of which can function in a similar manner as naturally occurring nucleotides. A nucleic acid can be in any form useful for conducting processes herein (e.g., linear, circular, supercoiled, single-stranded, double-stranded and the like). A nucleic acid in some embodiments can be from a single chromosome or fragment thereof (e.g., a nucleic acid sample may be from one chromosome of a sample obtained from a diploid organism). In certain embodiments nucleic acids comprise nucleosomes, fragments or parts of nucleosomes or nucleosome-like structures. Nucleic acids sometimes comprise protein (e.g., histones, DNA binding proteins, and the like). Nucleic acids analyzed by processes described herein sometimes are substantially isolated and are not substantially associated with protein or other molecules. Nucleic acids also include derivatives, variants and analogs of DNA synthesized, replicated or amplified from single-stranded ("sense" or "antisense," "plus" strand or "minus" strand, "forward" reading frame or "reverse" reading frame) and double-stranded polynucleotides. Deoxyribonucleotides include deoxyadenosine, deoxycytidine, deoxyguanosine and deoxythymidine. A nucleic acid may be prepared using a nucleic acid obtained from a subject as a template.

As used herein, the term "cell-free nucleic acids" refers to nucleic acid molecules that can be found outside cells, in bodily fluids such as blood, whole blood, plasma, serum, urine, cerebrospinal fluid, fecal, saliva, sweat, sweat, tears, pleural fluid, pericardial fluid, or peritoneal fluid of a subject. Cell-free nucleic acids originate from one or more healthy cells and/or from one or more cancer cells Cell-free nucleic acids are used interchangeably as circulating nucleic acids. Examples of the cell-free nucleic acids include but are not limited to RNA, mitochondrial DNA, or genomic DNA. As used herein, the terms "cell free nucleic acid," "cell free DNA," and "cfDNA" are used interchangeably. As used herein, the term "circulating tumor DNA" or "ctDNA" refers to nucleic acid fragments that originate from tumor cells or other types of cancer cells, which may be released into a fluid from an individual's body (e.g., bloodstream) as result of biological processes such as apoptosis or necrosis of dying cells or actively released by viable tumor cells.

As used herein, the term "genomic location" refers to a position (e.g., a site) within a genome, i.e., on a particular chromosome. In some embodiments, a genomic location refers to a single nucleotide position within a genome, i.e., on a particular chromosome. In some embodiments, a genomic location refers to a small group of consecutive nucleotide positions within a genome, e.g., as defined by a mutation (e.g., substitution, insertion, or deletion) of consecutive nucleotides within a cancer genome. In some embodiments, a genomic location refers to a large group of consecutive nucleotide positions within a genome, e.g., a 1 kb, 2 kb, 3 kb, 4 kb, 5 kb, 10 kb, 25 kb, 50 kb, 75 kb, 100 kb, 150 kb, 200 kb, 250 kb, or larger stretch of nucleotides within a genome. In some embodiments, the genome of a subject is divided into a plurality of genomic locations, e.g., bins of approximately the same size. Because normal mammalian cells have diploid genomes, a normal mammalian genome (e.g., a human genome) will generally have two copies of every locus in the genome, or at least two copies of every locus located on the autosomal chromosomes, i.e., one copy on the maternal autosomal chromosome and one copy on the paternal autosomal chromosome.

As used herein, the term "allele" refers to a particular sequence of one or more nucleotides at a chromosomal locus.

As used herein, the term "reference allele" refers to the sequence of one or more nucleotides at a chromosomal locus that is either the predominant allele represented at that chromosomal locus within the population of the species (e.g., the "wild-type" sequence), or an allele that is pre-defined within a reference genome for the species.

As used herein, the term "variant allele" refers to a sequence of one or more nucleotides at a chromosomal locus that is either not the predominant allele represented at that chromosomal locus within the population of the species (e.g., not the "wild-type" sequence), or not an allele that is predefined within a reference genome for the species.

As used herein, the term "single nucleotide variant" or "SNV" refers to a substitution of one nucleotide to a different nucleotide at a position (e.g., site) of a nucleotide sequence, e.g., a sequence read from an individual. A substitution from a first nucleobase X to a second nucleobase Y may be denoted as "X>Y." For example, a cytosine to thymine SNV may be denoted as "C>T."

As used herein, the term "mutation," refers to a detectable change in the genetic material of one or more cells. In a particular example, one or more mutations can be found in, and can identify, cancer cells (e.g., driver and passenger mutations). A mutation can be transmitted from apparent cell to a daughter cell. A person having skill in the art will appreciate that a genetic mutation (e.g., a driver mutation) in a parent cell can induce additional, different mutations (e.g., passenger mutations) in a daughter cell. A mutation generally occurs in a nucleic acid. In a particular example, a mutation can be a detectable change in one or more deoxyribonucleic acids or fragments thereof. A mutation generally refers to nucleotides that is added, deleted, substituted for, inverted, or transposed to a new position in a nucleic acid. A mutation can be a spontaneous mutation or an experimentally induced mutation. A mutation in the sequence of a particular tissue is an example of a "tissue-specific allele." For example, a tumor can have a mutation that results in an allele at a locus that does not occur in normal cells. Another example of a "tissue-specific allele" is a fetal-specific allele that occurs in the fetal tissue, but not the maternal tissue.

As used herein, the terms "somatic cells" and "germline cells" refer interchangeably to non-cancerous cells within a subject.

As used herein, the term "hematopoietic cells" refers to cells produced through hematopoiesis. Particularly relevant to the present disclosure are hematopoietic white blood cells, which contribute cell-free DNA fragments encompassing variant alleles that are created by clonal hematopoiesis, but which do not appear to represent a cancerous state in the subject.

As used herein the term "cancer" or "tumor" refers to an abnormal mass of tissue in which the growth of the mass surpasses and is not coordinated with the growth of normal tissue. A cancer or tumor can be defined as "benign" or "malignant" depending on the following characteristics: degree of cellular differentiation including morphology and functionality, rate of growth, local invasion and metastasis. A "benign" tumor can be well differentiated, have characteristically slower growth than a malignant tumor and remain localized to the site of origin. In addition, in some cases a benign tumor does not have the capacity to infiltrate, invade or metastasize to distant sites. A "malignant" tumor can be a poorly differentiated (anaplasia), have characteristically rapid growth accompanied by progressive infiltration, invasion, and destruction of the surrounding tissue. Furthermore, a malignant tumor can have the capacity to metastasize to distant sites. Accordingly, a cancer cell is a cell found within the abnormal mass of tissue whose growth is not coordinated with the growth of normal tissue.

As used herein, the Circulating Cell-free Genome Atlas or "CCGA" is defined as an observational clinical study that prospectively collects blood and tissue from newly diagnosed cancer patients as well as blood only from subjects who do not have a cancer diagnosis. The purpose of the study is to develop a pan-cancer classifier that distinguishes cancer from non-cancer and identifies tissue of origin.

As used herein, the term "level of cancer" refers to whether cancer exists (e.g., presence or absence), a stage of a cancer, a size of tumor, presence or absence of metastasis, an estimated tumor fraction concentration, a total tumor mutational burden value, the total tumor burden of the body, and/or other measure of a severity of a cancer (e.g., recurrence of cancer). The level of cancer can be a number or other indicia, such as symbols, alphabet letters, and colors. The level can be zero. The level of cancer can also include premalignant or precancerous conditions (states) associated with mutations or a number of mutations. The level of cancer can be used in various ways. For example, screening can check if cancer is present in someone who is not known previously to have cancer. Assessment can investigate someone who has been diagnosed with cancer to monitor the progress of cancer over time, study the effectiveness of therapies or to determine the prognosis. In one embodiment, the prognosis can be expressed as the chance of a subject dying of cancer, or the chance of the cancer progressing after a specific duration or time, or the chance of cancer metastasizing. Detection can comprise 'screening' or can comprise checking if someone, with suggestive features of cancer (e.g., symptoms or other positive tests), has cancer. A "level of pathology" can refer to level of pathology associated with a pathogen, where the level can be as described above for cancer. When the cancer is associated with a pathogen, a level of cancer can be a type of a level of pathology.

As used herein, the term "read segment" or "read" refers to any nucleotide sequences including sequence reads obtained from an individual and/or nucleotide sequences derived from the initial sequence read from a sample obtained from an individual. For example, a read segment can refer to an aligned sequence read, a collapsed sequence read, or a stitched read. Furthermore, a read segment can refer to an individual nucleotide base, such as a single nucleotide variant.

As used herein, the term "read-depth," "sequencing depth," or "depth" refers to a total number of read segments from a sample obtained from an individual at a given position, region, or locus. The locus can be as small as a nucleotide, or as large as a chromosome arm, or as large as an entire genome. Sequencing depth can be expressed as "Yx", e.g., 50×, 100×, etc., where "Y" refers to the number of times a locus is covered with a sequence read. In some embodiments, the depth refers to the average sequencing depth across the genome or across a targeted sequencing panel. Sequencing depth can also be applied to multiple loci, or the whole genome, in which case Y can refer to the mean number of times a loci or a haploid genome, or a whole genome, respectively, is sequenced. When a mean depth is quoted, the actual depth for different loci included in the dataset can span over a range of values. Ultra-deep sequencing can refer to at least 100× in sequencing depth at a locus.

As used herein, the term "read-depth metric" refers to a value that is characteristic of the total number of read segments from a biological sample that encompass a particular allele. In some embodiments, the read-depth metric refers to a value that is characteristic of the collapsed fragment coverage for a particular allele in a biological sample.

As used herein, the term "allele frequency" refers to the frequency at which a particular allele is represented at a particular genomic locus in the cell-free DNA of a biological sample, e.g., relative to the total occurrence of the loci in the biological sample. In some embodiments, allele frequency is calculated by dividing the read-depth of the allele in the biological sample by the read depth of the loci in the biological sample.

As used herein, the term "allele-frequency metric" refers to a value that is characteristic of the allele frequency for a particular allele in the biological sample.

As used herein, the terms "size profile" and "size distribution" can relate to the sizes of DNA fragments in a biological sample. A size profile can be a histogram that provides a distribution of an amount of DNA fragments at a variety of sizes. Various statistical parameters (also referred to as size parameters or just parameter) can distinguish one size profile to another. In some embodiments, one such parameter is the percentage of DNA fragment of a particular size or range of sizes relative to all DNA fragments or relative to DNA fragments of another size or range.

As used herein, the term "size-distribution metric" refers to a single value, or a set of values, that are characteristic of the distribution of cell-free DNA nucleic acid fragment sequences from a biological sample that encompass a particular allele. Subjects that have a single allele at a particular genomic locus will likewise have a single cell-free DNA fragment size distribution for the particular locus. Subjects that have two alleles at a particular genomic locus (e.g., a reference allele and a variant allele, regardless of the type of cell the variant allele originates from), however, will have two cell-free DNA fragment size distribution for the particular locus, from which two size-distribution metrics can be determined, e.g., one for the reference allele and one for the variant allele. In some embodiments, a size-distribution metric for an allele refers to a vector containing the lengths of each cell-free DNA fragment that was sequenced from a biological sample encompassing the allele. In some embodiments, a size-distribution metric refers to a single value that is representative of the distribution, e.g., a central tendency of length across the distribution, such as an arithmetic mean, weighted mean, midrange, midhinge, trimean, Winsorized mean, median, or mode of the distribution.

As used herein, the term "vector" is an enumerated list of elements, such as an array of elements, where each element has an assigned meaning. As such, the term "vector" as used in the present disclosure is interchangeable with the term "tensor." As an example, if a vector comprises the bin counts for 10,000 bins, there exists a predetermined element in the vector for each one of the 10,000 bins. For ease of presentation, in some instances a vector may be described as being one-dimensional. However, the present disclosure is not so limited. A vector of any dimension may be used in the present disclosure provided that a description of what each element in the vector represents is defined (e.g., that element 1 represents bin count of bin 1 of a plurality of bins, etc.).

As used herein, the terms "sequencing," "sequence determination," and the like as used herein refers generally to any and all biochemical processes that may be used to determine the order of biological macromolecules such as nucleic acids or proteins. For example, sequencing data can include all or a portion of the nucleotide bases in a nucleic acid molecule such as a DNA fragment.

As used herein, the term "sequence reads" or "reads" refers to nucleotide sequences produced by any sequencing process described herein or known in the art. Reads can be generated from one end of nucleic acid fragments ("single-end reads"), and sometimes are generated from both ends of nucleic acids (e.g., paired-end reads, double-end reads). The length of the sequence read is often associated with the particular sequencing technology. High-throughput methods, for example, provide sequence reads that can vary in size from tens to hundreds of base pairs (bp). In some embodiments, the sequence reads are of a mean, median or average length of about 15 bp to 900 bp long (e.g., about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, or about 500 bp. In some embodiments, the sequence reads are of a mean, median or average length of about 1000 bp, 2000 bp, 5000 bp, 10,000 bp, or 50,000 bp or more. Nanopore sequencing, for example, can provide sequence reads that can vary in size from tens to hundreds to thousands of base pairs. Illumina parallel sequencing can provide sequence reads that do not vary as much, for example, most of the sequence reads can be smaller than 200 bp. A sequence read (or sequencing read) can refer to sequence information corresponding to a nucleic acid molecule (e.g., a string of nucleotides). For example, a sequence read can correspond to a string of nucleotides (e.g., about 20 to about 150) from part of a nucleic acid fragment, can correspond to a string of nucleotides at one or both ends of a nucleic acid fragment, or can correspond to nucleotides of the entire nucleic acid fragment. A sequence read can be obtained in a variety of ways, e.g., using sequencing techniques or using probes, e.g., in hybridization arrays or capture probes, or amplification techniques, such as the polymerase chain reaction (PCR) or linear amplification using a single primer or isothermal amplification.

As used herein, the term "nucleic acid fragment sequence" refers to all or a portion of a polynucleotide sequence of at least three consecutive nucleotides. In the context of sequencing cell-free nucleic acid fragments found in a biological sample, the term "nucleic acid fragment sequence" refers to the sequence of a cell-free nucleic acid molecule (e.g., a cell-free DNA fragment) that is found in the biological sample or a representation thereof (e.g., an electronic representation of the sequence). Similarly, in the context of sequencing a locus within a larger polynucleotide, e.g., genomic DNA, the term "nucleic acid fragment sequence" refers to the sequence of the locus or a representation thereof. In such contexts, sequencing data (e.g., raw or corrected sequence reads from whole genome sequencing, targeted sequencing, etc.) from a unique nucleic acid fragment (e.g., a cell-free nucleic acid, genomic fragment, or a locus within a larger polynucleotide that is defined by a pair of PCR primers) are used to determine a nucleic acid fragment sequence. Such sequence reads, which in fact may be obtained from sequencing of PCR duplicates of the original nucleic acid fragment, therefore "represent" or "support" the nucleic acid fragment sequence. There may be a plurality of sequence reads that each represent or support a particular nucleic acid fragment in a biological sample (e.g., PCR duplicates), however, there will only be one nucleic acid fragment sequence for the particular nucleic acid fragment. In some embodiments, duplicate sequence reads generated for the original nucleic acid fragment are combined or removed (e.g., collapsed into a single sequence, e.g., the nucleic acid fragment sequence). Accordingly, when determining metrics relating to a population of nucleic acid fragments, in a sample, that each encompass a particular locus (e.g., an abundance value for the locus or a metric based on a characteristic of the distribution of the fragment lengths), the nucleic acid fragment sequences for the population of nucleic acid fragments, rather than the supporting sequence reads (e.g., which may be generated from PCR duplicates of the nucleic acid fragments in the population, should be used to determine the metric. This is because, in such embodiments, only one copy of the sequence is used to represent the original (e.g., unique) nucleic acid fragment (e.g., unique cell-free nucleic acid molecule). It is noted that the nucleic acid fragment sequences for a population of nucleic acid fragments may include several identical sequences, each of which represents a different original nucleic acid fragment, rather than duplicates of the same original nucleic acid fragment. In some embodiments, a cell-free nucleic acid is considered a nucleic acid fragments.

As used herein the term "sequencing breadth" refers to what fraction of a particular reference genome (e.g., human reference genome) or part of the genome has been analyzed. The denominator of the fraction can be a repeat-masked genome, and thus 100% can correspond to all of the reference genome minus the masked parts. A repeat-masked genome can refer to a genome in which sequence repeats are masked (e.g., sequence reads align to unmasked portions of the genome). Any parts of a genome can be masked, and thus one can focus on any particular part of a reference genome. Broad sequencing can refer to sequencing and analyzing at least 0.1% of the genome.

As used herein, the term "reference genome" refers to any particular known, sequenced or characterized genome, whether partial or complete, of any organism or virus that may be used to reference identified sequences from a subject. Exemplary reference genomes used for human subjects as well as many other organisms are provided in the on-line genome browser hosted by the National Center for Biotechnology Information ("NCBI") or the University of California, Santa Cruz (UCSC). A "genome" refers to the complete genetic information of an organism or virus, expressed in nucleic acid sequences. As used herein, a reference sequence or reference genome often is an assembled or partially assembled genomic sequence from an individual or multiple individuals. In some embodiments, a reference genome is an assembled or partially assembled genomic sequence from one or more human individuals. The reference genome can be viewed as a representative example of a species' set of genes. In some embodiments, a reference genome comprises sequences assigned to chromosomes. Exemplary human reference genomes include but are not limited to NCBI build 34 (UCSC equivalent: hg16), NCBI build 35 (UCSC equivalent: hg17), NCBI build 36.1 (UCSC equivalent: hg18), GRCh37 (UCSC equivalent: hg19), and GRCh38 (UCSC equivalent: hg38).

As used herein, the term "assay" refers to a technique for determining a property of a substance, e.g., a nucleic acid, a protein, a cell, a tissue, or an organ. An assay (e.g., a first assay or a second assay) can comprise a technique for determining the copy number variation of nucleic acids in a sample, the methylation status of nucleic acids in a sample, the fragment size distribution of nucleic acids in a sample, the mutational status of nucleic acids in a sample, or the fragmentation pattern of nucleic acids in a sample. Any assay known to a person having ordinary skill in the art can be used to detect any of the properties of nucleic acids mentioned herein. Properties of a nucleic acids can include a sequence, genomic identity, copy number, methylation state at one or more nucleotide positions, size of the nucleic acid, presence or absence of a mutation in the nucleic acid at one or more nucleotide positions, and pattern of fragmentation of a nucleic acid (e.g., the nucleotide position(s) at which a nucleic acid fragments). An assay or method can have a particular sensitivity and/or specificity, and their relative usefulness as a diagnostic tool can be measured using ROC-AUC statistics.

As used herein, the term "true positive" (TP) refers to a subject having a condition. "True positive" can refer to a subject that has a tumor, a cancer, a precancerous condition (e.g., a precancerous lesion), a localized or a metastasized cancer, or a non-malignant disease. "True positive" can refer to a subject having a condition, and is identified as having the condition by an assay or method of the present disclosure.

As used herein, the term "true negative" (TN) refers to a subject that does not have a condition or does not have a detectable condition. True negative can refer to a subject that does not have a disease or a detectable disease, such as a tumor, a cancer, a precancerous condition (e.g., a precancerous lesion), a localized or a metastasized cancer, a non-malignant disease, or a subject that is otherwise healthy. True negative can refer to a subject that does not have a condition or does not have a detectable condition, or is identified as not having the condition by an assay or method of the present disclosure.

As used herein, the term "sensitivity" or "true positive rate" (TPR) refers to the number of true positives divided by the sum of the number of true positives and false negatives (e.g., calculated by TP/(TP+FN)). Sensitivity can characterize the ability of an assay or method to correctly identify a proportion of the population that truly has a condition. For example, sensitivity can characterize the ability of a method to correctly identify the number of subjects within a population having cancer. In another example, sensitivity can characterize the ability of a method to correctly identify the one or more markers indicative of cancer.

As used herein, the term "specificity" or "true negative rate" (TNR) refers to the number of true negatives divided by the sum of the number of true negatives and false positives (e.g., calculated by TN/(TN+FP)). Specificity can characterize the ability of an assay or method to correctly identify a proportion of the population that truly does not have a condition. For example, specificity can characterize the ability of a method to correctly identify the number of subjects within a population not having cancer. In another example, specificity can characterize the ability of a method to correctly identify one or more markers indicative of cancer.

As used herein, the term "false positive" (FP) refers to a subject that does not have a condition. False positive can refer to a subject that does not have a tumor, a cancer, a precancerous condition (e.g., a precancerous lesion), a localized or a metastasized cancer, a non-malignant disease, or is otherwise healthy. The term false positive can refer to a subject that does not have a condition, but is identified as having the condition by an assay or method of the present disclosure.

As used herein, the term "false negative" (FN) refers to a subject that has a condition. False negative can refer to a subject that has a tumor, a cancer, a precancerous condition (e.g., a precancerous lesion), a localized or a metastasized cancer, or a non-malignant disease. The term false negative can refer to a subject that has a condition, but is identified as not having the condition by an assay or method of the present disclosure.

As used herein, the "negative predictive value" or "NPV" can be calculated by TN/(TN+FN) or the true negative fraction of all negative test results. Negative predictive value can be inherently impacted by the prevalence of a condition in a population and pre-test probability of the population intended to be tested. The term "positive predictive value" or "PPV" can be calculated by TP/(TP+FP) or the true positive fraction of all positive test results. PPV can be inherently impacted by the prevalence of a condition in a population and pre-test probability of the population intended to be tested. See, e.g., O'Marcaigh and Jacobson, 1993, "Estimating The Predictive Value of a Diagnostic Test, How to Prevent Misleading or Confusing Results," Clin. Ped. 32(8): 485-491, which is entirely incorporated herein by reference.

As used herein, the term "ROC" or "ROC curve," refers to a receiver operator characteristic curve. In some embodiments, a ROC curve is depicted as a graphical representation of the performance of a binary classifier system. For any given method, a ROC curve can be generated by plotting the sensitivity against the specificity at various threshold settings. In some embodiments, the sensitivity and specificity of a method for detecting the presence of a tumor in a subject is determined at various concentrations of tumor-derived DNA in the plasma sample of the subject. Furthermore, in some embodiments, provided at least one of three parameters (e.g., sensitivity, specificity, and the threshold setting), a ROC curve determines the value or expected value for any unknown parameter. The unknown parameter can be determined using a curve fitted to a ROC curve. For example, provided the concentration of tumor-derived DNA in a sample, the expected sensitivity and/or specificity of a test can be determined. The term "AUC" or "ROC-AUC" can refer to the area under a receiver operator characteristic curve. This metric can provide a measure of diagnostic utility of a method, taking into account both the sensitivity and specificity of the method. A ROC-AUC can range from 0.5 to 1.0, where a value closer to 0.5 can indicate a method has limited diagnostic utility (e.g., lower sensitivity and/or specificity) and a value closer to 1.0 indicates the method has greater diagnostic utility (e.g., higher sensitivity and/or specificity). See, e.g., Pepe et al., "Limitations of the Odds Ratio in Gauging the Performance of a Diagnostic, Prognostic, or Screening Marker," Am. J. Epidemiol 2004, 159 (9): 882-890, which is entirely incorporated herein by reference. Additional approaches for characterizing diagnostic utility include using likelihood functions, odds ratios, information theory, predictive values, calibration (including goodness-of-fit), and reclassification measurements. Examples of the approaches are summarized, e.g., in Cook, "Use and Misuse of the Receiver Operating Characteristic Curve in Risk Prediction," *Circulation* 2007, 115: 928-935, which is entirely incorporated herein by reference.

The term "classification" can refer to any number(s) or other characters(s) that are associated with a particular property of a sample. For example, a "+" symbol (or the word "positive") can signify that a sample is classified as having deletions or amplifications. In another example, the term "classification" can refer to an amount of tumor tissue in the subject and/or sample, a size of the tumor in the subject and/or sample, a stage of the tumor in the subject, a tumor load in the subject and/or sample, and presence of tumor metastasis in the subject. The classification can be binary (e.g., positive or negative) or have more levels of classification (e.g., a scale from 1 to 10 or 0 to 1). The terms "cutoff" and "threshold" can refer to predetermined numbers used in an operation. For example, a cutoff size can refer to a size above which fragments are excluded. A threshold value can be a value above or below which a particular classification applies. Either of these terms can be used in either of these contexts.

As used herein, the term "relative abundance" can refer to a ratio of a first amount of nucleic acid fragments having a particular characteristic (e.g., a specified length, ending at one or more specified coordinates/ending positions, or aligning to a particular region of the genome) to a second amount nucleic acid fragments having a particular characteristic (e.g., a specified length, ending at one or more specified coordinates/ending positions, or aligning to a particular region of the genome). In one example, relative abundance may refer to a ratio of the number of DNA fragments ending at a first set of genomic positions to the number of DNA fragments ending at a second set of genomic positions. In some aspects, a "relative abundance" can be a type of separation value that relates an amount (one value) of cell-free DNA molecules ending within one window of genomic position to an amount (other value) of cell-free DNA molecules ending within another window of genomic positions. The two windows can overlap, but can be of different sizes. In other implementations, the two windows cannot overlap. Further, the windows can be of a width of one nucleotide, and therefore be equivalent to one genomic position.

As used herein the term "untrained classifier" refers to a classifier that has not been trained on a target dataset. For instance, consider the case of a target dataset that is a value training set discussed in further detail below. The value training set is applied as collective input to an untrained classifier, in conjunction with the cancer class of each respective reference subject represented by the value training set, to train the untrained classifier on cancer class thereby obtaining a trained classifier. The target dataset may represent raw or normalized measurements from subjects represented by the target dataset, principal components derived from such raw or normalized measurements, regression coefficients derived from the raw or normalized measurements (or the principal components of the raw or normalized measurements), or any other form of data from subjects with known disease class that is used to train classifiers in the art. In general, a target dataset is the dataset that is used to directly train an untrained classifier. However, it will be appreciated that the term "untrained classifier" does not exclude the possibility that transfer learning techniques are used in such training of the untrained classifier. For instance, Fernandes et al., 2017, "Transfer Learning with Partial Observability Applied to Cervical Cancer Screening," Pattern Recognition and Image Analysis: 8$^{th}$ Iberian Conference Proceedings, 243-250, which is hereby incorporated by reference, provides non-limiting examples of such transfer learning. In the case where transfer learning is used, the untrained classifier described above is provided with additional data over and beyond that of the disease class labeled target dataset. That is, in non-limiting examples of transfer learning embodiments, the untrained classifier receives (i) the disease class labeled target training dataset (e.g., the value training set with each respective reference subject represented by the value training set labeled by cancer class) and (ii) additional data. Typically, this additional data is in the form of coefficients (e.g. regression coefficients) that were learned from another, auxiliary training dataset. More specifically, in some embodiments, the target training dataset is in the form of a first two-dimensional matrix, with one axis representing patients, and the other axis representing some property of respective patients, such as bin counts across all or a portion of the genome of respective patients in the target training set. Application of pattern classification techniques to the auxiliary training dataset yields a second two-dimensional matrix, where one axis is the learned coefficients and the other axis is the property of respective patients in the auxiliary training dataset, such as bin counts across all or a portion of respective patients in the first auxiliary training dataset. Matrix multiplication of the first and second matrices by their common dimension (e.g. bin counts) yields a third matrix of auxiliary data that can be applied, in addition to the first matrix to the untrained classifier. One reason it might be useful to train the untrained classifier using this additional information from an auxiliary training dataset is a paucity of subjects in one or more categories in the target dataset (e.g., the value training set). This is a particular issue for many healthcare datasets, where there may not be a large number of patients who have a particular disease or who are at a particular stage of a given disease. Making use of as much of the available data as possible can increase the accuracy of classifications and thus improve patient results. Thus, in the case where an auxiliary training dataset is used to train an untrained classifier beyond just the target training dataset (e.g. value training set), the auxiliary training dataset is subjected to classification techniques (e.g., principal component analysis followed by logistic regression) to learn coefficients (e.g., regression coefficients) that discriminate disease class based on the auxiliary training dataset. Such coefficients can be multiplied against a first instance of the target training dataset (e.g., the value training set) and inputted into the untrained classifier in conjunction with the target training dataset (e.g., the value training set) as collective input, in conjunction with the disease class (e.g. cancer class) of each respective reference subject in the target training dataset. As one of skill in the art will appreciate, such transfer learning can be applied with or without any form of dimension reduction technique on the auxiliary training dataset or the target training dataset. For instance, the auxiliary training dataset (from which coefficients are learned and used as input to the untrained classifier in addition to the target training dataset) can be subjected to a dimension reduction technique prior to regression (or other form of label based classification) to learn the coefficients that are applied to the target training dataset. Alternatively, no dimension reduction other than regression or some other form of pattern classification is used in some embodiments to learn such coefficients from the auxiliary training dataset prior to applying the coefficients to an instance of the target training dataset (e.g., through matrix multiplication where one matrix is the coefficients learned from the auxiliary training dataset and the second matrix is an instance of the target training dataset). Moreover, in some embodiments, rather than applying the coefficients learned from the auxiliary training dataset to the target training dataset, such coefficients are applied (e.g., by matrix multiplication based on a common axis of bin counts) to the bin count data that was collected from the first plurality of reference subjects that was used as a basis for forming the value training set as disclosed herein. Moreover, while a description of a single auxiliary training dataset has been disclosed, it will be appreciated that there is no limit on the number of auxiliary training datasets that may be used to complement the target training dataset in training the untrained classifier in the present disclosure. For instance, in some embodiments, two or more auxiliary training datasets, three or more auxiliary training datasets, four or more auxiliary training datasets or five or more auxiliary training datasets are used to complement the target training dataset through transfer learning, where each such auxiliary dataset is different than the target training dataset. Any manner of transfer learning may be used in such embodiments. For instance, consider the case where there is a first auxiliary training dataset and a second auxiliary training dataset in addition to the target training dataset (where, as before the target training dataset is any dataset that is directly used to train the untrained classifier). The coefficients learned from the first auxiliary training dataset (by application of a classifier such as regression to the first auxiliary training dataset) may be applied to the second auxiliary training dataset using transfer learning techniques (e.g., the above described two-dimensional matrix multiplication), which in turn may result in a trained intermediate classifier whose coefficients are then applied to the target training dataset and this, in conjunction with the target training dataset itself, is applied to the untrained classifier. Alternatively, a first set of coefficients learned from the first auxiliary training dataset (by application of a classifier such as regression to the first auxiliary training dataset) and a second set of coefficients learned from the second auxiliary training dataset (by application of a classifier such as regression to the second auxiliary training dataset) may each independently be applied to a separate instance of the target training dataset (e.g., by separate independent matrix multiplications) and both such applications of the coefficients to separate instances of the target training dataset in conjunction with the target training dataset itself (or some reduced form of the target training dataset such as principal components learned from the target training set) may then be applied to the untrained classifier in order to train the untrained classifier. In either example, knowledge regarding disease (e.g., cancer) classification derived from the first and second auxiliary training datasets is used, in conjunction with the disease labeled target training dataset (e.g., the value training dataset), to train the untrained classifier.

Several aspects are described below with reference to example applications for illustration. It should be understood that numerous specific details, relationships, and methods are set forth to provide a full understanding of the features described herein. One having ordinary skill in the relevant art, however, will readily recognize that the features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are required to implement a methodology in accordance with the features described herein.

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

The implementations described herein provide various technical solutions for screening for a condition. A first assay quantifies an amount of a feature of cell-free nucleic acid in a first biological sample of a test subject. A second assay generate sequence reads from the cell-free nucleic acid in a second biological sample of the test subject. An amount of these sequence reads aligning to the pathogen reference genome is thresholded by an amount of sequence reads associated with a predetermined percentile of a distribution. Each respective subject in a cohort of subjects not having the condition contributes to the distribution an amount of sequence reads aligning to the pathogen reference genome. This results in a scaled amount of the sequence reads from the test subject. Screening for the condition is performed based on the first and second assays, making use of the scaled amount of the test subject sequence reads, in which the test subject is deemed to have the condition when either the first or second assay indicates the subject has the condition.

Example System Embodiments

Figure 1:
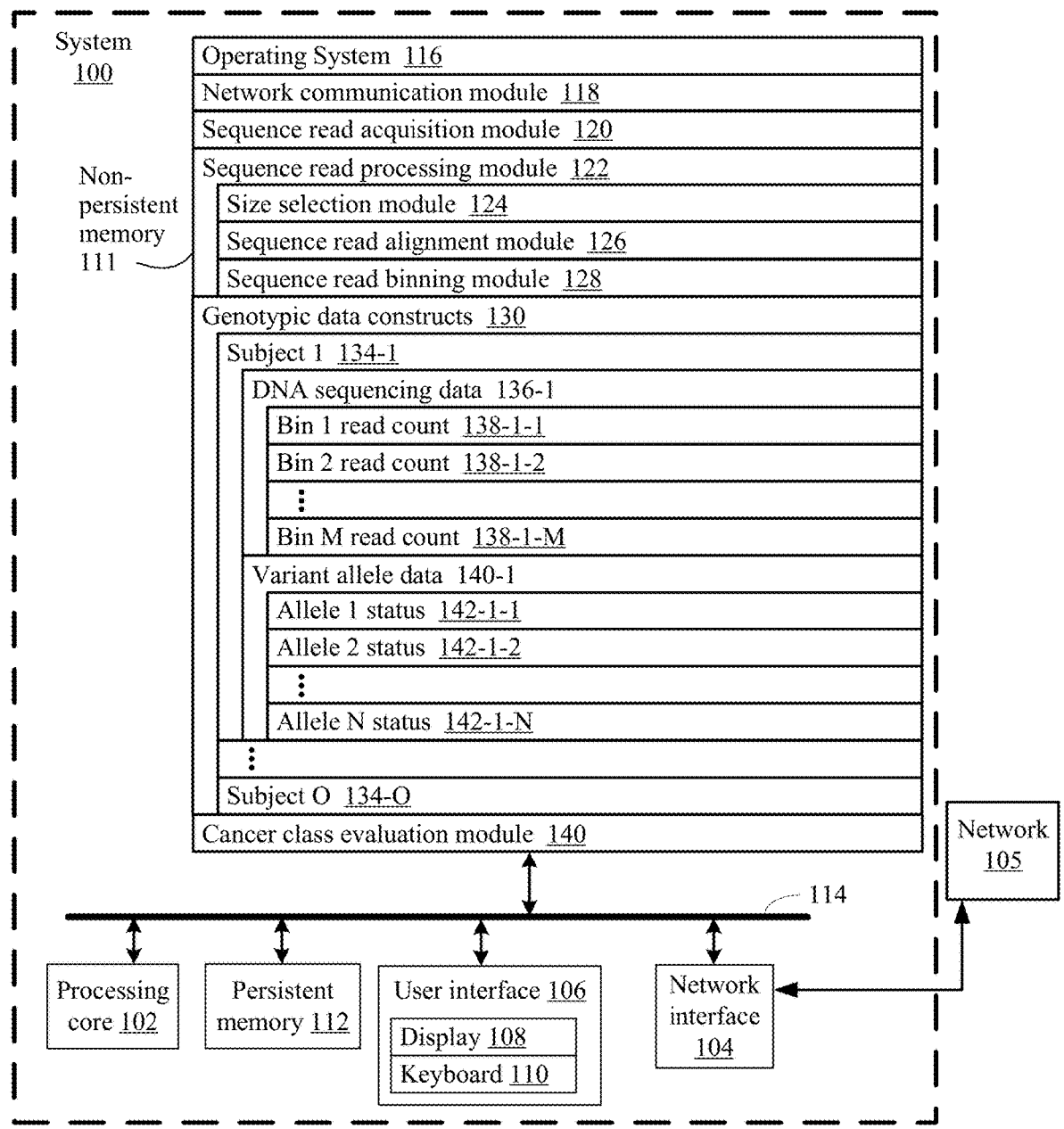
FIG. 1 illustrates a block diagram of an example computing device, in accordance with various embodiments of the present disclosure.

Details of an example system are described in relation to FIG. 1. FIG. 1 is a block diagram illustrating a system 100 for using size-selected sequence reads of cell-free DNA molecules for the classification of cancer in a subject, in accordance with some implementations. Device 100, in some implementations, includes one or more processing units CPU(s) 102 (also referred to as processors or processing cores), one or more network interfaces 104, a user interface 106, a non-persistent memory 111, a persistent memory 112, and one or more communication buses 114 for interconnecting these components. The one or more communication buses 114 optionally include circuitry (sometimes called a chipset) that interconnects and controls communications between system components. The non-persistent memory 111 typically includes high-speed random access memory, such as DRAM, SRAM, DDR RAM, ROM, EEPROM, flash memory, whereas the persistent memory 112 typically includes CD-ROM, digital versatile disks (DVD) or other optical storage, magnetic cassettes, magnetic tape, magnetic disk storage or other magnetic storage devices, magnetic disk storage devices, optical disk storage devices, flash memory devices, or other non-volatile solid state storage devices. The persistent memory 112 optionally includes one or more storage devices remotely located from the CPU(s) 102. The persistent memory 112, and the non-volatile memory device(s) within the non-persistent memory 112, comprise non-transitory computer readable storage medium. In some implementations, the non-persistent memory 111 or alternatively the non-transitory computer readable storage medium stores the following programs, modules and data structures, or a subset thereof, sometimes in conjunction with the persistent memory 112:

- an optional operating system 116, which includes procedures for handling various basic system services and for performing hardware dependent tasks;
- an optional network communication module (or instructions) 118 for connecting the system 100 with other devices and/or a communication network 105;
- an optional sequence read acquisition module 120 for sequencing nucleic acids from a biological sample from a subject;
- an optional sequence read processing module 122 for processing sequence reads, e.g., acquired via sequence read acquisition module 120, including one or more of:
  - a size selection module 124 for selecting sequence reads having a desired length, e.g., sequence reads of cell-free DNA molecules that are shorter than a threshold length, to enrich for sequence reads of cancer-derived cell-free DNA molecules,
  - a sequence read alignment module 126 for aligning sequence reads, e.g., acquired via sequence read acquisition module 120, to a reference genome, and
  - a sequence read binning module 128, for assigning sequence reads to one of a plurality of genomic location bins across a reference genome;
- a genotypic data construct data store 130 including genotypic data from one or more subject 134, where the genotypic data includes:
  - DNA sequencing data 136, e.g., acquired by sequence read acquisition module 120 and/or processed by sequence read processing module 122, where the sequencing data includes, for example, bin counts 138 for a plurality of genomic location bins assigned across a reference genome, and optionally, other genomic data about the subject, e.g., variant allele data 140 which includes the status of one or more alleles 142 in the subject; and a cancer class evaluation module 140 for classifying a cancer class of an individual based on the genotypic data 134 of the subject.

In various implementations, one or more of the above identified elements are stored in one or more of the previously mentioned memory devices, and correspond to a set of instructions for performing a function described above. The above identified modules, data, or programs (e.g., sets of instructions) need not be implemented as separate software programs, procedures, datasets, or modules, and thus various subsets of these modules and data may be combined or otherwise re-arranged in various implementations. In some implementations, the non-persistent memory 111 optionally stores a subset of the modules and data structures identified above. Furthermore, in some embodiments, the memory stores additional modules and data structures not described above. In some embodiments, one or more of the above identified elements is stored in a computer system, other than that of system 100, that is addressable by system 100 so that system 100 may retrieve all or a portion of such data when needed.

Although FIG. 1 depicts a "system 100," the figure is intended more as functional description of the various features which may be present in computer systems than as a structural schematic of the implementations described herein. In practice, and as recognized by those of ordinary skill in the art, items shown separately could be combined and some items could be separated. Moreover, although FIG. 1 depicts certain data and modules in non-persistent memory 111, some or all of these data and modules may be in persistent memory 112.

While a system in accordance with the present disclosure has been disclosed with reference to FIG. 1, methods in accordance with the present disclosure are now detailed. It will be appreciated that any of the disclosed methods can make use of any of the assays or algorithms disclosed in U.S. Pat. No. 9,121,069 entitled "Diagnosing cancer using genomic sequencing;" US Pat. Pub. No. 2017/0218450A1 entitled "Detecting genetic aberrations associated with cancer using genomic sequencing;" U.S. Pat. No. 9,965,585 entitled "Detection of genetic or molecular aberrations associated with cancer;" U.S. Pat. No. 9,892,230 entitled "Size-based analysis of fetal or tumor DNA fraction in plasma," US Pat. Pub. No. 2016/0201142A1 entitled "Using size and number aberrations in plasma dna for detecting cancer;" US App. No. 62/642,461 entitled "Method and system for selecting, managing and analyzing data of high dimensionality;" U.S. App. No. 62/679,746 entitled "convolutional neural network systems and methods for data classification;" U.S. App. No. 62/777,693 entitled "Systems and Methods for Classifying Patients with Respect to Multiple Cancer Classes;" the disclosures of which are incorporated herein by reference, in their entireties, for all purposes, in order to determine a cancer condition in a test subject or a likelihood that the subject has the cancer condition.

Example Classification Models.

In some aspects, the disclosed methods can work in conjunction with cancer classification models. For example, a machine learning or deep learning model (e.g., a disease classifier) can be used to determine a disease state based on values of one or more features determined from one or more cell-free DNA molecules or sequence reads (derived from one or more cfDNA molecules). In various embodiments, the output of the machine learning or deep learning model is a predictive score or probability of a disease state (e.g., a predictive cancer score). Therefore, the machine learning or deep learning model generates a disease state classification based on the predictive score or probability.

In some embodiments, the machine-learned model includes a logistic regression classifier. In other embodiments, the machine learning or deep learning model can be one of a decision tree, an ensemble (e.g., bagging, boosting, random forest), gradient boosting machine, linear regression, Naïve Bayes, or a neural network. The disease state model includes learned weights for the features that are adjusted during training. The term "weights" is used generically here to represent the learned quantity associated with any given feature of a model, regardless of which particular machine learning technique is used. In some embodiments, a cancer indicator score is determined by inputting values for features derived from one or more DNA sequences (or DNA sequence reads thereof) into a machine learning or deep learning model.

During training, training data is processed to generate values for features that are used to train the weights of the disease state model. As an example, training data can include cfDNA data, cancer gDNA, and/or WBC gDNA data obtained from training samples, as well as an output label. For example, the output label can be an indication as to whether the individual is known to have a specific disease (e.g., known to have cancer) or known to be healthy (i.e., devoid of a disease). In other embodiments, the model can be used to determine a disease type, or tissue of origin (e.g., cancer tissue of origin), or an indication of a severity of the disease (e.g., cancer stage) and generate an output label therefor. Depending on the particular embodiment, the disease state model receives the values for one or more of the features determine from a DNA assay used for detection and quantification of a cfDNA molecule or sequence derived therefrom, and computational analyses relevant to the model to be trained. In one embodiment, the one or more features comprise a quantity of one or more cfDNA molecules or sequence reads derived therefrom. Depending on the differences between the scores output by the model-in-training and the output labels of the training data, the weights of the predictive cancer model are optimized to enable the disease state model to make more accurate predictions. In various embodiments, a disease state model may be a non-parametric model (e.g., k-nearest neighbors) and therefore, the predictive cancer model can be trained to make more accurately make predictions without having to optimize parameters.

Example Method Embodiments

Now that details of a system 100 for using cell-free DNA fragment lengths in cancer detection and diagnostics has been disclosed, details regarding the processes and features of the system, in accordance with various embodiments of the present disclosure, are disclosed with reference to FIGS. 2 through 4. In some embodiments, such processes and features of the system are carried out by the various modules described in example system 100, e.g., sequence read acquisition module 122, size selection module 124, sequence read alignment module 126, sequence read binning module 128, and cancer class evaluation module 140, as illustrated in FIG. 1.

The embodiments described below relate to analyses performed using sequence reads of cell-free DNA fragments obtained from a biological sample, e.g., a blood sample. Generally, these embodiments are independent and, thus, not reliant upon any particular sequencing methodologies. However, in some embodiments, the methods described below include one or more steps of generating the sequence reads used for the analysis, and/or specify certain sequencing parameters that are advantageous for the particular type of analysis being performed.

Additionally, although the methods and systems described herein refer to the use of sequence reads for determining various characteristics of a test subject, e.g., relative copy number for various genomic loci, the skilled artisan will appreciate that, in many embodiments, raw sequence reads generated for nucleic acids in a biological sample are collapsed into nucleic acid fragment sequences prior to extracting characteristics (e.g., relative copy number) from the sequencing data. Collapsing of the raw sequence reads into nucleic acid fragment sequences provides several advantages during the subsequence characteristic extraction. For example, because next generation sequencing techniques routinely generate hundreds or thousands of sequence reads for each unique nucleic acid fragment in the reaction, the raw sequencing data includes several orders of magnitude more data than a set of collapsed nucleic acid fragment sequences, because each unique nucleic acid fragment sequenced is only represented by a single nucleic acid fragment sequence. This, in turn, reduces the computational resources required for the characteristic extraction several-fold (or more) accordingly. Further, the use of nucleic acid fragment sequences eliminates sequencing biases caused by non-uniform sequencing of the unique nucleic acid molecules. For instance, where one unique nucleic acid fragment is sequenced with greater efficiency than the sequencing of a second unique nucleic acid fragment, use of the raw sequence reads without accounting for this non-uniform sequencing would lead to the false conclusion that the locus represented by the first unique nucleic acid fragment is represented more frequently in the biological sample than the locus represented by the second unique nucleic acid fragment. Accordingly, in the methods and systems described below, the term "sequence reads" could be replaced with the term "nucleic acid fragment sequences." However, even when the nucleic acid fragment sequences are used to extract characteristics of the biological sample from the sequencing data, the raw sequencing reads are still utilized during generation of the nucleic acid fragment sequences.

Methods for sequencing are well known in the art and include, without limitations, next generation sequencing (NGS) techniques including synthesis technology (Illumina), pyrosequencing (454 Life Sciences), ion semiconductor technology (Ion Torrent sequencing), single-molecule real-time sequencing (Pacific Biosciences), sequencing by ligation (SOLiD sequencing), nanopore sequencing (Oxford Nanopore Technologies), or paired-end sequencing. In some embodiments, massively parallel sequencing is performed using sequencing-by-synthesis with reversible dye terminators. Described below, with reference to FIGS. 2A, 2B, and 24, are examples of methods used for generating sequencing data from cell-free DNA fragments that is useful in the methods of classifying a cancer condition described herein.

Figure 2B:
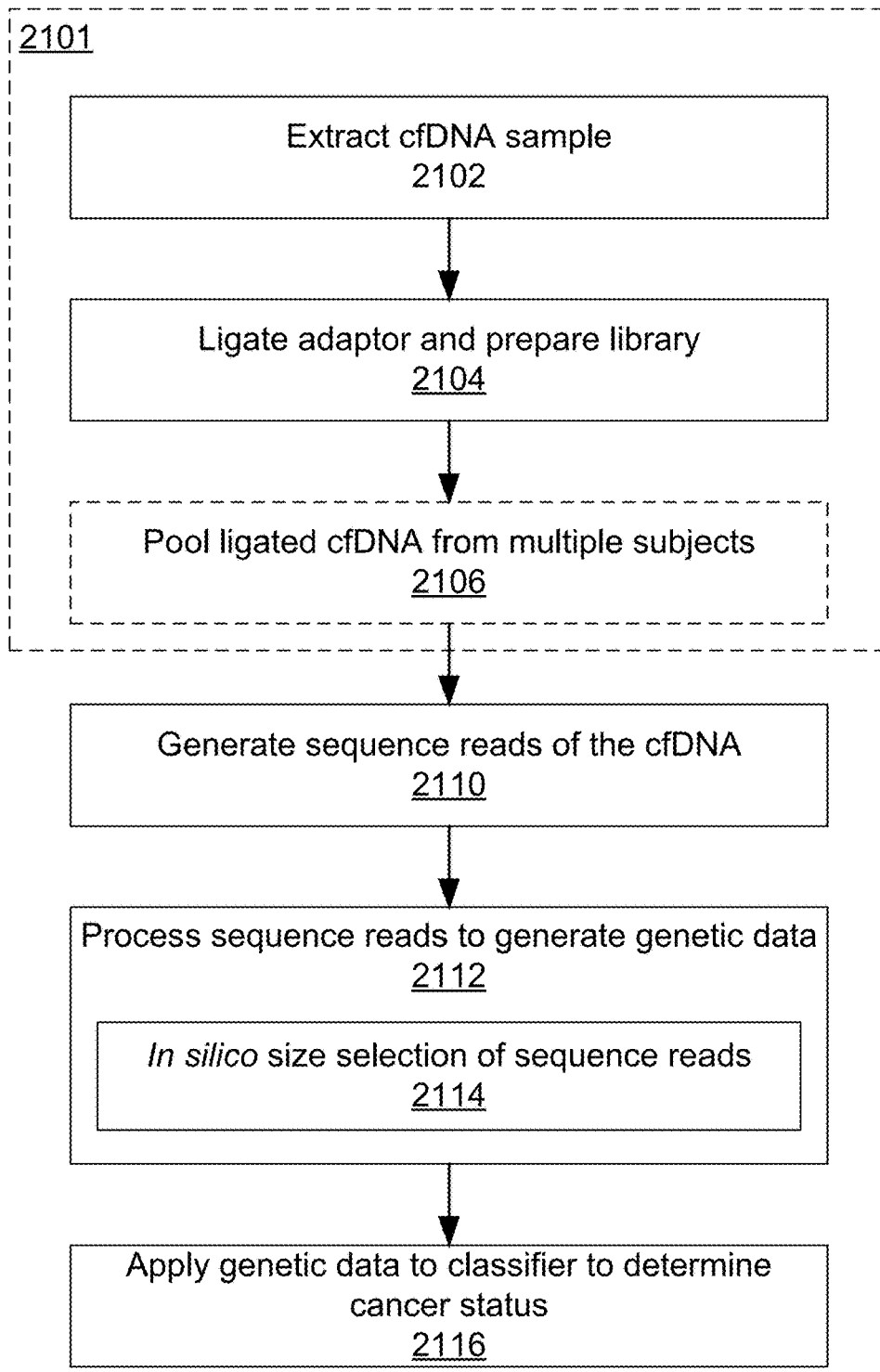
FIG. 2B provides a flow chart for a method of determining a cancer status of a subject using in silico size-selected sequence reads of cell-free DNA from a biological sample of the subject, in accordance with various embodiments of the present disclosure.

FIG. 2A is flowchart of a method 2000 for determining a cancer status of a subject using in vitro size-selected cell-free DNA from a biological sample of the subject, in accordance with various embodiments of the present disclosure. Within method 2000 is sub-method 2001 for preparing a nucleic acid sample for sequencing, according to one embodiment. Similarly, FIG. 2B is a flowchart of a method 2100 for determining a cancer status of a subject using in silico size-selected sequence reads of cell-free DNA from a biological sample of the subject, in accordance with various embodiments of the present disclosure. Within method 2100 is sub-method 2101 for preparing a nucleic acid sample for sequencing, according to one embodiment. Methods 2000 and 2100 include, but are not limited to, the steps shown in FIGS. 2A and 2b, respectively. For example, any step of method 2000 or 2100 may include a quantitation sub-step for quality control or other laboratory assay procedures known to one skilled in the art.

In blocks 2002 and 2102, a nucleic acid sample (DNA or RNA) is extracted from a subject. The sample may be any subset of the human genome, including the whole genome. The sample may be extracted from a subject known to have or suspected of having cancer. The sample may include blood, plasma, serum, urine, fecal, saliva, other types of bodily fluids, or any combination thereof. In some embodiments, methods for drawing a blood sample (e.g., syringe or finger prick) may be less invasive than procedures for obtaining a tissue biopsy, which may require surgery. The extracted sample may include cfDNA and/or ctDNA. For healthy individuals, the human body may naturally clear out cfDNA and other cellular debris. If a subject has a cancer or disease, ctDNA in an extracted sample may be present at a detectable level for diagnosis.

In blocks 2004 and 2104, a sequencing library is prepared. During library preparation, unique molecular identifiers (UMIs) are added to the nucleic acid molecules (e.g., DNA molecules) through adapter ligation. In some embodiments, the UMIs are short nucleic acid sequences (e.g., 4-10 base pairs) that are added to ends of DNA fragments during adapter ligation. In some embodiments, UMIs are degenerate base pairs that serve as a unique tag that can be used to identify sequence reads originating from a specific DNA fragment. In some embodiments, e.g., when multiplex sequencing will be used to sequence cfDNA from a plurality of subjects in a single sequencing reaction, a patient-specific index is also added to the nucleic acid molecules. In some embodiments, the patient specific index is a short nucleic acid sequence (e.g., 3-20 nucleotides) that are added to ends of DNA fragments during library construction, that serve as a unique tag that can be used to identify sequence reads originating from a specific patient sample. During PCR amplification following adapter ligation, the UMIs are replicated along with the attached DNA fragment. This provides a way to identify sequence reads that came from the same original fragment in downstream analysis.

In blocks 2006 and 2106, cfDNA sequencing libraries, e.g., prepared according to block 2004, from multiple subjects are optionally pooled together. Several advantages are achieved by pooling samples together for next generation sequencing. First, because of the high-throughput capacity of next generation sequencers, large amounts of template DNA are required for a single reaction. By pooling cfDNA sequencing libraries together, less cfDNA is required from each patient for the sequencing reaction. Second, because of the cost of a single sequencing reaction is essentially fixed, pooling cfDNA sequencing libraries, and sequencing them together, reduces the cost of sequencing per cfDNA library by a factor of the number of libraries pooled together.

In block 2008, which is specific to method 2000, cfDNA molecules in the pooled sample are size selected, e.g., to remove molecules originating from cfDNA fragments that are longer than a threshold length (e.g., where the threshold length is less than 160 nucleotides). Methods for size selecting nucleic acid fragments are known in the art, e.g., agarose electrophoresis. When size selecting the pooled cfDNA sequencing library, the selected lengths are determined based on the sum of the desired range of lengths of the original cfDNA fragment (w) and the length of the adaptors (x, e.g., containing UMIs, primer sites, patient-specific indices, etc.), e.g., w+x.

In blocks 2010 and 2110, sequence reads are generated from the size-selected cfDNA pools. Sequencing data may be acquired by known means in the art. For example, method 2000 may include next generation sequencing (NGS) techniques including synthesis technology (Illumina), pyrosequencing (454 Life Sciences), ion semiconductor technology (Ion Torrent sequencing), single-molecule real-time sequencing (Pacific Biosciences), sequencing by ligation (SOLiD sequencing), nanopore sequencing (Oxford Nanopore Technologies), or paired-end sequencing. In some embodiments, massively parallel sequencing is performed using sequencing-by-synthesis with reversible dye terminators.

In blocks 2012 and 2112, the sequence reads generated in blocks 2010 and 2110 are processed to generate genetic data for each subject. In some embodiments, where the sequencing reaction is a multiplex sequencing reaction of cfDNA from more than one sample and/or subject, processing includes de-multiplexing the data, to identify sequence reads from each sample and/or subject, based on identification of the unique UMI sequences. In some embodiments, processing includes aligning the sequence reads to a reference genome using known methods in the art to determine alignment position information. The alignment position information may indicate a beginning position and an end position of a region in the reference genome that corresponds to a beginning nucleotide base and end nucleotide base of a given sequence read. Alignment position information may also include sequence read length, which can be determined from the beginning position and end position. A region in the reference genome may be associated with a gene or a segment of a gene. In some embodiments, processing includes identifying one or more types of features of the cfDNA from the sequence reads. Features that may be extracted from the sequence reads include, but are not limited to, positions of the cfDNA fragments in the genome of the subject (e.g., absolute position or relative position within a segment of the genome), bin counts for segments of the genome (e.g., the number of sequences representing each segment in a plurality of segments of the genome), lengths of the cfDNA fragments (e.g., derived from the positions of the beginning and ending nucleotide bases in the reference genome), the presence of variant alleles (e.g., determined based on a comparison with the sequence a reference genome), allele fractions for variant alleles, methylation statuses of genomic locations, and linear and/or non-linear combinations of various features.

In various embodiments, a sequence read is comprised of a read pair denoted as $R_1$ and $R_2$. For example, the first read $R_1$ may be sequenced from a first end of a nucleic acid fragment whereas the second read $R_2$ may be sequenced from the second end of the nucleic acid fragment. Therefore, nucleotide base pairs of the first read $R_1$ and second read $R_2$ may be aligned consistently (e.g., in opposite orientations) with nucleotide bases of the reference genome. Alignment position information derived from the read pair $R_1$ and $R_2$ may include a beginning position in the reference genome that corresponds to an end of a first read (e.g., $R_1$) and an end position in the reference genome that corresponds to an end of a second read (e.g., $R_2$). In other words, the beginning position and end position in the reference genome represent the likely location within the reference genome to which the nucleic acid fragment corresponds. An output file having SAM (sequence alignment map) format or BAM (binary) format may be generated and output for further analysis.

In some embodiments, as represented in block 2114 which is specific to method 2100, processing of the sequence reads includes filtering the sequence reads to exclude sequence reads from cfDNA molecules that are longer than a threshold length, e.g., where the threshold length is less than 160 nucleotides. In some embodiments, this is accomplished by determining the length of a cfDNA corresponding to one or more sequence read, e.g., based on the positions of the beginning and ending nucleotide bases in the reference genome, and selecting only those sequence reads corresponding to cfDNA fragments with lengths falling within a desired range of lengths, such that the selected subset of sequence reads is enriched for sequence reads corresponding to cfDNA fragments derived from a cancer cell.

In blocks 2016 and 2116, features extracted from the sequencing data are applied to a classifier trained to determine one or more cancer status of the subject. As described herein, many classification methods are known in the art. Generally, the classifier is trained against one or more training data sets containing feature information from a plurality of subjects with a known cancer status, e.g., a cancer or non-cancer diagnosis, a type of cancer, a stage of cancer, a treatment response for a particular therapy, a cancer prognosis, and/or an expected survival time.

Having generally described methods 2000 and 2100 for determining a cancer status, specific processes and features of such methods are described with reference to methods 3000 and 4000, in accordance with various embodiments of the present disclosure. In some embodiments, such processes and features of the system are carried out by the various modules described in example system 100, e.g., sequence read acquisition module 122, size selection module 124, sequence read alignment module 126, sequence read binning module 128, and cancer class evaluation module 140, as illustrated in FIG. 1.

FIGS. 3A-3G are flow diagrams illustrating a method 3000 of determining a cancer class of a subject. Method 3000 is performed at a computer system (e.g., computer system 100 in FIG. 1) having one or more processors, and memory storing one or more programs for execution by the one or more processors for segmenting all of a portion of a reference genome for the species of the subject. Some operations in method 3000 are, optionally, combined and/or the order of some operations is, optionally, changed.

Method 3000 includes obtaining (3002) a first plurality of sequence reads, in electronic form, from a biological sample of the subject. The biological sample includes a first plurality of cell-free DNA molecules including respective DNA molecules that are longer than a first threshold length, where the first threshold length is less than 160 nucleotides. The first plurality of sequence reads excludes sequence reads of cell-free DNA molecules in the first plurality of cell-free DNA molecules longer than the first threshold length. Thus, the first plurality of sequence reads represents a reduced dimension space for the sequences of the first plurality of cell-free DNA molecules. Analysis of this reduced set of sequence reads reduces the computational burden of processing the sequencing data, because fewer calculations are required, thereby reducing the time required and improving the efficiency of the computer system performing the analysis.

As described above, it is known that mono- and di-nucleosomes fragmented from the genomes of non-cancerous somatic cells, hematopoietic cells (e.g., white blood cells), and (when the subject has cancer) cancerous cells. Thus, in some embodiments, the cell-free DNA molecules in the sample originate from at least non-cancerous somatic cells and hematopoietic cells (e.g., white blood cells). In some embodiments, sample also includes cell-free DNA molecules originating from cancerous cells. In some embodiments, it is unknown whether the subject has cancer and, thus, whether cell-free DNA originating from cancerous cells in present in the sample prior to analysis. Accordingly, in some embodiments, the subject has not been diagnosed as having cancer (3004). In some embodiments, the subject has already been diagnosed with cancer and, accordingly, it is known that the cell-free DNA originating from cancerous cells is present in the sample prior to analysis. In some embodiments, the subject is a human (3002).

In some embodiments, the biological sample includes blood, whole blood, plasma, serum, urine, cerebrospinal fluid, fecal material, saliva, sweat, tears, pleural fluid, pericardial fluid, or peritoneal fluid of the subject (3008). In some embodiments, the biological sample is a blood sample (3010), e.g., a whole-blood sample, a blood serum sample, or a blood plasma sample. In some embodiments, the biological sample is a blood plasma sample (3012). In some embodiments, the blood sample is a whole blood sample, and prior to generating the plurality of sequence reads from the whole blood sample, white blood cells are removed from the whole blood sample. In some embodiments, the white blood cells are collected as a second type of sample, e.g., according to a buffy coat extraction method, from which additional sequencing data may or may not be obtained. Methods for buffy coat extraction of white blood cells are known in the art, for example, as described in U.S. Provisional Application No. 62/679,347, filed on Jun. 1, 2018, the content of which is incorporated herein by reference, in its entirety, for all purposes. In some embodiments, the method further includes obtaining a second plurality of sequence reads in electronic form of genomic DNA from the white blood cells removed from the whole blood sample. In some embodiments, the second plurality of sequence reads is used to identify allele variants arising from clonal hematopoiesis, as opposed to germline allele variants and/or allele variants arising from a cancer in the subject.

Figure 5:
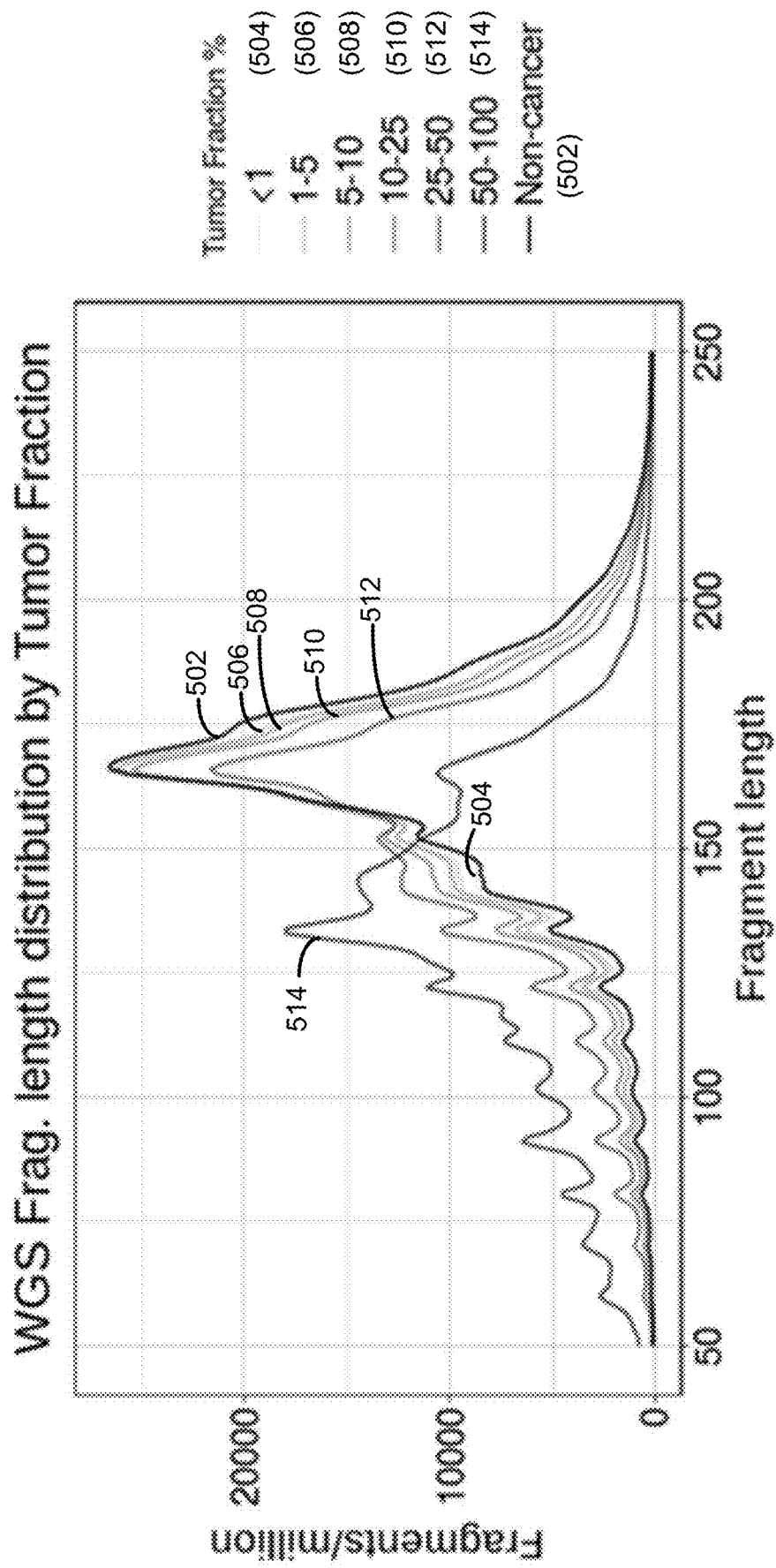
FIG. 5 illustrates the average distributions of cell-free DNA fragments lengths from subjects plotted as a function of the tumor fraction of the subject. Data for the 50-100% tumor fraction cohort was derived from a single sample from a subject with metastatic cancer.
Figure 6:
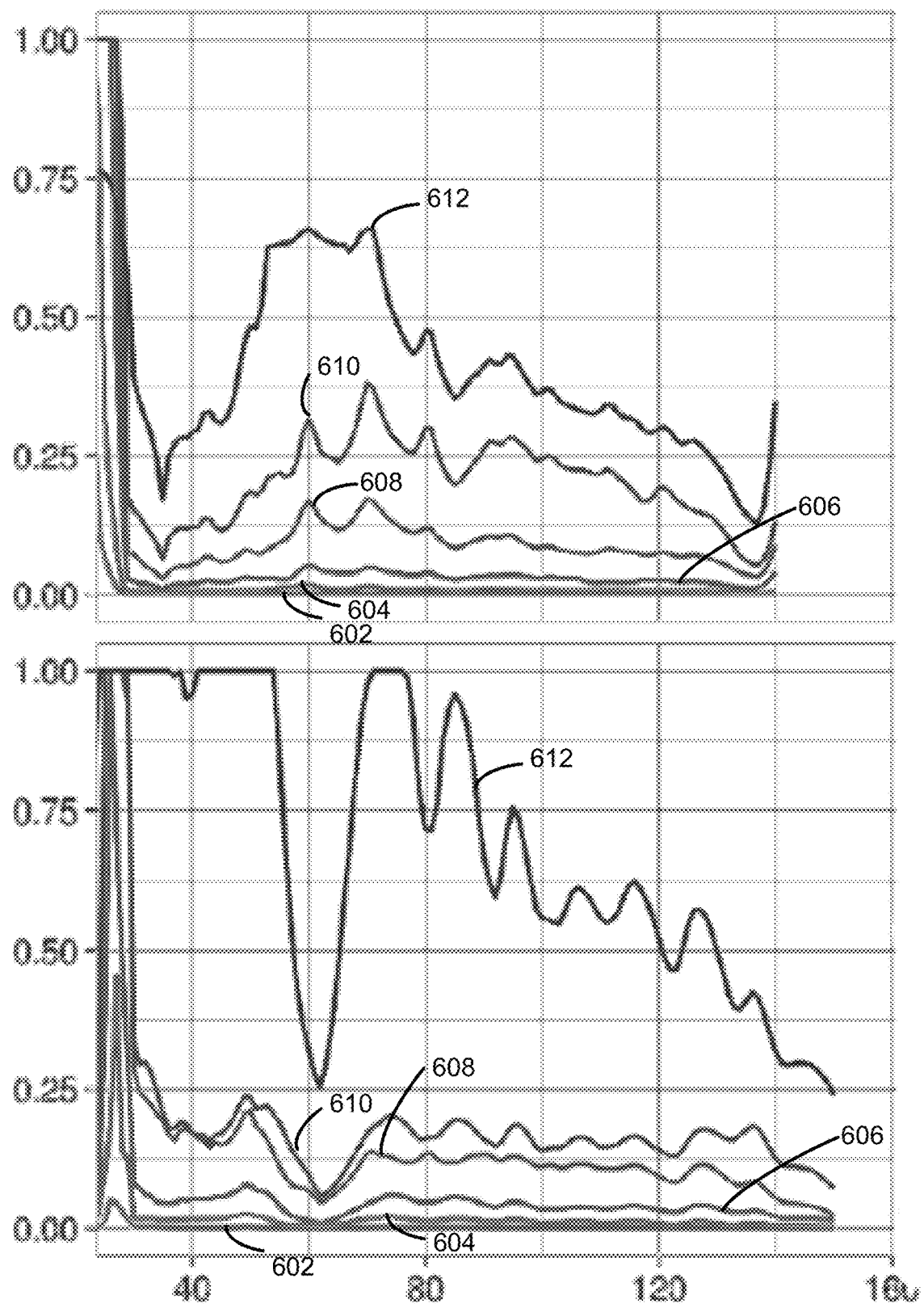
FIG. 6 illustrates a probabilistic model of cancer-origin as a function of cell-free DNA fragment length across various tumor fractions in samples that were size-selected for sequence reads from cfDNA fragments of from 30-140 nucleotides (top panel) or 30-150 nucleotides (bottom panel) (602≤0.005%; 604≤0.01%; 606≤0.05%; 608≤0.1%; 610≤0.2%; 612≤0.5).

Generally, the threshold length is set so as to increase the percentage of sequence reads that are generated for cfDNA fragments originating from cancer cells, as opposed to cfDNA fragments originating from somatic or hematopoietic cells. For instance, as can be seen by the shifting of cfDNA fragment length distribution as a function of tumor fraction in FIG. 5, cfDNA fragments originating from cancer cells have, on average, shorter lengths than cfDNA fragments originating from somatic cells or hematopoietic cells. Thus, as shown in FIG. 6, the probability of a given fragment being derived from a cancer cell increases as the size of the fragment decreases. Accordingly, in some embodiments, the first threshold length is set to a value of less than 160 nucleotides. In some embodiments, the first threshold length is 150 nucleotides or less (3014). In some embodiments, the first threshold length is 140 nucleotides or less (3016). In some embodiments, the first threshold length is 130 nucleotides or less (3018). In some embodiments, the first threshold length is 159, 158, 157, 156, 155, 154, 153, 152, 151, 150, 149, 148, 147, 146, 145, 144, 143, 142, 141, 140, 139, 138, 137, 136, 135, 134, 133, 132, 131, 130, 129, 128, 127, 126, 125, or fewer nucleotides. In one embodiment, the first threshold length is 140 nucleotides. In some embodiments, the first threshold length is between 130 nucleotides and 150 nucleotides. In some embodiments, the first threshold length is between 140 nucleotides and 150 nucleotides (3022). In some embodiments, the first threshold length is between 130 nucleotides and 140 nucleotides.

As for cfDNA fragments derived from mono-nucleosome constructs, a similar size phenomenon was observed for cfDNA fragments derived from di-nucleosome fragments. That is, cell-free DNA fragments having lengths in the range of about 220 nucleotides to about 340 nucleotides are generally derived from di-nucleosome constructs. On average, cfDNA fragments from di-nucleosome constructs originating from cancer cells have shorter lengths than cfDNA fragments from di-nucleosome constructs originating from somatic or hematopoietic cells. Thus, in some embodiments, in order to provide more sequencing data from cfDNA fragments enriched in a cancerous origin, sequence reads generated from shorter cfDNA molecules derived from di-nucleosome constructs are also included in the plurality of sequence reads used to determine a cancer status of the subject.

Accordingly, in some embodiments, the first plurality of sequence reads includes sequence reads of cell-free DNA molecules in the first plurality of cell-free DNA molecules having a length falling between a second threshold length and a third threshold length. In some embodiments, the second threshold length is from 240 nucleotides to 260 nucleotides and the third threshold length is from 290 nucleotides to 310 nucleotides (3024). In some embodiments, the second threshold length is 250 nucleotides (3026). In other embodiments, the second threshold length is 240, 241, 242, 243, 244, 245, 246, 247, 248, 249, 250, 251, 252, 253, 254, 255, 256, 257, 258, 259, or 260 nucleotides. In some embodiments, the third threshold length is 300 nucleotides (3028). In some embodiments, the third threshold length is 290, 291, 292, 293, 294, 295, 296, 297, 298, 299, 300, 301, 302, 303, 304, 305, 306, 307, 308, 309, or 310 nucleotides.

In some embodiments, the first plurality of sequence reads is more than 5 million sequence reads (3030). In some embodiments, the first plurality of sequence reads is more than 10 million sequence reads, or more than 20, 30, 40, 50, 60, 70, 80, 90, 100, 150, 200, 300, 400, 500, or 1000 million sequence reads. In some embodiments, the first plurality of sequence reads includes at least 1000 sequence reads for each genomic location in the plurality of genomic locations. In some embodiments, the first plurality of sequence reads includes at least 2000, sequence reads for each genomic location in the plurality of genomic locations, or at least 3000, 4000, 5000, 6000, 7500, 10,000, 15,000, 20,000, 25,000, 30,000, or 60,000 sequence reads for each genomic location in the plurality of genomic locations.

In some embodiments, the obtaining step of the method includes generating the plurality of sequencing reads from the cell-free DNA in the biological sample from the subject, using a nucleic acid sequencer. However, in other embodiments, method 3000 only includes obtaining the sequencing data from a prior sequencing reaction of cell-free DNA from a biological sample.

Methods for collecting suitable sequencing data for the methods described herein (e.g., methods 3000 and 4000) are described above, and are not reiterated here for reasons of brevity. Regardless of the exact sequencing method used, however, in some embodiments, each respective sequence read in the plurality of sequence reads is obtained by generating complementary sequence reads from both ends of a respective cell-free DNA molecule in the population of cell-free DNA, where the complementary sequence reads are combined to form the respective sequence read. For example, in some embodiments, complementary sequence reads are stitched together based on an overlapping region of sequence shared between the complementary sequence reads and/or by matching the sequences from complementary sequence reads to sequences to corresponding sequences in a reference genome for the species of the subject.

In some embodiments, the enrichment of sequence reads from cfDNA fragments originating from cancer cells is achieved by in silico size selection of the sequence reads, e.g., as described above with reference to method 2100 illustrated in FIG. 2B. Accordingly, in some embodiments, the first plurality of sequence reads is obtained by generating a precursor plurality of sequence reads, in electronic form, for cell-free nucleic acid molecules in the biological sample, and applying a length filter to the precursor plurality of sequence reads, thereby obtaining the first plurality of sequence reads (3032).

In some embodiments, the enrichment of sequence reads from cfDNA fragments originating from cancer cells is achieved by in vitro size selection of the cfDNA fragments, e.g., as described above with reference to method 2000 illustrated in FIG. 2A. Accordingly, in some embodiments, the first plurality of sequence reads is obtained by separating cell-free DNA molecules in the biological sample that are no longer than the first threshold length from cell-free DNA molecules in the biological sample that are longer than the first threshold length, and generating sequence reads from the separated cell-free DNA molecules that are no longer than the first threshold length, thereby obtaining the first plurality of sequence reads (3034). Methods and tools for separating nucleic acids by size are known in the art and include, for example, agarose gel electrophoresis, Pippin prep (Sage Sciences), SPRI beads, modifying PCR conditions, etc.

In some embodiments, the separation occurs after pooling cfDNA fragment constructs (e.g., including added UMIs, indices, primer sites, etc.) from a plurality of subjects. Advantageously, pooling samples prior to size separation reduces the amount of material, time, and cost required per subject. In other embodiments, the separation is performed on cfDNA fragments from a single subject, e.g., prior to pooling with fragments from other subjects, or without ever pooling fragments from other subjects.

In some embodiments, as described with reference to library construction within methods 2000 and 2100 and illustrated in FIGS. 2A and 2B, the method includes adding (3036) a nucleic acid fragment having a fixed length of x nucleotides to the cell-free DNA molecules of the subject, where the nucleic acid fragment includes an identifier unique to the subject. In some embodiments, nucleic acid fragments are added to both ends of the cell-free DNA molecules. Accordingly, as referred to herein, the fixed length of x nucleotides refers to the total length of all nucleic acid fragments added to either end of a cell-free DNA molecule. In some embodiments, the unique identifier encodes a unique predetermined value selected from the set $\{1, \ldots, 1024\}$, $\{1, \ldots, 4096\}$, $\{1, \ldots, 16,384\}$, $\{1, \ldots, 65,536\}$, $\{1, \ldots, 262,144\}$, $\{1, \ldots, 1,048,576\}$, $\{1, \ldots, 4,194,304\}$, $\{1, \ldots, 16,777,216\}$, $\{1, \ldots, 67,108,864\}$, $\{1, \ldots, 268,435,456\}$, $\{1, \ldots, 1,073,741, 824\}$, or $\{1, \ldots, 4,294,967,296\}$. In some embodiments, the unique identifier is localized to a contiguous set of oligonucleotides within the added nucleic acid fragment. In some embodiments, the contiguous set of oligonucleotides is an N-mer, wherein N is an integer selected from the set $\{4, \ldots, 20\}$. In some embodiments, the nucleic acid fragment also includes one or more of a UMI, a primer hybridization sequence (e.g., for PCR amplification and/or sequencing), and complementary sequences used in clustering.

In some embodiments, the fixed length x of the added nucleic acid fragment is from 100 nucleotides to 200 nucleotides (3038). In other embodiments, the fixed length x of the added nucleic acid fragment is about 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, or more nucleotides.

In some embodiments, after adding the fixed length of x nucleotides to the cfDNA molecules, the method includes pooling the cell-free DNA molecules of the biological sample of the subject with cell-free DNA molecules from a plurality of other subjects, where the cell-free DNA molecules of each respective other subject in the plurality of other subjects include an added corresponding nucleic acid fragment having a fixed length of x nucleotides, e.g., where the added corresponding nucleic acid fragment includes an identifier unique to the respective other subject. When the pool of cell-free DNAs from different subjects is sequenced, the resulting sequence reads correspond to cell-free DNAs from multiple subjects. The sequence reads are then separated into different pluralities of sequences reads, corresponding to the various subjects, based on the unique identifiers present in the added nucleic acid fragments. In this fashion, a single sequencing reaction can generate sequence reads from multiple samples. Moreover, the number of cell-free DNAs from each biological sample is reduced when the nucleic acids are size selected prior to the sequencing reaction. Advantageously, this allows for the processing of more samples per sequencing reaction, without reducing the diagnostic power of the sequencing results, providing for more efficient sequencing reactions. In fact, because the size selection enriches for cell-free DNAs derived from cancerous cells, the diagnostic power of the resulting sequencing data is greater than the diagnostic power of sequencing data that would have been generated by sequencing all of the cell-free DNAs in the biological sample. Thus, the present method improves existing methods of (i) multiplex sequencing (e.g., by facilitating the simultaneous sequencing of a greater number of samples, thereby reducing the time, computational burden, and cost of sequencing each sample) and (ii) cancer diagnostics (e.g., by improving the diagnostic power of the data set and by reducing the computational burden required to process the smaller data set).

Method 3000 then includes using (3042) the first plurality of sequence reads to identify a relative copy number at each respective genomic location in a plurality of predetermined genomic locations in the genome of the subject, e.g., where the plurality of genomic locations includes at least fifty genomic locations. In some embodiments, the plurality of predetermined locations includes at least 25, 50, 75, 100, 150, 200, 250, 300, 400, 500, 750, 1000, 1500, 2000, 2500, 3000, 4000, 5000, 7500, 10,000, 15,000, 20,000, 25,000, 30,000, 40,000, 50,000, 75,000, 100,000, or more predetermined locations. In some embodiments, the plurality of genomic locations collectively represents from about 30% to about 90% of a reference genome of the species. For instance, in some embodiments, the plurality of genomic locations collectively represents from 30% to 50% of a reference genome of the species, or from 50% to 70%, or from 70% to 90% of a reference genome of the species. In some embodiments, the percentage of the reference genome collectively represented by the plurality of genomic locations does not include any portions of sex determining chromosomes of the species.

In some embodiments, the subject is human and a genomic location in the plurality of genomic locations is a predetermined exon or intron in a reference human genome (3044). For instance, in some embodiments, the relative copy number is determined on the gene level, e.g., the relative copy number of a predefined set of genes is determined. In some embodiments, the predefined set of genes are selected based on evaluation of copy number variation across a plurality of cancer patients to identify genes for which copy number is informative of a relevant cancer status of the subject, e.g., the presence or absence of cancer, a type of cancer, a stage of cancer, a prognosis for a cancer, or a therapeutic prediction for a cancer.

In some embodiments, the subject is human and each genomic location in the plurality of genomic locations is a bin in plurality of bins and where each bin in the plurality of bins represents a predetermined portion of a human reference genome (3046). That is, in some embodiments, classification using method 3000 relies upon the relative copy number of a plurality of discrete, identifiable portions of the genome, as opposed to an overall metric for copy number variation across the genome as a whole. In some embodiments, the plurality of bins covers less than the entire human genome, i.e., the plurality of bins is a subset of a larger set of bins spanning the entire human genome. In some embodiments, the plurality of bins is selected based on evaluation of copy number variation across a plurality of cancer patients to identify bins for which copy number is informative of a relevant cancer status of the subject, e.g., the presence or absence of cancer, a type of cancer, a stage of cancer, a prognosis for a cancer, or a therapeutic prediction for a cancer. One method for selecting such bins is disclosed in U.S. Provisional Patent Application Ser. No. 62/642,461, entitled METHOD AND SYSTEM FOR SELECTING, MANAGING, AND ANALYZING DATA OF HIGH DIMENSIONALITY, the content of which is incorporated by reference herein, in its entirety, for all purposes.

In some embodiments, the bins are defined by dividing a reference genome into multiple genomic locations. Here, the reference genome includes all sequence information of a subject that is representative of the organism. In some embodiments, the multiple regions are of the same size. In some embodiments, the multiple regions can have different sizes. In some embodiments, a genomic location can be defined by the number of nucleic acid residues within the region. In some embodiments, a reference genome can be divided multiple times. For example, a wider or bigger genomic location allows the entire genome to be scanned or analyzed quickly. In some embodiments, if a region is of interest but seems to correspond to high systematic errors (hence should be discarded from further analysis), the region (and sometimes adjustment regions) can be re-grouped and re-divided into smaller genomic locations. This way, the presumed systematic errors can be more precisely characterized; for example, a portion of the original region may have low variability and can be preserved for further analysis.

Any suitable size can be used to define genomic locations. For example, a genomic location can include 10,000 bases or fewer, 20,000 bases or fewer, 30,000 bases or fewer, 40,000 bases or fewer, 50,000 bases or fewer, 60,000 bases or fewer, 70,000 bases or fewer, 80,000 bases or fewer, 90,000 bases or fewer, 100,000 bases or fewer, 110,000 bases or fewer, 120,000 bases or fewer, 130,000 bases or fewer, 140,000 bases or fewer, 150,000 bases or fewer, 160,000 bases or fewer, 170,000 bases or fewer, 180,000 bases or fewer, 190,000 bases or fewer, 200,000 bases or fewer, 220,000 bases or fewer, 250,000 bases or fewer, 270,000 bases or fewer, 300,000 bases or fewer, 350,000 bases or fewer, 400,000 bases or fewer, 500,000 bases or fewer, 600,000 bases or fewer, 700,000 bases or fewer, 800,000 bases or fewer, 900,000 bases or fewer, or 1,000,000 bases or fewer. In some embodiments, a genomic location can include more than 1,000,000 bases. In some embodiments, each genomic location in the plurality of genomic locations includes from 10,000 bases to 25,000 bases. In some embodiments, each genomic location in the plurality of genomic locations includes from 25,000 bases to 50,000 bases. In some embodiments, each genomic location in the plurality of genomic locations includes from 50,000 bases to 75,000 bases. In some embodiments, each genomic location in the plurality of genomic locations includes from 75,000 bases to 100,000 bases. In some embodiments, each genomic location in the plurality of genomic locations includes from 100,000 bases to 250,000 bases. In some embodiments, each genomic location in the plurality of genomic locations includes from 250,000 bases to 500,000 bases. In some embodiments, each genomic location in the plurality of genomic locations includes from 500,000 bases to 1,000,000 bases.

In some embodiments, the predetermined genomic locations are selected from a precursor set of genomic locations by a method comprising removing respective genomic locations in the precursor set having a variance that exceeds a threshold variance in relative copy number within a training set of electronic sequence reads (3054). Methods for removing genomic locations from a precursor set based on variance thresholds are disclosed in U.S. Provisional Patent Application Ser. No. 62/642,461, entitled METHOD AND SYSTEM FOR SELECTING, MANAGING, AND ANALYZING DATA OF HIGH DIMENSIONALITY, the content of which is incorporated by reference herein, in its entirety, for all purposes.

In some embodiments, the average coverage rate of the plurality of sequence reads across the plurality of genomic locations (e.g., across the entirety of each genomic location) is at least 3× (3048). In some embodiments, the average coverage rate of the plurality of sequence reads across the plurality of genomic locations (e.g., across the entirety of each genomic location) is at least 5× (3050). In some embodiments, the average coverage rate of the plurality of sequence reads across the plurality of genomic locations (e.g., across the entirety of each genomic location) is at least 10× (3052). In some embodiments, the average coverage rate of the plurality of sequence reads across the plurality of genomic locations (e.g., across the entirety of each genomic location) is between about 0.1× and about 35×, or between about 2× and about 20×, e.g., about 0.1×, 0.5×, 1×, 2×, 3×, 4×, 5×, 6×, 7×, 8×, 9×, 10×, 11×, 12×, 13×, 14×, 15×, 16×, 17×, 18×, 19×, 20×, 25×, 30×, 35×, etc.

In some embodiments, e.g., where cfDNA fragments are size-selected prior to sequencing, the sequence coverage of the sequencing reaction is on the lower end of this range. For instance, as shown in Example 5, size-selection of sub-sampled data from the CCGA study resulting in an average sequence coverage of 0.09× still performed about as well as non-size selected data having 5× coverage. Thus, if the cfDNA is size-selected prior to sequencing, much lower sequence coverage would be expected to provide the necessary diagnostic sensitivity at high specificity. Accordingly, in some embodiments, where the cfDNA fragments are size-selected prior to sequencing, the average coverage rate of the plurality of sequence reads across the plurality of genomic locations (e.g., across the entirety of each genomic location) is between about 0.1× and about 5×, or between about 0.5× and about 3×, e.g., about or at least 0.1×, 0.2×, 0.3×, 0.4×, 0.5×, 0.6×, 0.7×, 0.8×, 0.9×, 1×, 1.25×, 1.5×, 1.75×, 2×, 2.5×, 3×, 3.5×, 4×, 4.5×, 5×, 6×, 7×, 8×, 9×, or 10×.

In some embodiments, e.g., where cfDNA fragments are not size-selected prior to sequencing, but rather the resulting sequence reads are filtered, the sequence coverage of the sequencing reaction is not on the low end of this range. For instance, as shown in Example 5, in silico filtering of a sub-sampled CCGA data set having 5× sequence coverage resulted in a filtered data set having only 0.09× sequence coverage. Accordingly, in some embodiments, where the cfDNA sequence reads are size-selected after sequencing, the average coverage rate of the plurality of sequence reads across the plurality of genomic locations (e.g., across the entirety of each genomic location) is between about 2× and about 35×, or between about 3× and about 10×, e.g., about or at least 2×, 3×, 4×, 5×, 6×, 7×, 8×, 9×, 10×, 11×, 12×, 13×, 14×, 15×, 16×, 17×, 18×, 19×, 20×, 25×, 30×, or 35×.

In some embodiments, the tumor fraction of the sample, prior to size selection, is between about 0.1% and 100%, e.g., between about 0.1% and about 1%, between about 1% and about 5%, between about 5% and about 10%, between about 10% and about 25%, between about 25% and about 50%, between about 50% and about 100%. In some embodiments, the tumor fraction of the sample, prior to size selection, is at least 0.1%, 0.2%, 0.3%, 0.4%, 0.5%, 0.6%, 0.7%, 0.8%, 0.9%, 1%, 2%, 3%, 4%, 5%, 10%, 15%, 20%, 25%, or greater.

Method 3000 then includes classifying (3056) the subject, where the classifying includes applying genetic information about the subject obtained from the biological sample, where the genetic information is the identification of the relative copy number at each respective genomic location, to a classifier, thereby determining the cancer class of the subject. That is, in some embodiments, method 3000 only uses copy number data of the predetermined plurality of genomic locations from the size-selected sequence reads. In other words, in some embodiments, variant data obtained from the sequencing reaction is not used in the classification. However, in some embodiments, predetermined variant data from the genome of subject is used in the classification, e.g., an allele status for one or more predefined loci.

In some embodiments, determining the cancer class of the subject includes determining whether or not the subject has cancer (3058). For instance, in some embodiments, the subject has not been diagnosed with cancer and method 3000 is performed to determine whether the subject has cancer.

In some embodiments, determining the cancer class of the subject includes determining a stage of a cancer in the subject (3060), for instance stage 0, stage I, stage II, stage III, or stage IV cancer. In some embodiments, the subject has already been diagnosed with cancer and method 3000 is performed to determine a stage of the cancer. In some embodiments, the subject has not been diagnosed with cancer and method 3000 is performed to determine whether the subject has cancer and, if so, the stage of the cancer. In some embodiments, the stage of the cancer is a stage of a breast cancer, a stage of a lung cancer, a stage of a prostate cancer, a stage of a colorectal cancer, a stage of a renal cancer, a stage of a uterine cancer, a stage of a pancreatic cancer, a stage of a cancer of the esophagus, a stage of a lymphoma, a stage of a head/neck cancer, a stage of an ovarian cancer, a stage of a hepatobiliary cancer, a stage of a melanoma, a stage of a cervical cancer, a stage of a multiple myeloma, a stage of a leukemia, a stage of a thyroid cancer, a stage of a bladder cancer, or a stage of a gastric cancer (3062).

In some embodiments, determining the cancer class of the subject includes determining a type of a cancer present in the subject (3064). In some embodiments, the subject has already been diagnosed with cancer and method 3000 is performed to determine a type of the cancer. In some embodiments, the subject has not been diagnosed with cancer and method 3000 is performed to determine whether the subject has cancer and, if so, the type of the cancer. In some embodiments, the type of cancer is breast cancer, lung cancer, prostate cancer, colorectal cancer, renal cancer, uterine cancer, pancreatic cancer, cancer of the esophagus, a lymphoma, head/neck cancer, ovarian cancer, a hepatobiliary cancer, a melanoma, cervical cancer, multiple myeloma, leukemia, thyroid cancer, bladder cancer, or gastric cancer (3066).

In some embodiments, determining the cancer class of the subject includes determining a prognosis for a cancer in the subject (3068), e.g., a life expectancy without treatment, a life expectancy with treatment, or an expected response to a particular therapy. In some embodiments, the prognosis is a survival statistic, e.g., a cancer-specific survival statistic (e.g., 1-year, 2-year, 5-year, 10-year, 20-year, or other survival time), a relative survival statistic (e.g., 1-year, 2-year, 5-year, 10-year, 20-year, or other survival time), an overall survival statistic (e.g., 1-year, 2-year, 5-year, 10-year, 20-year, or other survival time), or a disease-free survival statistic (e.g., 1-year, 2-year, 5-year, 10-year, 20-year, or other recurrence-free or progression-free survival time). In some embodiments, the prognosis is a predicted response to a particular therapeutic regimen.

In some embodiments, the classifier is a multinomial classifier that provides a plurality of likelihoods responsive to the identification of the relative copy number at each respective genomic location, where each respective likelihood in the plurality of likelihoods is a likelihood that the test subject has a corresponding cancer class in a plurality of cancer classes (3070). In some embodiments, the classifier is a multivariate logistic regression algorithm, a neural network algorithm, or a convolutional neural network algorithm (3072). In some embodiments, the classifier is a neural network algorithm, a support vector machine algorithm, a Naive Bayes algorithm, a nearest neighbor algorithm, a boosted trees algorithm, a random forest algorithm, a convolutional neural network algorithm, a decision tree algorithm, a regression algorithm, or a clustering algorithm (3074).

In some embodiments, the classifier uses a linear or non-linear combination of the relative copy number at two or more respective genomic locations in the plurality of genomic locations (3076).

In some embodiments, the linear or non-linear combination of the relative copy number at two or more respective genomic locations is identified (3078) by subjecting the relative copy number at each respective genomic position in the precursor set across a training set of electronic sequence reads to a dimension reduction technique. In some embodiments, the dimension reduction algorithm is a linear dimension reduction algorithm or a non-linear dimension reduction algorithm (3080). In some embodiments, the dimension reduction algorithm is a linear dimension reduction algorithm selected from the group consisting of a principal component analysis algorithm and a factor analysis algorithm (3082). In some embodiments, the dimension reduction algorithm is a non-linear dimension reduction algorithm selected from the group consisting of Sammon mapping, curvilinear components analysis, a stochastic neighbor embedding (SNE) algorithm, an Isomap algorithm, a maximum variance unfolding algorithm, a locally linear embedding algorithm, and a t-SNE algorithm (3084). In some embodiments, the dimension reduction algorithm is a non-negative matrix factorization algorithm, a kernel principal component analysis algorithm, a graph-based kernel principal component analysis algorithm, a linear discriminant analysis algorithm, or a generalized discriminant analysis algorithm (3086). In some embodiments, the dimension reduction algorithm is uniform manifold approximation and projection (UMAP) algorithm, a LargeVis algorithm, a Laplacian Eigenmap algorithm, or a Fisher's linear discriminant analysis algorithm (3088).

In some embodiments, the classifying further includes applying the identity of an allele at a locus in the genome of the subject to the classifier (3090). In some embodiments, the identity of the allele is determined from the size-selected sequencing reads, e.g., generated according to step 2010 or 2110 as described above. In some embodiments, the identity of the allele is determined from a separate sequencing reaction, e.g., from a different sample and/or performed at an earlier time.

In some embodiments, the classifying further includes applying a methylation state at a locus in the genome of the subject to the classifier (3092). In some embodiments, the methylation state at the locus is determined from the size-selected sequencing reads, e.g., generated according to step 2010 or 2110 as described above. In some embodiments, the methylation state at the locus is determined from a separate sequencing reaction, e.g., from a different sample and/or performed at an earlier time.

In some embodiments, the cancer class of the subject is determined with a first degree of confidence, and the first degree of confidence is greater than a second degree of confidence obtainable by application of genetic information consisting of relative copy number at each respective genomic location in the plurality of genomic locations obtained from a second plurality of sequence reads from the biological sample, to the classifier, where the second plurality of sequence reads encodes (i) cell-free DNA molecules that are shorter than the first threshold length and (ii) cell-free DNA molecules that are longer than the first threshold length (3094). That is, the confidence with which the cancer class is determined is greater when the size-selected sequencing reads are used than it would have been had the cancer class been determined from sequence reads generated against all cfDNA fragments in the sample (not size-selected). In some embodiments, while the determination of cancer classes associated with a positive diagnosis for a cancer in the subject is made with a greater confidence using the size-selected sequence reads, determinations of a cancer class associated with a diagnosis that the subject does not have cancer are not made with a greater confidence than if a set of non-size-selected sequence reads were used. That is, in some embodiments, the methods provided herein result in cancer classification that are made with greater confidence when the subject has cancer, but with a similar or lower confidence when the subject does not have cancer. This, of course, does not require that the classification with a full set of sequence reads from a biological sample is actually performed, or that the second confidence is actually calculated.

In some embodiments, however, the second classification and/or confidence is determined. For example, in some embodiments, method 3000 includes obtaining (3096) the second plurality of sequence reads from the biological sample, using the second plurality of sequence reads to identify a relative copy number at each respective genomic location in the plurality of genomic locations in the genome of the subject, and classifying the subject, where the classifying includes applying genetic information about the subject obtained from the biological sample, where the genetic information is the relative copy number at each respective genomic location in the plurality of genomic locations obtained from a second plurality of sequence reads from the biological sample, to the classifier, thereby determining the cancer class of the subject with the second confidence.

FIGS. 4A-4F are flow diagrams illustrating a method 4000 of for determining the relative copy number at a plurality of genomic locations in a pool of size-selected cell-free DNA molecules. Some steps of method 4000 are performed at a computer system (e.g., computer system 100 in FIG. 1) having one or more processors, and memory storing one or more programs for execution by the one or more processors for segmenting all of a portion of a reference genome for the species of the subject. Some operations in method 4000 are, optionally, combined and/or the order of some operations is, optionally, changed.

Method 4000 includes obtaining (4002) a respective plurality of cell-free DNA molecules from each corresponding biological sample in a plurality of biological samples, where each corresponding biological sample in the plurality of biological samples is from a different subject in a plurality of subjects of a single species, thereby forming a set of pluralities of cell-free DNA molecules.

In some embodiments, each biological sample in the plurality of biological sample includes blood, whole blood, plasma, serum, urine, cerebrospinal fluid, fecal material, saliva, sweat, tears, pleural fluid, pericardial fluid, or peritoneal fluid of the corresponding subject (4004). In some embodiments, each biological sample in the plurality of biological sample is a blood sample (4006). In some embodiments, each biological sample in the plurality of biological sample is a blood plasma sample (4008). In some embodiments, the blood sample is a whole blood sample, and prior to generating the plurality of sequence reads from the whole blood sample, white blood cells are removed from the whole blood sample. In some embodiments, the white blood cells are collected as a second type of sample, e.g., according to a buffy coat extraction method, from which additional sequencing data may or may not be obtained. Methods for buffy coat extraction of white blood cells are known in the art, for example, as described in U.S. Provisional Application No. 62/679,347, filed on Jun. 1, 2018, the content of which is incorporated herein by reference, in its entirety, for all purposes. In some embodiments, the method further includes obtaining a second plurality of sequence reads in electronic form of genomic DNA from the white blood cells removed from the whole blood sample. In some embodiments, the second plurality of sequence reads is used to identify allele variants arising from clonal hematopoiesis, as opposed to germline allele variants and/or allele variants arising from a cancer in the subject.

As described above, it is known that mono- and di-nucleosomes fragmented from the genomes of non-cancerous somatic cells, hematopoietic cells (e.g., white blood cells), and (when the subject has cancer) cancerous cells. Thus, in some embodiments, the cell-free DNA molecules in each sample originate from at least non-cancerous somatic cells and hematopoietic cells (e.g., white blood cells). In some embodiments, each sample also includes cell-free DNA molecules originating from cancerous cells. In some embodiments, it is unknown whether any respective subject has cancer and, thus, whether cell-free DNA originating from cancerous cells in present in the sample prior to analysis. Accordingly, in some embodiments, one or more respective subject in the plurality of subjects has not been diagnosed as having cancer (4012). In some embodiments, one or more respective subject in the plurality of subjects has already been diagnosed with cancer and, accordingly, it is known that the cell-free DNA originating from cancerous cells is present in the corresponding sample from the respective subject, prior to analysis. In some embodiments, each subject in the plurality of subjects is human (4010).

Method 4000 then includes adding (4014), for each respective subject in the plurality of subjects, a nucleic acid fragment having a fixed length of x nucleotides to the cell-free DNA molecules of the respective subject, where the nucleic acid fragment includes an identifier unique to the respective subject. In some embodiments, nucleic acid fragments are added to both ends of the cell-free DNA molecules. Accordingly, as referred to herein, the fixed length of x nucleotides refers to the total length of all nucleic acid fragments added to either end of a cell-free DNA molecule. In some embodiments, the unique identifier encodes a unique predetermined value selected from the set $\{1, \ldots, 1024\}$, $\{1, \ldots, 4096\}$, $\{1, \ldots, 16,384\}$, $\{1, \ldots, 65,536\}$, $\{1, \ldots, 262,144\}$, $\{1, \ldots, 1,048,576\}$, $\{1, \ldots, 4,194,304\}$, $\{1, \ldots, 16,777,216\}$, $\{1, 67,108,864\}$, $\{1, \ldots, 268,435,456\}$, $\{1, \ldots, 1,073,741,824\}$, or $\{1, \ldots, 4,294,967,296\}$. In some embodiments, the unique identifier is localized to a contiguous set of oligonucleotides within the added nucleic acid fragment. In some embodiments, the contiguous set of oligonucleotides is an N-mer, wherein N is an integer selected from the set $\{4, \ldots, 20\}$. In some embodiments, the nucleic acid fragment also includes one or more of a UMI, a primer hybridization sequence (e.g., for PCR amplification and/or sequencing), and complementary sequences used in clustering.

In some embodiments, the fixed length x of the added nucleic acid fragment is from 100 nucleotides to 200 nucleotides (4016). In other embodiments, the fixed length x of the added nucleic acid fragment is about 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, or more nucleotides.

Method 4000 then includes pooling (4018) cell-free DNA molecules from each respective subject in the plurality of subjects, thereby forming a pool of cell-free DNA molecules. When the pool of cell-free DNAs from different subjects is sequenced, the resulting sequence reads correspond to cell-free DNAs from multiple subjects. The sequence reads are then separated into different pluralities of sequences reads, corresponding to the various subjects, based on the unique identifiers present in the added nucleic acid fragments. In this fashion, a single sequencing reaction can generate sequence reads from multiple samples. Moreover, the number of cell-free DNAs from each biological sample is reduced when the nucleic acids are size selected prior to the sequencing reaction. Advantageously, this allows for the processing of more samples per sequencing reaction, without reducing the diagnostic power of the sequencing results, providing for more efficient sequencing reactions. In fact, because the size selection enriches for cell-free DNAs derived from cancerous cells, the diagnostic power of the resulting sequencing data is greater than the diagnostic power of sequencing data that would have been generated by sequencing all of the cell-free DNAs in the biological sample. Thus, the present method improves existing methods of (i) multiplex sequencing (e.g., by facilitating the simultaneous sequencing of a greater number of samples, thereby reducing the time, computational burden, and cost of sequencing each sample) and (ii) cancer diagnostics (e.g., by improving the diagnostic power of the data set and by reducing the computational burden required to process the smaller data set).

Method 4000 then includes isolating (4020) cell-free DNA molecules in the pool of cell-free DNA molecules having a length that is no longer than a first threshold length, where the first threshold length is less than 160+x, thereby forming a length-selected pool of cell-free DNA molecules. Methods and tools for separating nucleic acids by size are known in the art and include, for example, agarose gel electrophoresis, Pippin prep (Sage Sciences), SPRI beads, modifying PCR conditions, etc.

Generally, the threshold length is set so as to increase the percentage of sequence reads that are generated for cfDNA fragments originating from cancer cells, as opposed to cfDNA fragments originating from somatic or hematopoietic cells. For instance, as can be seen by the shifting of cfDNA fragment length distribution as a function of tumor fraction in FIG. 5, cfDNA fragments originating from cancer cells have, on average, shorter lengths than cfDNA fragments originating from somatic cells or hematopoietic cells. Thus, as shown in FIG. 6, the probability of a given fragment being derived from a cancer cell increases as the size of the fragment decreases. Accordingly, in some embodiments, the first threshold length is set to a value of less than 160+x nucleotides. In some embodiments, the first threshold length is 150+x nucleotides or less (4022). In some embodiments, the first threshold length is 140+x nucleotides or less (4024). In some embodiments, the first threshold length is 130+x nucleotides or less (4026). In some embodiments, the first threshold length is 159+x, 158+x, 157+x, 156+x, 155+x, 154+x, 153+x, 152+x, 151+x, 150+x, 149+x, 148+x, 147+x, 146+x, 145+x, 144+x, 143+x, 142+x, 141+x, 140+x, 139+x, 138+x, 137+x, 136+x, 135+x, 134+x, 133+x, 132+x, 131+x, 130+x, 129+x, 128+x, 127+x, 126+x, 125+x, or fewer nucleotides. In one embodiment, the first threshold length is 140+x nucleotides. In some embodiments, the first threshold length is between 130+x nucleotides and 150+x nucleotides. In some embodiments, the first threshold length is between 140+x nucleotides and 150+x nucleotides (4030). In some embodiments, the first threshold length is between 130+x nucleotides and 140+x nucleotides.

In some embodiments, the separation is performed on cfDNA fragments from a single subject, e.g., prior to pooling with fragments from other subjects, or without ever pooling fragments from other subjects.

As for cfDNA fragments derived from mono-nucleosome constructs, a similar size phenomenon was observed for cfDNA fragments derived from di-nucleosome fragments. That is, cell-free DNA fragments having lengths in the range of about 220 nucleotides to about 340 nucleotides are generally derived from di-nucleosome constructs. On average, cfDNA fragments from di-nucleosome constructs originating from cancer cells have shorter lengths than cfDNA fragments from di-nucleosome constructs originating from somatic or hematopoietic cells. Thus, in some embodiments, in order to provide more sequencing data from cfDNA fragments enriched in a cancerous origin, sequence reads generated from shorter cfDNA molecules derived from di-nucleosome constructs are also included in the plurality of sequence reads used to determine a cancer status of the subject.

Accordingly, in some embodiments, the first plurality of sequence reads includes sequence reads of cell-free DNA molecules in the first plurality of cell-free DNA molecules having a length falling between a second threshold length and a third threshold length. In some embodiments, the second threshold length is from 240+x nucleotides to 260+x nucleotides and the third threshold length is from 290+x nucleotides to 310+x nucleotides (4032). In some embodiments, the second threshold length is 250+x nucleotides (4034). In other embodiments, the second threshold length is 240+x, 241+x, 242+x, 243+x, 244+x, 245+x, 246+x, 247+x, 248+x, 249+x, 250+x, 251+x, 252+x, 253+x, 254+x, 255+x, 256+x, 257+x, 258+x, 259+x, or 260+x nucleotides. In some embodiments, the third threshold length is 300+x nucleotides (4036). In some embodiments, the third threshold length is 290+x, 291+x, 292+x, 293+x, 294+x, 295+x, 296+x, 297+x, 298+x, 299+x, 300+x, 301+x, 302+x, 303+x, 304+x, 305+x, 306+x, 307+x, 308+x, 309+x, or 310+x nucleotides.

In some embodiments, method 40 then includes sequencing (4038) cell-free DNA molecules in the length-selected pool of cell-free DNA molecules, thereby generating a plurality of sequence reads in electronic form. In some embodiments, the first plurality of sequence reads is more than 5000 sequence reads (4040). In some embodiments, the first plurality of sequence reads is more than 10 million sequence reads, or more than 20, 30, 40, 50, 60, 70, 80, 90, 100, 150, 200, 300, 400, 500, or 1000 million sequence reads. In some embodiments, the first plurality of sequence reads includes at least 1000 sequence reads for each genomic location in the plurality of genomic locations. In some embodiments, the first plurality of sequence reads includes at least 2000, sequence reads for each genomic location in the plurality of genomic locations, or at least 3000, 4000, 5000, 6000, 7500, 10,000, 15,000, 20,000, 25,000, 30,000, or 60,000 sequence reads for each genomic location in the plurality of genomic locations.

Methods for collecting suitable sequencing data for the methods described herein (e.g., methods 3000 and 4000) are described above, and are not reiterated here for reasons of brevity. Regardless of the exact sequencing method used, however, in some embodiments, each respective sequence read in the plurality of sequence reads is obtained by generating complementary sequence reads from both ends of a respective cell-free DNA molecule in the population of cell-free DNA, where the complementary sequence reads are combined to form the respective sequence read. For example, in some embodiments, complementary sequence reads are stitched together based on an overlapping region of sequence shared between the complementary sequence reads and/or by matching the sequences from complementary sequence reads to sequences to corresponding sequences in a reference genome for the species of the subject.

Method 4000 then includes determining (4042) the relative copy number at each respective genomic location in a plurality of predetermined genomic locations of the cell-free DNA molecules in the length-selected pool of cell-free DNA molecules. In some embodiments, the plurality of genomic locations includes at least fifty genomic locations (4044). In some embodiments, the plurality of predetermined locations includes at least 25, 50, 75, 100, 150, 200, 250, 300, 400, 500, 750, 1000, 1500, 2000, 2500, 3000, 4000, 5000, 7500, 10,000, 15,000, 20,000, 25,000, 30,000, 40,000, 50,000, 75,000, 100,000, or more predetermined locations. In some embodiments, the plurality of genomic locations collectively represents from about 30% to about 90% of a reference genome of the species. For instance, in some embodiments, the plurality of genomic locations collectively represents from 30% to 50% of a reference genome of the species, or from 50% to 70%, or from 70% to 90% of a reference genome of the species. In some embodiments, the percentage of the reference genome collectively represented by the plurality of genomic locations does not include any portions of sex determining chromosomes of the species.

In some embodiments, the subject is human and a genomic location in the plurality of genomic locations is a predetermined exon or intron in a reference human genome (4046). For instance, in some embodiments, the relative copy number is determined on the gene level, e.g., the relative copy number of a predefined set of genes is determined. In some embodiments, the predefined set of genes are selected based on evaluation of copy number variation across a plurality of cancer patients to identify genes for which copy number is informative of a relevant cancer status of the subject, e.g., the presence or absence of cancer, a type of cancer, a stage of cancer, a prognosis for a cancer, or a therapeutic prediction for a cancer.

In some embodiments, the subject is human and each genomic location in the plurality of genomic locations is a bin in plurality of bins and where each bin in the plurality of bins represents a predetermined portion of a human reference genome (4048). That is, in some embodiments, classification using method 4000 relies upon the relative copy number of a plurality of discrete, identifiable portions of the genome, as opposed to an overall metric for copy number variation across the genome as a whole. In some embodiments, the plurality of bins covers less than the entire human genome, i.e., the plurality of bins is a subset of a larger set of bins spanning the entire human genome. In some embodiments, the plurality of bins is selected based on evaluation of copy number variation across a plurality of cancer patients to identify bins for which copy number is informative of a relevant cancer status of the subject, e.g., the presence or absence of cancer, a type of cancer, a stage of cancer, a prognosis for a cancer, or a therapeutic prediction for a cancer. One method for selecting such bins is disclosed in U.S. Provisional Patent Application Ser. No. 62/642,461, entitled METHOD AND SYSTEM FOR SELECTING, MANAGING, AND ANALYZING DATA OF HIGH DIMENSIONALITY, the content of which is incorporated by reference herein, in its entirety, for all purposes.

In some embodiments, the bins are defined by dividing a reference genome into multiple genomic locations. Here, the reference genome includes all sequence information of a subject that is representative of the organism. In some embodiments, the multiple regions are of the same size. In some embodiments, the multiple regions can have different sizes. In some embodiments, a genomic location can be defined by the number of nucleic acid residues within the region. In some embodiments, a reference genome can be divided multiple times. For example, a wider or bigger genomic location allows the entire genome to be scanned or analyzed quickly. In some embodiments, if a region is of interest but seems to correspond to high systematic errors (hence should be discarded from further analysis), the region (and sometimes adjustment regions) can be re-grouped and re-divided into smaller genomic locations. This way, the presumed systematic errors can be more precisely characterized; for example, a portion of the original region may have low variability and can be preserved for further analysis.

Any suitable size can be used to define genomic locations. For example, a genomic location can include 10,000 bases or fewer, 20,000 bases or fewer, 30,000 bases or fewer, 40,000 bases or fewer, 50,000 bases or fewer, 60,000 bases or fewer, 70,000 bases or fewer, 80,000 bases or fewer, 90,000 bases or fewer, 100,000 bases or fewer, 110,000 bases or fewer, 120,000 bases or fewer, 130,000 bases or fewer, 140,000 bases or fewer, 150,000 bases or fewer, 160,000 bases or fewer, 170,000 bases or fewer, 180,000 bases or fewer, 190,000 bases or fewer, 200,000 bases or fewer, 220,000 bases or fewer, 250,000 bases or fewer, 270,000 bases or fewer, 300,000 bases or fewer, 350,000 bases or fewer, 400,000 bases or fewer, 500,000 bases or fewer, 600,000 bases or fewer, 700,000 bases or fewer, 800,000 bases or fewer, 900,000 bases or fewer, or 1,000,000 bases or fewer. In some embodiments, a genomic location can include more than 1,000,000 bases. In some embodiments, each genomic location in the plurality of genomic locations includes from 10,000 bases to 25,000 bases. In some embodiments, each genomic location in the plurality of genomic locations includes from 25,000 bases to 50,000 bases. In some embodiments, each genomic location in the plurality of genomic locations includes from 50,000 bases to 75,000 bases. In some embodiments, each genomic location in the plurality of genomic locations includes from 75,000 bases to 100,000 bases. In some embodiments, each genomic location in the plurality of genomic locations includes from 100,000 bases to 250,000 bases. In some embodiments, each genomic location in the plurality of genomic locations includes from 250,000 bases to 500,000 bases. In some embodiments, each genomic location in the plurality of genomic locations includes from 500,000 bases to 1,000,000 bases.

In some embodiments, the predetermined genomic locations are selected from a precursor set of genomic locations by a method comprising removing respective genomic locations in the precursor set having a variance that exceeds a threshold variance in relative copy number within a training set of electronic sequence reads (4056). Methods for removing genomic locations from a precursor set based on variance thresholds are disclosed in U.S. Provisional Patent Application Ser. No. 62/642,461, entitled METHOD AND SYSTEM FOR SELECTING, MANAGING, AND ANALYZING DATA OF HIGH DIMENSIONALITY, the content of which is incorporated by reference herein, in its entirety, for all purposes.

In some embodiments, the average coverage rate of the plurality of sequence reads across the plurality of genomic locations (e.g., across the entirety of each genomic location) is at least 3× (4050). In some embodiments, the average coverage rate of the plurality of sequence reads across the plurality of genomic locations (e.g., across the entirety of each genomic location) is at least 5× (4052). In some embodiments, the average coverage rate of the plurality of sequence reads across the plurality of genomic locations (e.g., across the entirety of each genomic location) is at least 10× (4054). In some embodiments, the average coverage rate of the plurality of sequence reads across the plurality of genomic locations (e.g., across the entirety of each genomic location) is between about 0.1× and about 35×, or between about 2× and about 20×, e.g., about 0.1×, 0.5×, 1×, 2×, 3×, 4×, 5×, 6×, 7×, 8×, 9×, 10×, 11×, 12×, 13×, 14×, 15×, 16×, 17×, 18×, 19×, 20×, 25×, 30×, 35×, etc.

In some embodiments, e.g., where cfDNA fragments are size-selected prior to sequencing, the sequence coverage of the sequencing reaction is on the lower end of this range. For instance, as shown in Example 5, size-selection of sub-sampled data from the CCGA study resulting in an average sequence coverage of 0.09× still performed about as well as non-size selected data having 5× coverage. Thus, if the cfDNA is size-selected prior to sequencing, much lower sequence coverage would be expected to provide the necessary diagnostic sensitivity at high specificity. Accordingly, in some embodiments, where the cfDNA fragments are size-selected prior to sequencing, the average coverage rate of the plurality of sequence reads across the plurality of genomic locations (e.g., across the entirety of each genomic location) is between about 0.1× and about 5×, or between about 0.5× and about 3×, e.g., about or at least 0.1×, 0.2×, 0.3×, 0.4×, 0.5×, 0.6×, 0.7×, 0.8×, 0.9×, 1×, 1.25×, 1.5×, 1.75×, 2×, 2.5×, 3×, 3.5×, 4×, 4.5×, 5×, 6×, 7×, 8×, 9×, or 10×.

In some embodiments, the tumor fraction of the sample, prior to size selection, is between about 0.1% and 100%, e.g., between about 0.1% and about 1%, between about 1% and about 5%, between about 5% and about 10%, between about 10% and about 25%, between about 25% and about 50%, between about 50% and about 100%. In some embodiments, the tumor fraction of the sample, prior to size selection, is at least 0.1%, 0.2%, 0.3%, 0.4%, 0.5%, 0.6%, 0.7%, 0.8%, 0.9%, 1%, 2%, 3%, 4%, 5%, 10%, 15%, 20%, 25%, or greater.

In some embodiments, method 4000 then includes classifying (4058) the cancer class of each respective subject in the plurality of subjects by applying genetic information about the subject obtained from the biological sample from the respective subject, where the genetic information is the analyzed relative copy number at each respective genomic location, to a classifier. That is, in some embodiments, method 4000 only uses copy number data of the predetermined plurality of genomic locations from the size-selected sequence reads. In other words, in some embodiments, variant data obtained from the sequencing reaction is not used in the classification. However, in some embodiments, predetermined variant data from the genome of subject is used in the classification, e.g., an allele status for one or more predefined loci.

In some embodiments, classifying the cancer class of each respective subject includes determining whether or not the respective subject has cancer (4060). For instance, in some embodiments, one or more respective subjects have not been diagnosed with cancer and method 4000 is performed to determine whether the one or more subjects have cancer.

In some embodiments, classifying the cancer class of each respective subject includes determining a stage of a cancer in the respective subject (4062), for instance stage 0, stage I, stage II, stage III, or stage IV cancer. In some embodiments, one or more respective subjects have already been diagnosed with cancer and method 4000 is performed to determine a stage of the cancers. In some embodiments, one or more respective subjects have not been diagnosed with cancer and method 4000 is performed to determine whether the one or more subjects have cancer and, if so, the stage of the cancer. In some embodiments, the stage of the cancer is a stage of a breast cancer, a stage of a lung cancer, a stage of a prostate cancer, a stage of a colorectal cancer, a stage of a renal cancer, a stage of a uterine cancer, a stage of a pancreatic cancer, a stage of a cancer of the esophagus, a stage of a lymphoma, a stage of a head/neck cancer, a stage of an ovarian cancer, a stage of a hepatobiliary cancer, a stage of a melanoma, a stage of a cervical cancer, a stage of a multiple myeloma, a stage of a leukemia, a stage of a thyroid cancer, a stage of a bladder cancer, or a stage of a gastric cancer (4064).

In some embodiments, classifying the cancer class of each respective subject includes determining a type of a cancer present in the respective subject (4066). In some embodiments, one or more respective subjects have already been diagnosed with cancer and method 4000 is performed to determine a type of the cancer. In some embodiments, one or more subjects have not been diagnosed with cancer and method 4000 is performed to determine whether the respective subjects have cancer and, if so, the type of the cancer. In some embodiments, the type of cancer is breast cancer, lung cancer, prostate cancer, colorectal cancer, renal cancer, uterine cancer, pancreatic cancer, cancer of the esophagus, a lymphoma, head/neck cancer, ovarian cancer, a hepatobiliary cancer, a melanoma, cervical cancer, multiple myeloma, leukemia, thyroid cancer, bladder cancer, or gastric cancer (4068).

In some embodiments, classifying the cancer class of each respective subject includes determining a prognosis for a cancer in the respective subject (4070), e.g., a life expectancy without treatment, a life expectancy with treatment, or an expected response to a particular therapy. In some embodiments, the prognosis is a survival statistic, e.g., a cancer-specific survival statistic (e.g., 1-year, 2-year, 5-year, 10-year, 20-year, or other survival time), a relative survival statistic (e.g., 1-year, 2-year, 5-year, 10-year, 20-year, or other survival time), an overall survival statistic (e.g., 1-year, 2-year, 5-year, 10-year, 20-year, or other survival time), or a disease-free survival statistic (e.g., 1-year, 2-year, 5-year, 10-year, 20-year, or other recurrence-free or progression-free survival time). In some embodiments, the prognosis is a predicted response to a particular therapeutic regimen.

In some embodiments, the classifier is a multinomial classifier that provides a plurality of likelihoods responsive to the identification of the relative copy number at each respective genomic location, where each respective likelihood in the plurality of likelihoods is a likelihood that the test subject has a corresponding cancer class in a plurality of cancer classes (4072). In some embodiments, the classifier is a multivariate logistic regression algorithm, a neural network algorithm, or a convolutional neural network algorithm (4074). In some embodiments, the classifier is a neural network algorithm, a support vector machine algorithm, a Naive Bayes algorithm, a nearest neighbor algorithm, a boosted trees algorithm, a random forest algorithm, a convolutional neural network algorithm, a decision tree algorithm, a regression algorithm, or a clustering algorithm (4076).

In some embodiments, the classifier uses a linear or non-linear combination of the relative copy number at two or more respective genomic locations in the plurality of genomic locations (4078).

In some embodiments, the linear or non-linear combination of the relative copy number at two or more respective genomic locations is identified (4080) by subjecting the relative copy number at each respective genomic position in the precursor set across a training set of electronic sequence reads to a dimension reduction technique. In some embodiments, the dimension reduction algorithm is a linear dimension reduction algorithm or a non-linear dimension reduction algorithm (4082). In some embodiments, the dimension reduction algorithm is a linear dimension reduction algorithm selected from the group consisting of a principal component analysis algorithm and a factor analysis algorithm (4084). In some embodiments, the dimension reduction algorithm is a non-linear dimension reduction algorithm selected from the group consisting of Sammon mapping, curvilinear components analysis, a stochastic neighbor embedding (SNE) algorithm, an Isomap algorithm, a maximum variance unfolding algorithm, a locally linear embedding algorithm, and a t-SNE algorithm (4086). In some embodiments, the dimension reduction algorithm is a non-negative matrix factorization algorithm, a kernel principal component analysis algorithm, a graph-based kernel principal component analysis algorithm, a linear discriminant analysis algorithm, or a generalized discriminant analysis algorithm (4088). In some embodiments, the dimension reduction algorithm is uniform manifold approximation and projection (UMAP) algorithm, a LargeVis algorithm, a Laplacian Eigenmap algorithm, or a Fisher's linear discriminant analysis algorithm (4090).

In some embodiments, the classifying further includes applying the identity of an allele at a locus in the genome of a respective subject to the classifier (4092). In some embodiments, the identity of the allele is determined from the size-selected sequencing reads, e.g., generated according to step 2010 or 2110 as described above. In some embodiments, the identity of the allele is determined from a separate sequencing reaction, e.g., from a different sample and/or performed at an earlier time.

In some embodiments, the classifying further includes applying a methylation state at a locus in the genome of a respective subject to the classifier (4094). In some embodiments, the methylation state at the locus is determined from the size-selected sequencing reads, e.g., generated according to step 2010 or 2110 as described above. In some embodiments, the methylation state at the locus is determined from a separate sequencing reaction, e.g., from a different sample and/or performed at an earlier time.

In some embodiments, the cancer class of the respective subject is determined with a first degree of confidence, and the first degree of confidence is greater than a second degree of confidence obtainable by application of genetic information consisting of relative copy number at each respective genomic location in the plurality of genomic locations obtained from a second plurality of sequence reads from the biological sample, to the classifier, where the second plurality of sequence reads encodes (i) cell-free DNA molecules that are shorter than the first threshold length and (ii) cell-free DNA molecules that are longer than the first threshold length (4096). That is, the confidence with which the cancer class is determined is greater when the size-selected sequencing reads are used than it would have been had the cancer class been determined from sequence reads generated against all cfDNA fragments in the sample (not size-selected). In some embodiments, while the determination of cancer classes associated with a positive diagnosis for a cancer in the subject is made with a greater confidence using the size-selected sequence reads, determinations of a cancer class associated with a diagnosis that the subject does not have cancer are not made with a greater confidence than if a set of non-size-selected sequence reads were used. That is, in some embodiments, the methods provided herein result in cancer classification that are made with greater confidence when the subject has cancer, but with a similar or lower confidence when the subject does not have cancer. This, of course, does not require that the classification with a full set of sequence reads from a biological sample is actually performed, or that the second confidence is actually calculated.

In some embodiments, however, the second classification and/or confidence is determined. For example, in some embodiments, method 4000 includes obtaining (4098) the second plurality of sequence reads from the biological sample, using the second plurality of sequence reads to identify a relative copy number at each respective genomic location in the plurality of genomic locations in the genome of the subject, and classifying the subject, where the classifying includes applying genetic information about the subject obtained from the biological sample, where the genetic information is the relative copy number at each respective genomic location in the plurality of genomic locations obtained from a second plurality of sequence reads from the biological sample, to the classifier, thereby determining the cancer class of the subject with the second confidence.

In some aspects, the present disclosure provides systems and methods for classifying a renal cancer, glioblastoma, bladder cancer, or pancreatic cancer by excluding sequencing data, e.g., either in vitro or in silico, from cfDNA fragments having lengths that are longer than a threshold length, where the threshold length is no more than 160 nucleotides. Advantageously, it was unexpectedly found that the fraction of sequence reads from renal, glioblastoma, bladder, and pancreatic cancer-derived cfDNA could be enriched approximately two-fold using the size-selection methodologies described herein. In some embodiments, classification methodologies that invoke this size selection rely on one or more of copy number variation, allele variants, and methylation status determined from the size-selected sequencing data.

Accordingly, in one embodiment, a method for determining whether a subject has cancer, e.g., renal cancer, glioblastoma, bladder cancer, or pancreatic cancer, is provided. The method is performed at a computer system having one or more processors, and memory storing one or more programs for execution by the one or more processors. The method includes obtaining a first plurality of sequence reads, in electronic form, from a biological sample of the subject. The biological sample includes a first plurality of cell-free DNA molecules including respective DNA molecules that are longer than a first threshold length, where the first threshold length is less than 160 nucleotides. The first plurality of sequence reads excludes sequence reads of cell-free DNA molecules in the first plurality of cell-free DNA molecules longer than the first threshold length. The method then includes using the first plurality of sequence reads to identify a relative copy number at each respective genomic location in a plurality of genomic locations in the genome of the subject, e.g., where the plurality of genomic locations includes at least fifty genomic locations. The method then includes classifying the subject by applying the identification of the relative copy number at each respective genomic location to a classifier, thereby determining a cancer class of the subject. In some embodiments, the cancer class of the subject is a presence of a cancer. In some embodiments, the cancer class is a presence of a cancer selected from renal cancer, glioblastoma, bladder cancer, and pancreatic cancer.

In another embodiment, a method is provided for determining a stage of a renal cancer, glioblastoma, bladder cancer, or pancreatic cancer in a subject. The method is performed at a computer system having one or more processors, and memory storing one or more programs for execution by the one or more processors. The method includes obtaining a first plurality of sequence reads, in electronic form, from a biological sample of the subject. The biological sample includes a first plurality of cell-free DNA molecules including respective DNA molecules that are longer than a first threshold length, where the first threshold length is less than 160 nucleotides. The first plurality of sequence reads excludes sequence reads of cell-free DNA molecules in the first plurality of cell-free DNA molecules longer than the first threshold length. The method hen includes using the first plurality of sequence reads to identify a relative copy number at each respective genomic location in a plurality of genomic locations in the genome of the subject, e.g., where the plurality of genomic locations includes at least fifty genomic locations. The method then includes classifying the subject by applying the identification of the relative copy number at each respective genomic location to a classifier, thereby determining a cancer class of the subject. In some embodiments, the cancer class of the subject is a stage of a cancer selected from renal cancer, glioblastoma, bladder cancer, and pancreatic cancer.

In another embodiment, a method is provided for determining a prognosis for a renal cancer, glioblastoma, bladder cancer, or pancreatic cancer in a subject. The method is performed at a computer system having one or more processors, and memory storing one or more programs for execution by the one or more processors. The method includes obtaining a first plurality of sequence reads, in electronic form, from a biological sample of the subject. The biological sample comprises a first plurality of cell-free DNA molecules including respective DNA molecules that are longer than a first threshold length, where the first threshold length is less than 160 nucleotides. The first plurality of sequence reads excludes sequence reads of cell-free DNA molecules in the first plurality of cell-free DNA molecules longer than the first threshold length. The method then includes using the first plurality of sequence reads to identify a relative copy number at each respective genomic location in a plurality of genomic locations in the genome of the subject, e.g., where the plurality of genomic locations comprises at least fifty genomic locations. The method then includes classifying the subject by applying the identification of the relative copy number at each respective genomic location to a classifier, thereby determining a cancer class of the subject. In some embodiments, the cancer class of the subject is a prognosis for a cancer selected from renal cancer, glioblastoma, bladder cancer, and pancreatic cancer.

The details of the implementation of other methods described herein (e.g., methods 2000, 2100, 3000, and 4000) are also applicable in an analogous manner to the methods described above for classifying a renal cancer, glioblastoma, bladder cancer, or pancreatic cancer. For instance, the methodology used to construct cfDNA libraries, in vitro size-select cfDNA molecules, sequence the cfDNA libraries, process sequence reads, in silico filter the sequence reads, and/or classify a sample based on the sequencing data described above with respect to methods 2000, 2100, 3000, and 4000 are also applicable in an analogous manner to the methods described above for classifying a renal cancer, glioblastoma, bladder cancer, or pancreatic cancer. Further the operations in the information processing methods described above are, optionally, implemented by running one or more functional modules in information processing apparatus such as general purpose processors (e.g., as described above with respect to FIG. 1) or application-specific chips.

EXAMPLES

The data used in the analyses presented in Examples 1-6 below was collected as part of the CCGA clinical study. The CCGA [NCT02889978] is the largest study of cfDNA-based early cancer detection. This prospective, multi-center, observational study has enrolled over 10,000 demographically-balanced participants across 141 sites, including healthy individuals and cancer patients across at least 20 tumor types and all clinical stages. All samples were analyzed by: 1) Paired cfDNA and white blood cell (WBC)-targeted sequencing (60,000×, 507 gene panel), using a joint caller to remove WBC-derived somatic variants and residual technical noise; 2) Paired cfDNA and WBC whole-genome sequencing (WGS) at approximately 35× sequence coverage; and 3) cfDNA whole-genome bisulfite sequencing (WGBS) at approximately 34× sequence coverage, using abnormally methylated fragments to normalize scores.

Cell-free DNA was isolated from the collected blood samples and then sequenced, as described above, to provide the cfDNA sequencing data. Likewise, blood cells were isolated using a buffy coat separation method and genomic preparations from the white blood cells were then sequenced to provide a matching sequence reads of the loci of interest, e.g., for positive assignment of sequence variants arising from clonal hematopoiesis.

The cancer types included in the CCGA study included invasive breast cancer, lung cancer, colorectal cancer, DCIS, ovarian cancer, uterine cancer, melanoma, renal cancer, pancreatic cancer, thyroid cancer, gastric cancer, hepatobiliary cancer, esophageal cancer, prostate cancer, lymphoma, leukemia, multiple myeloma, head and neck cancer, and bladder cancer.

Example 1—Distribution of Cell-Free DNA Fragments in Cancer Patients

The distribution of cell-free DNA fragment lengths, as determined by whole genome sequencing (WGS) was investigated in cell-free DNA samples from subjects having varying tumor fractions. Briefly, WGS results from 747 healthy individuals and 1001 confirmed cancer patients from the CCGA study, as described above, were plotted as a function of the tumor fraction of the subject. FIG. 5 shows average distributions of cell-free DNA fragment length from 747 healthy subjects (502), 708 cancer patients with tumor fractions of less than 1% (504), 136 cancer patients with tumor fractions between 1-5% (506), 61 cancer patients with tumor fractions between 5-10% (508), 73 cancer patients with tumor fractions between 10-25% (510), 22 cancer patients with tumor fractions between 25-50% (512), and 1 cancer patient with a tumor fraction between 50-100% (514). As can be seen in FIG. 5, the distribution of lengths of cell-free DNA fragments is shifted shorter as a function of the tumor fraction of the patient. That is, the tumor fraction of the subject correlates with the magnitude of the cell-free DNA fragment length shift. This represents a difference in biology between cancer and healthy cells, in which cell-free DNA originating from cancer cells is shorter in length than cell-free DNA originating from healthy cells.

Example 2—Probabilistic Model of Cancer-Cell Origin as a Function of Fragment Length To investigate whether cell-free DNAs of any particular fragment lengths may be more or less likely to have originated from a cancer cell, as opposed to a healthy cell, a Bayesian probabilistic model of the likelihood that a fragment is derived from a cancer cell was generated. Briefly, sequencing data generated from samples of a few patients with very high tumor fractions of greater than 50%, from the CCGA study described above, was used to generate the model because these samples provided a great enough mass of smaller fragments for the analysis. As can be seen by the model shown in FIG. 6, it is likely that more cancer-derived fragments will be observed at shorter fragments lengths than at longer fragment lengths. This probability model suggests that sequencing data from cell-free DNA fragment having lengths below 150 nucleotides will be enriched for cancer-derived sequences, relative to all sequencing data generated from the sample. This model also suggests that sequencing data from cell-free DNA fragments having lengths below 100 nucleotides will be even further enriched for cancer-derived sequences.

Example 3—Genomic Sequence Coverage Following in Silico Size-Selection

Figure 7A:
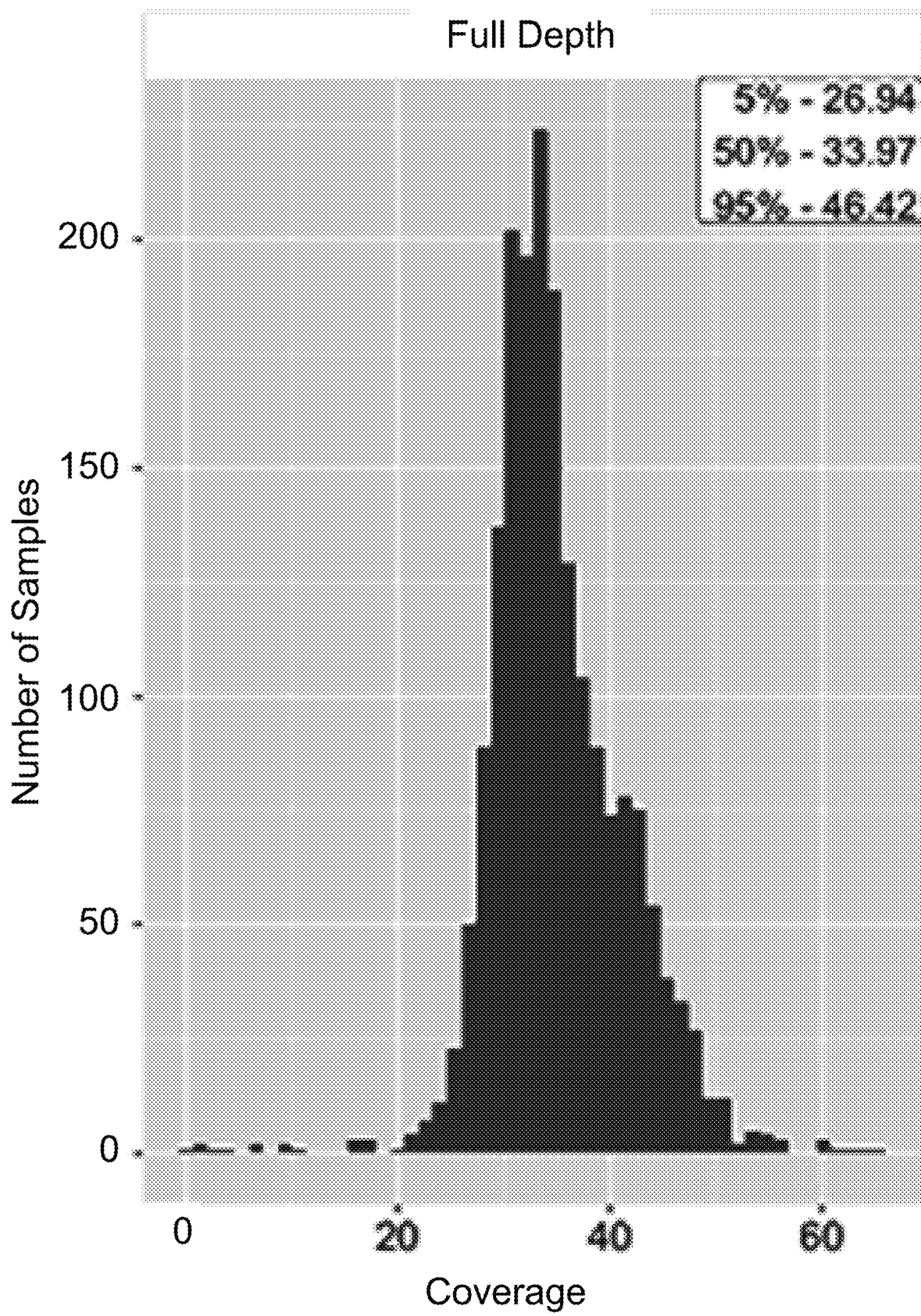
FIGS. 7A, 7B, and 7C illustrate histograms of sequencing coverage obtained from whole genome sequencing of cfDNA samples when unfiltered (FIG. 7A), filtered in silico to only include sequences from cfDNA fragments having a size of from 90 to 150 nucleotides (FIG. 7B), and filtered in silico to only include sequences from cfDNA fragments having a size of 100 nucleotides or less (FIG. 7C).
Figure 7B:
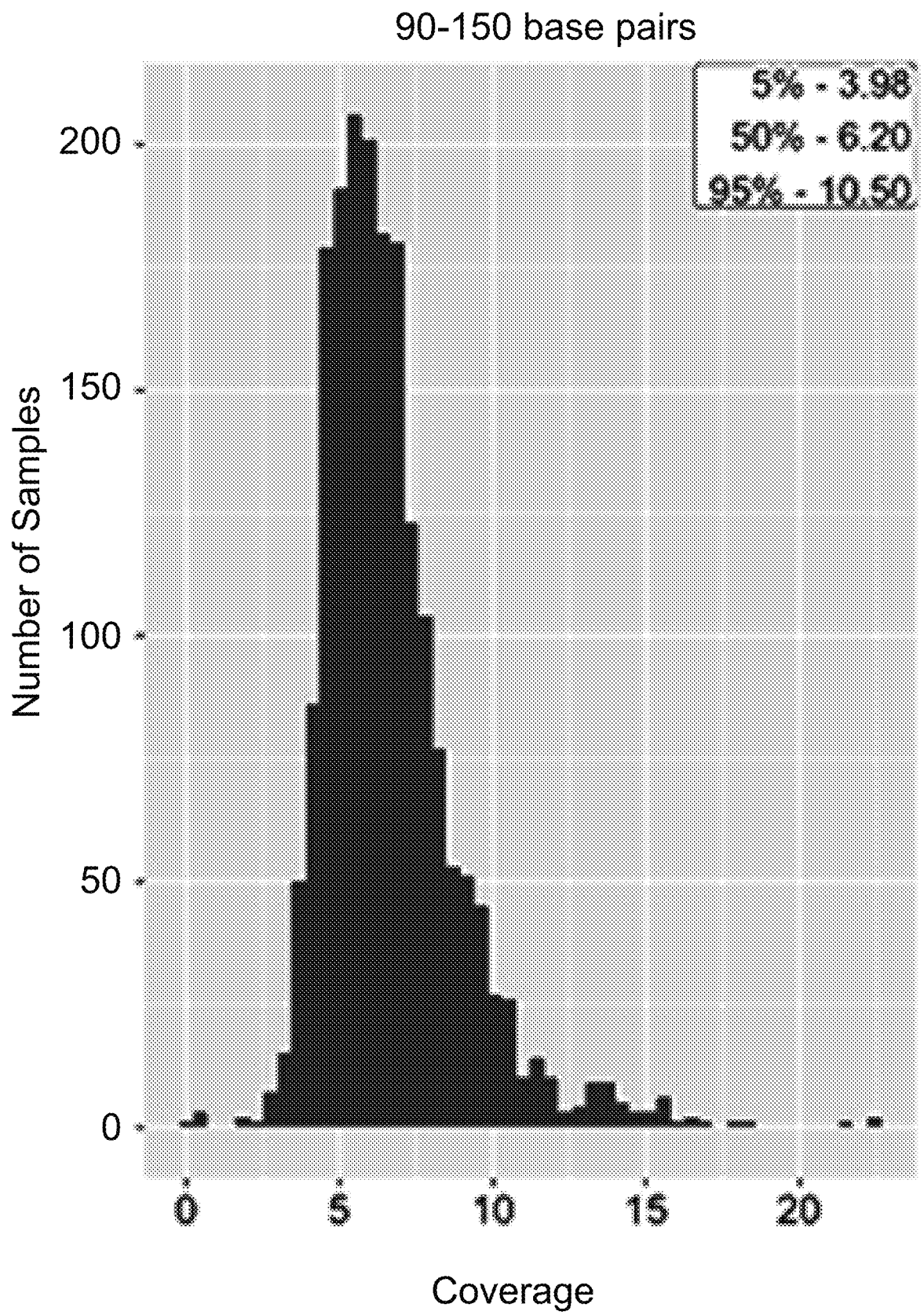
Figure 7C:
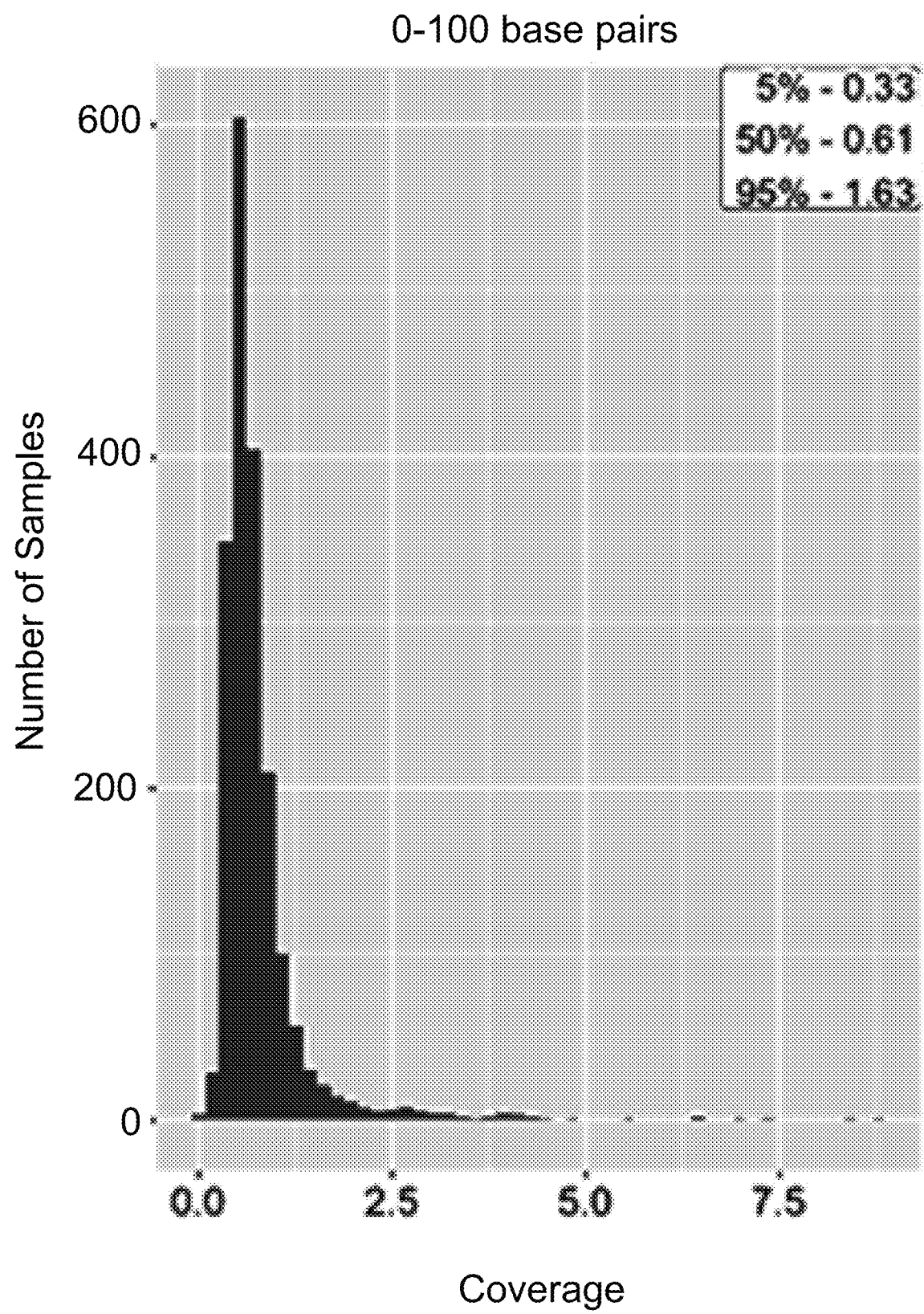

Next, the sequence coverage obtained after size-selecting data generated by whole genome sequencing (WGS) of cell-free DNA samples was investigated. Briefly, sequencing data obtained from the CCGA study described above was filtered in silico to include only sequences obtained from cfDNA fragments having a size of from 90 to 150 nucleotides (FIG. 7B) or only sequences generated from cfDNA fragments having a size of 100 nucleotides or less (FIG. 7C). The average sequence coverage was then calculated for the unfiltered data set, the data set filtered to include only sequences from cfDNA fragments of 90 to 150 nucleotides, and the data set filtered to include only sequences from cfDNA fragments of 100 nucleotides or less. As shown by the histograms illustrated in FIG. 7, the unfiltered CCGA data sets had a median sequence coverage of about 34× (FIG. 7A), the data sets filtered to sequences from cfDNA fragments of 90 to 150 nucleotides had a median sequence coverage of about 6×, and the data sets filtered to sequences from cfDNA fragments of 100 nucleotides or less had a median sequence coverage of about 0.6×. Fifth and Ninety-fifth percentiles for each distribution are also shown in FIG. 7.

Example 4—Cancer Classification Following in Silico Size-Selection

Although selection of sequence reads generated from smaller cfDNA fragments (e.g., less than 150 nucleotides) should enrich for cancer-derived fragments in samples from cancer patients, this selection will result in a net loss of information about the cancer because some of the larger cfDNA fragments that are removed will be derived from the cancer. Thus, although cancer-derived fragments are enriched relative to non-cancer derived fragments in the size-selected data set, it was theorized that the overall diagnostic power of the data set would be reduced relative to the full data set. In order to test whether this was the case, the data sets filtered as described in Example 3 were input into a cancer classifier trained against copy number variation across a plurality of predetermined genomic bins, each representing a predefined portion of the human genome, as described herein and with reference to U.S. Provisional Patent Application Ser. No. 62/642,461, filed on Mar. 13, 2018, and entitled METHOD AND SYSTEM FOR SELECTING, MANAGING, AND ANALYZING DATA OF HIGH DIMENSIONALITY, the content of which is incorporated herein by reference, in its entirety, for all purposes.

Briefly, CCGA data sets of sequence reads from cancer patients and healthy subjects, excluding uterine, thyroid, prostate, melanoma, renal, and HR+ stage I/II breast cancers, were filtered as described in Example 3, to either select sequence reads from cfDNA having lengths of 90-150 nucleotides or sequence reads from cfDNA having lengths of 100 nucleotides or less. The filtered data was then normalized within the filtered data sets, and the normalized data for each filtered sample input into a logistic regression classifier trained against features of low-variance genomic bin counts. To control for the difference in sequence coverage between the filtered and unfiltered data sets, as reported in Example 3, control data sets were generated by size-independently selecting sequence reads at random from the unfiltered data set to achieve the same sequence coverage as the corresponding size-selected data set, e.g., having a median sequence coverage of about 6.2× for the 150-90 nucleotide control data sets and about 0.6× median sequence coverage for the 0-100 nucleotide control data set.

Classifications were then generated for each unfiltered, control, and size-selected data sets at 95% specificity and 99% specificity. Fifty rounds of classification were performed using 90-10 splits of CCGA training data, balanced for cancer and non-cancer data sets. The sensitivity of each group of classifications was then generated based on the known status of each subject in the CCGA. The results of these classifications are illustrated in FIG. 8, with the results from the full-depth (unfiltered) data sets illustrated on the left of each grouping (e.g., 802), the results from the sequence-coverage control data sets illustrated in the middle of each grouping (e.g., 804), and the results from the size-selected data sets illustrated on the right of each grouping (e.g., 806).

Figure 8A:
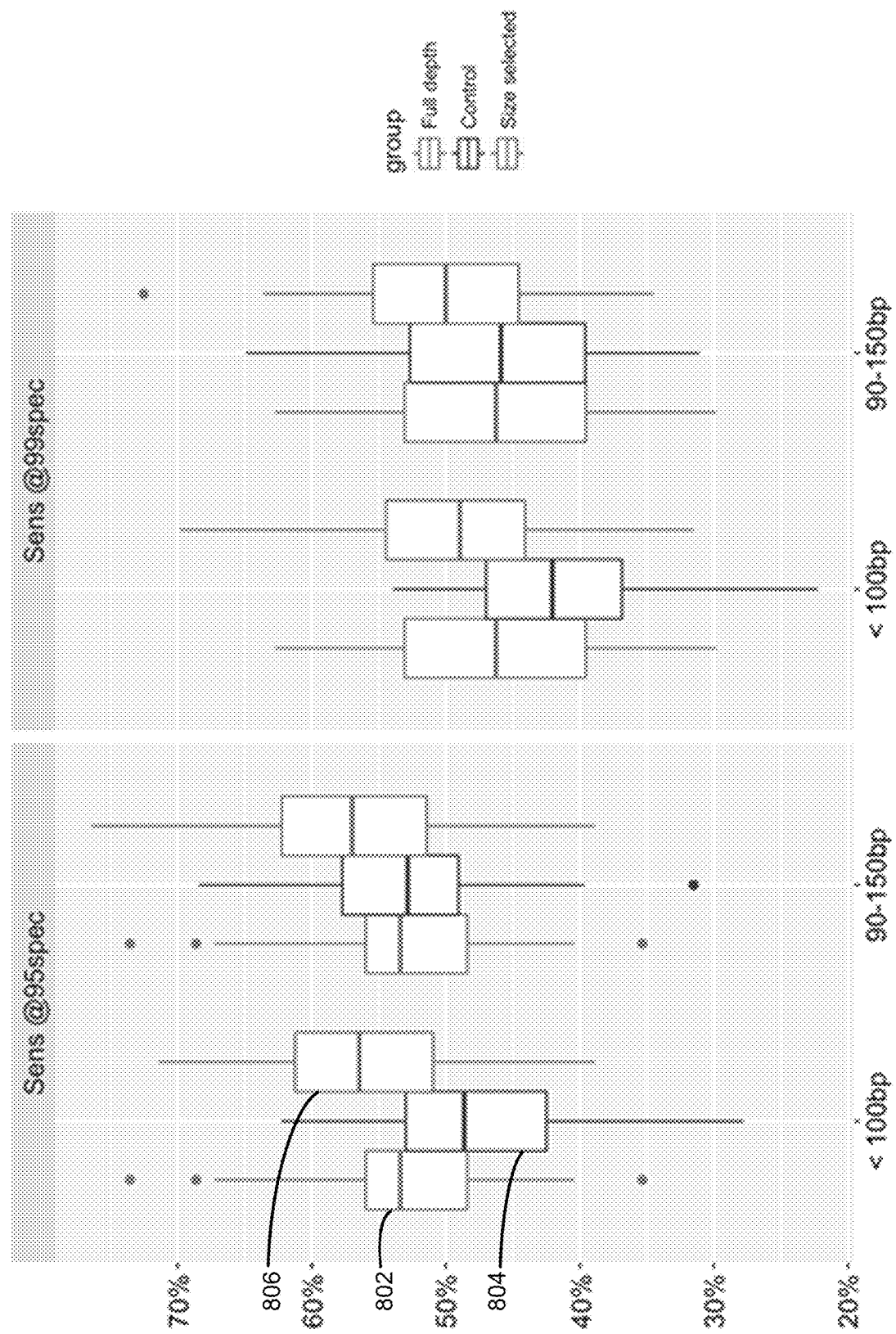
FIG. 8A illustrates box plots of the specificity of cancer classification using full (unfiltered) CCGA WGS data sets, size-selected (filtered) CCGA WGS data sets, and control data sets with randomly selected sequence reads from the full (unfiltered) CCG AWGS data sets to match the sequence coverage of the seize-selected (filtered) CCG AWGS data sets, as described in Example 4.

As compared to the control data sets having the same sequence coverage, the size-selected data sets consistently performed better (compare the right plot of each grouping to the middle plot of each grouping in FIG. 8A). This is consistent with the fact that the size-selected data sets should contain more sequence reads from cancer-derived cfDNA fragments than the control data set. Remarkably, however, both types of size-selected data sets also performed better than the corresponding full data sets, despite having 5- to 50-fold less sequence coverage and containing fewer sequence reads from cancer-derived cfDNA fragments than the control data set (compare the right plot of each grouping to the left plot of each grouping in FIG. 8A).

Example 5—Cancer Classification Following in Silico Size-Selection

Figure 8B:
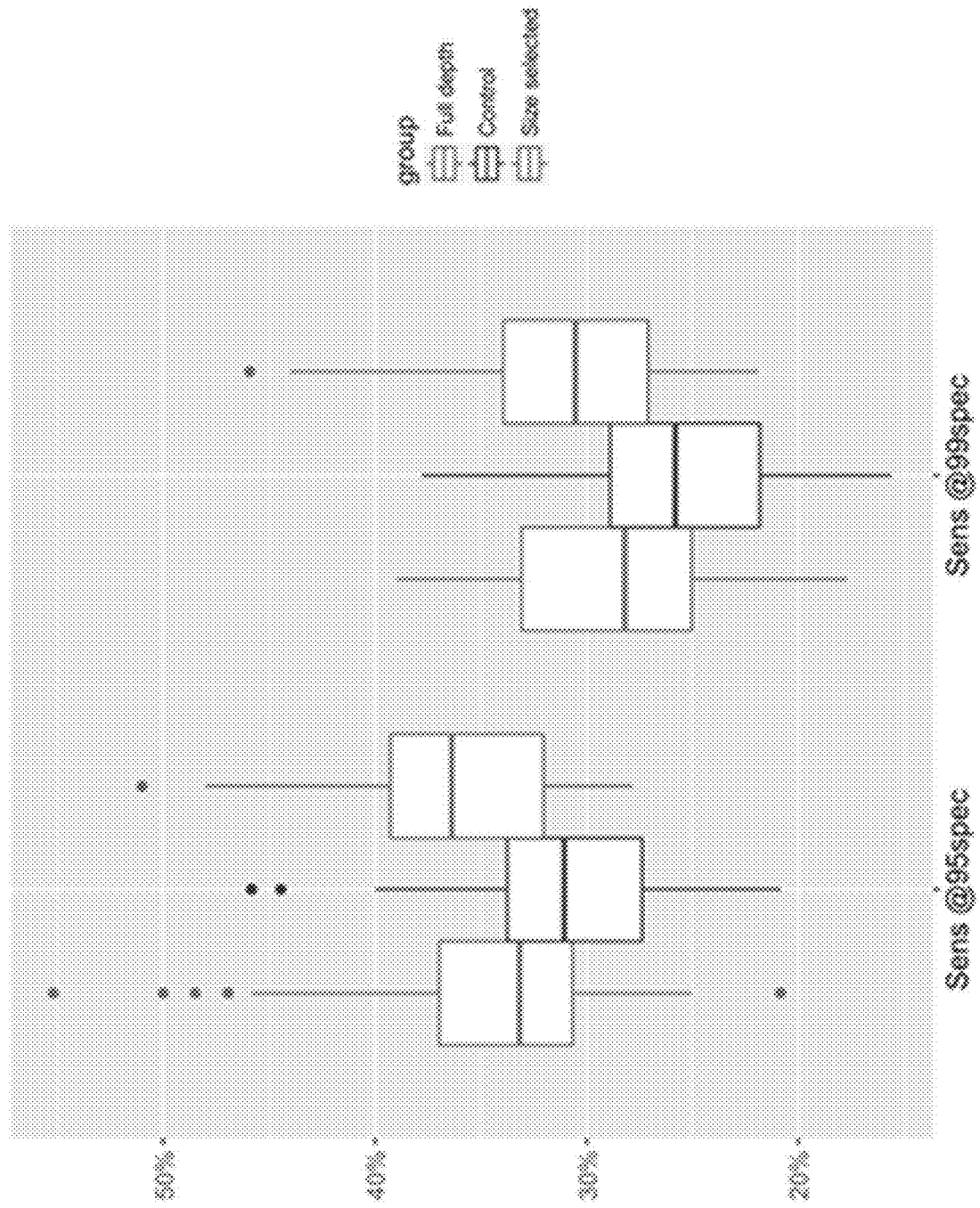
FIG. 8B illustrates box plots of the specificity of cancer classification using full (unfiltered) CCGA WGS data sets, size-selected (filtered) CCGA WGS data sets, and control data sets with randomly selected sequence reads from the full (unfiltered) CCG AWGS data sets to match the sequence coverage of the seize-selected (filtered) CCG AWGS data sets, as described in Example 5.

The analysis outlined in Example 4 was repeated for in silico selection of sequence reads corresponding to cfDNA of 100 nucleotides or less in all cancer types in the CCGA study, e.g., without excluding uterine, thyroid, prostate, melanoma, renal, and HR+ breast cancers. Again, as a control, the full data sets where sub-sampled to sequence coverage matching the sequence coverage of the size-selected data sets. Fifty rounds of classification were performed using 90-10 splits of CCGA training data, balanced for cancer and non-cancer data sets. As shown in FIG. 8B, in silico size selection across all cancer types provided improvements in classification sensitivity at both 95% specificity and 99% specificity, against both the full data sets and the sequence coverage-matched control data sets. The classification statistics for this analysis are presented in Table 1.

TABLE 1

Statistics for cancer classification following in silico filtering of CCGA data sets to sequence reads representing cfDNA fragments with lengths of 100 nucleotides or less.

| | Size select vs. . . . | | | |
|---|---|---|---|---|
| | Subsample | Full depth | Subsample | Size select vs. . . . |
| | | Sens@spec of . . . | | |
| | 95% | | 99% | |
| p-value | 2e−6 | 0.13 | 3e−8 | 4e−3 |
| mean change | 0.051 | 0.013 | 0.052 | 0.023 |
| (2.5%, | (0.032, | (−0.004, | (0.036, | (0.007, |
| 97.5% CI) | 0.069) | 0.031) | 0.067) | 0.038) |

Figure 8C:
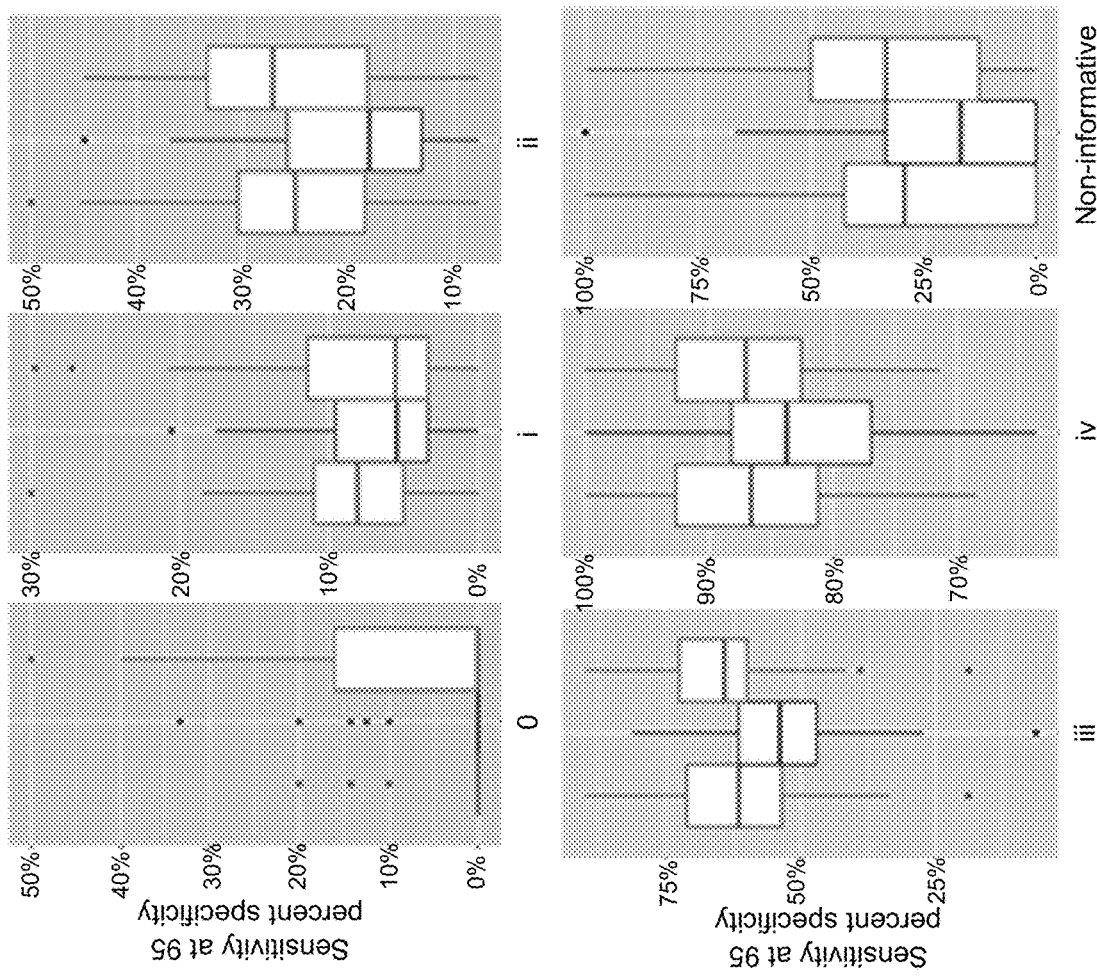
FIGS. 8C and 8D illustrate box plots of the specificity of cancer classification using full (unfiltered) CCGA WGS data sets, size-selected (filtered) CCGA WGS data sets, and control data sets with randomly selected sequence reads from the full (unfiltered) CCG AWGS data sets to match the sequence coverage of the seize-selected (filtered) CCG AWGS data sets, for each cancer stage, as described in Example 5.
Figure 8D:
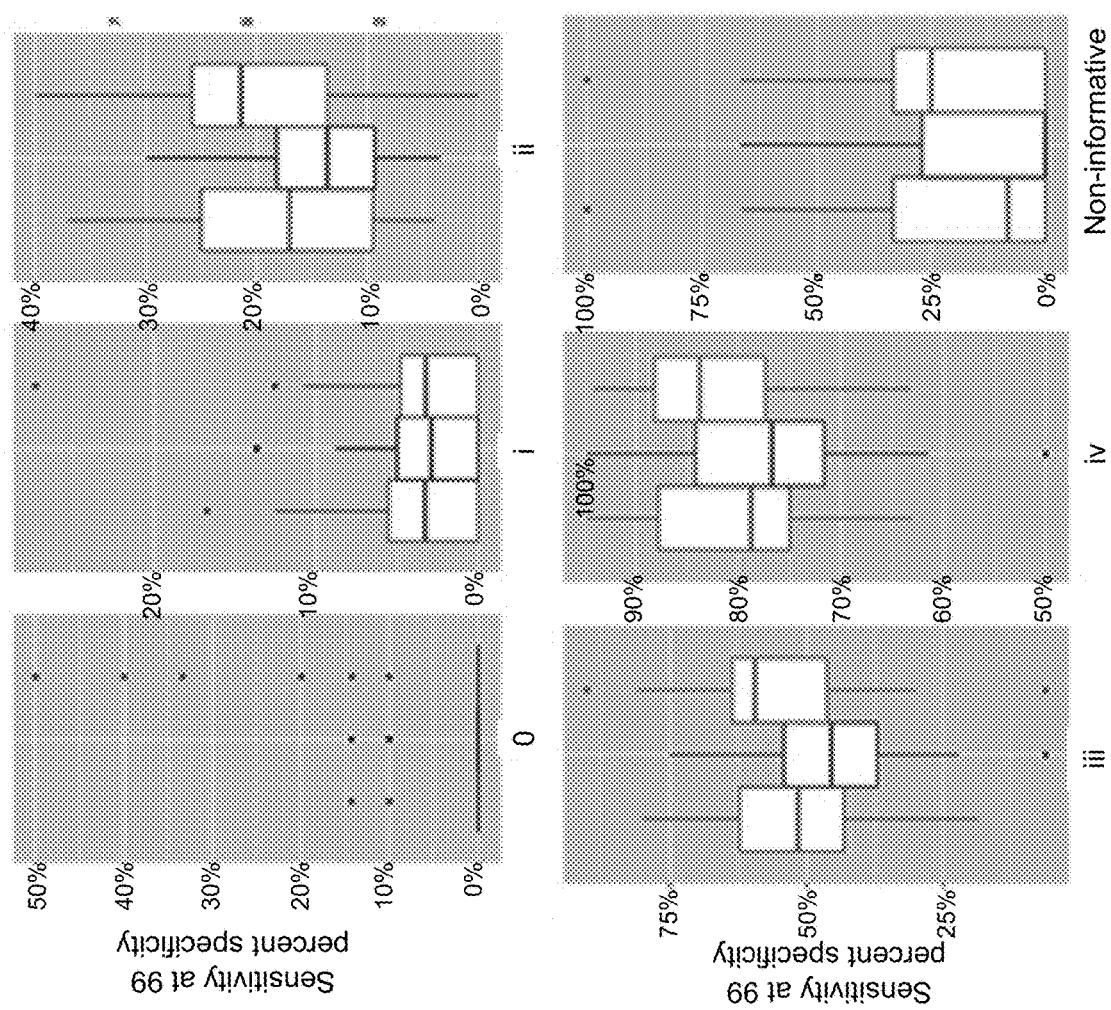

Next, the classification data generated for all cancers above was analyzed with respect to the stage of the cancer. As shown in FIGS. 8C (95% specificity) and 8D (99% specificity), the size-selected data provided equivalent or better sensitivity than the sequence coverage-matched control data sets for all cancer stages at both 95% and 99% specificity. Significantly, the size-selected data provided equivalent or better sensitivity than the full data sets for all cancer stages at both specificities, except for stage 1 cancers determined at 95% specificity. The classification statistics for this analysis are shown in FIG. 8E.

Figure 8F:
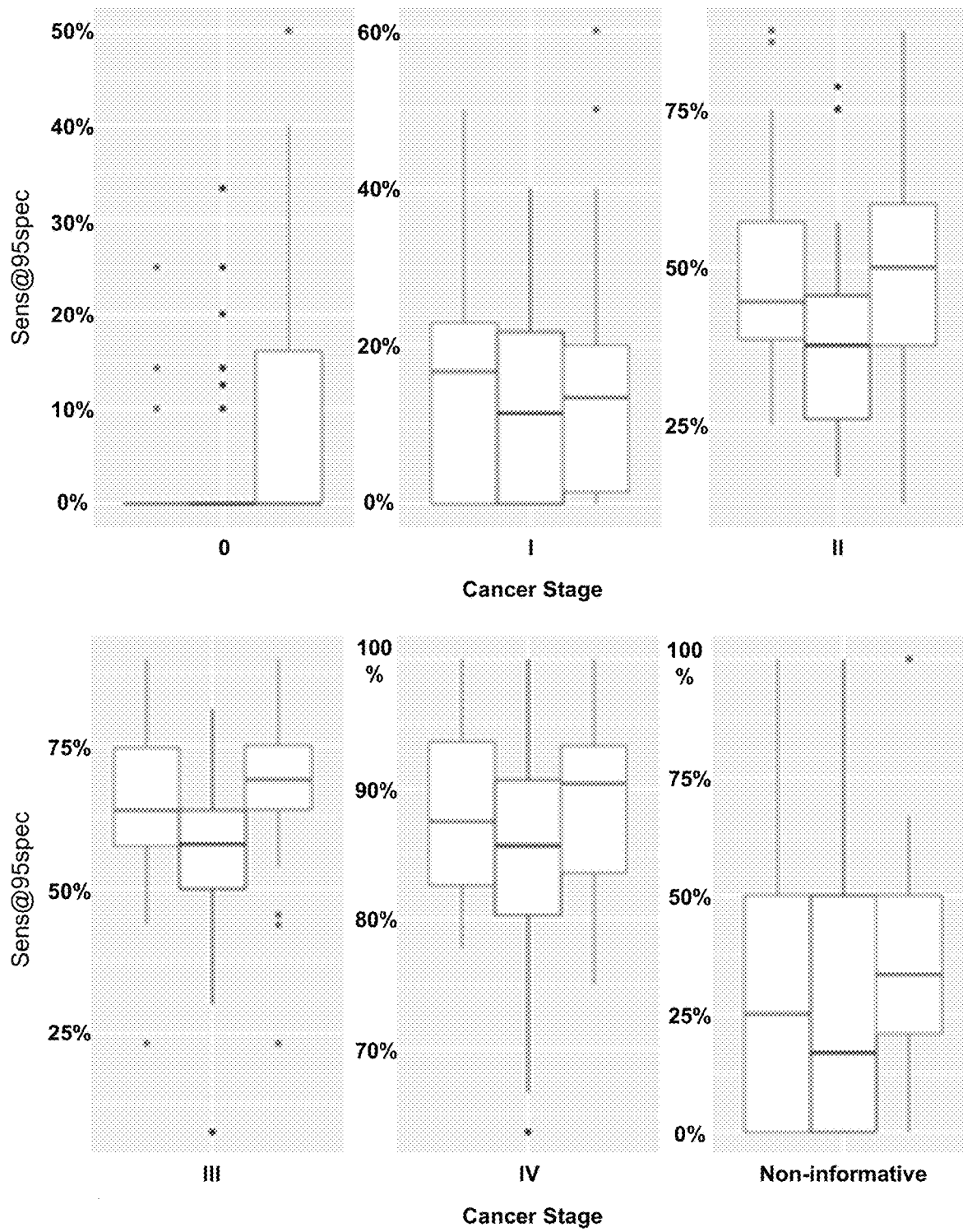
FIGS. 8F and 8G illustrate box plots of the specificity of cancer classification using full (unfiltered) CCGA WGS data sets, size-selected (filtered) CCGA WGS data sets, and control data sets with randomly selected sequence reads from the full (unfiltered) CCG AWGS data sets to match the sequence coverage of the seize-selected (filtered) CCG AWGS data sets, for each cancer stage of cancers that tend to shed more into the bloodstream, as described in Example 5.
Figure 8G:
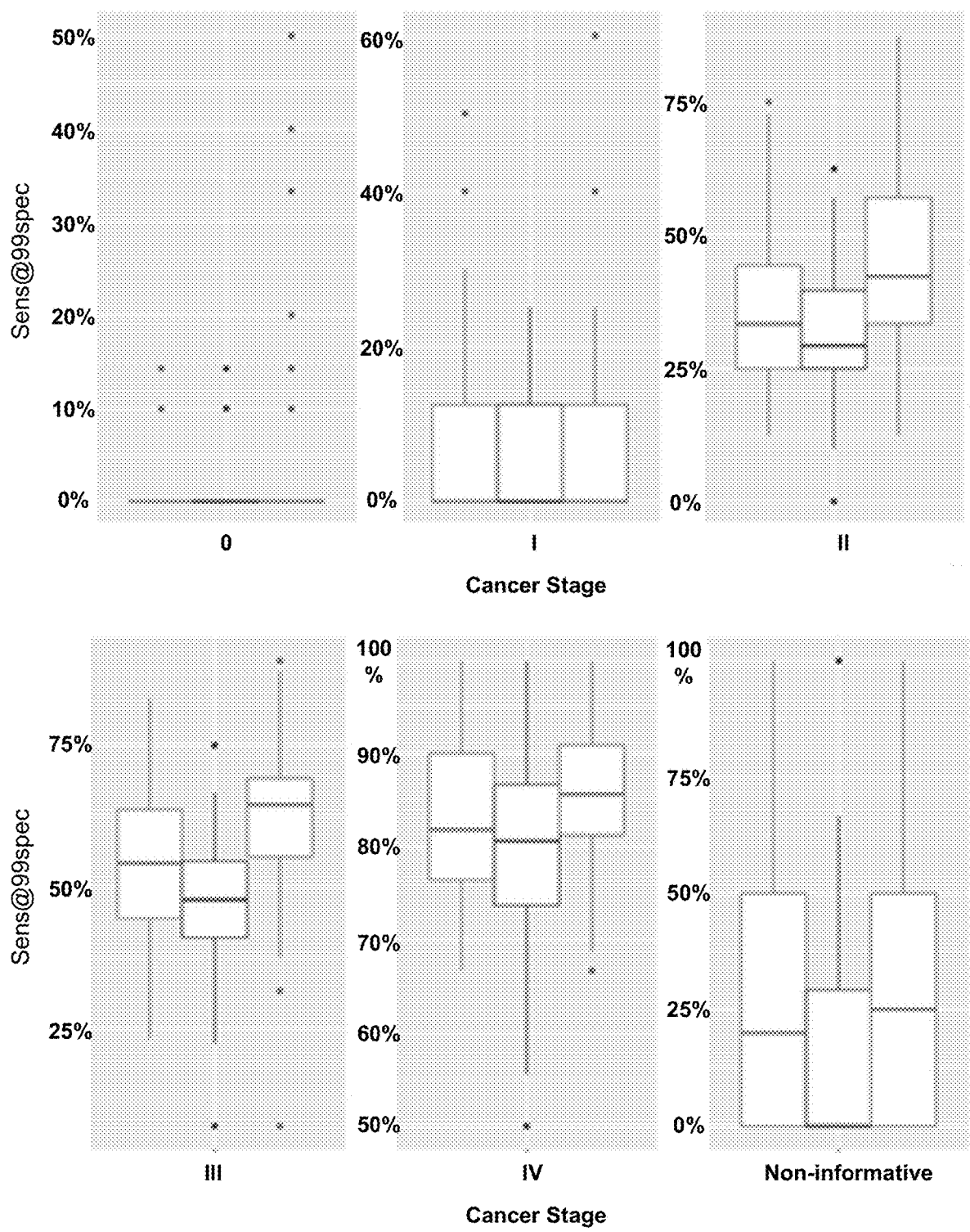

Next, the classification data generated for cancers that tend to shed into the bloodstream, e.g., excluding uterine, thyroid, prostate, melanoma, renal, and HR+ breast cancers, above was analyzed with respect to the stage of the cancer. As shown in FIGS. 8F (95% specificity) and 8G (99% specificity), the size-selected data provided equivalent or better sensitivity than the sequence coverage-matched control data sets for all cancer stages at both 95% and 99% specificity. Significantly, the size-selected data provided equivalent or better sensitivity than the full data sets for all cancer stages at both specificities, except for stage 1 cancers determined at 95% specificity. The classification statistics for this analysis are shown in FIG. 8H.

Example 6—Cancer Classification Following in Silico Size-Selection at Low Sequence Coverage Although the CCGA data sets were generated to a sequencing coverage of about 35×, it was previously observed that no loss of sensitivity occurred when unfiltered (non-size-selected) data sets having 5× sequence coverage were used with the classifier described in Example 4. Accordingly, it was determined whether in silico size selection of sequence reads from a data set with 5× sequence coverage would provide a similar improvement in sensitivity, as demonstrated for size selection of data set having 35× sequence coverage in Example 4.

Briefly, the 35×CCGA data sets used in Example 4 were randomly sub-sampled in a length-independent fashion to approximately 5× sequence coverage, as shown in FIG. 9A. Then, the 5× sub-sampled data sets were filtered to select only those sequence reads from cfDNA fragments having a length of 100 nucleotides or less. As shown in FIG. 9C, these filtered data sets had a median sequence coverage of 0.09×. To control for the difference in sequence coverage between the filtered and unfiltered data sets, control data sets were generated as in Example 4 by size-independently selecting sequence reads at random from the 5× sub-sampled data sets to achieve the same sequence coverage as the corresponding size-selected data set, e.g., having a median sequence coverage of about 0.09×.

Classifications were then generated for each unfiltered, control, and size-selected data sets at 95% specificity and 99% specificity. Fifty rounds of classification were performed using 90-10 splits of CCGA training data, balanced for cancer and non-cancer data sets. The sensitivity of each group of classifications was then generated based on the known status of each subject in the CCGA. The results of these classifications are illustrated in FIG. 9D, with the results from the 5× sub-sampled data sets illustrated on the left of each grouping, the results from the sequence-coverage control data sets illustrated in the middle of each grouping, and the results from the size-selected data sets illustrated on the right of each grouping.

Figure 9D:
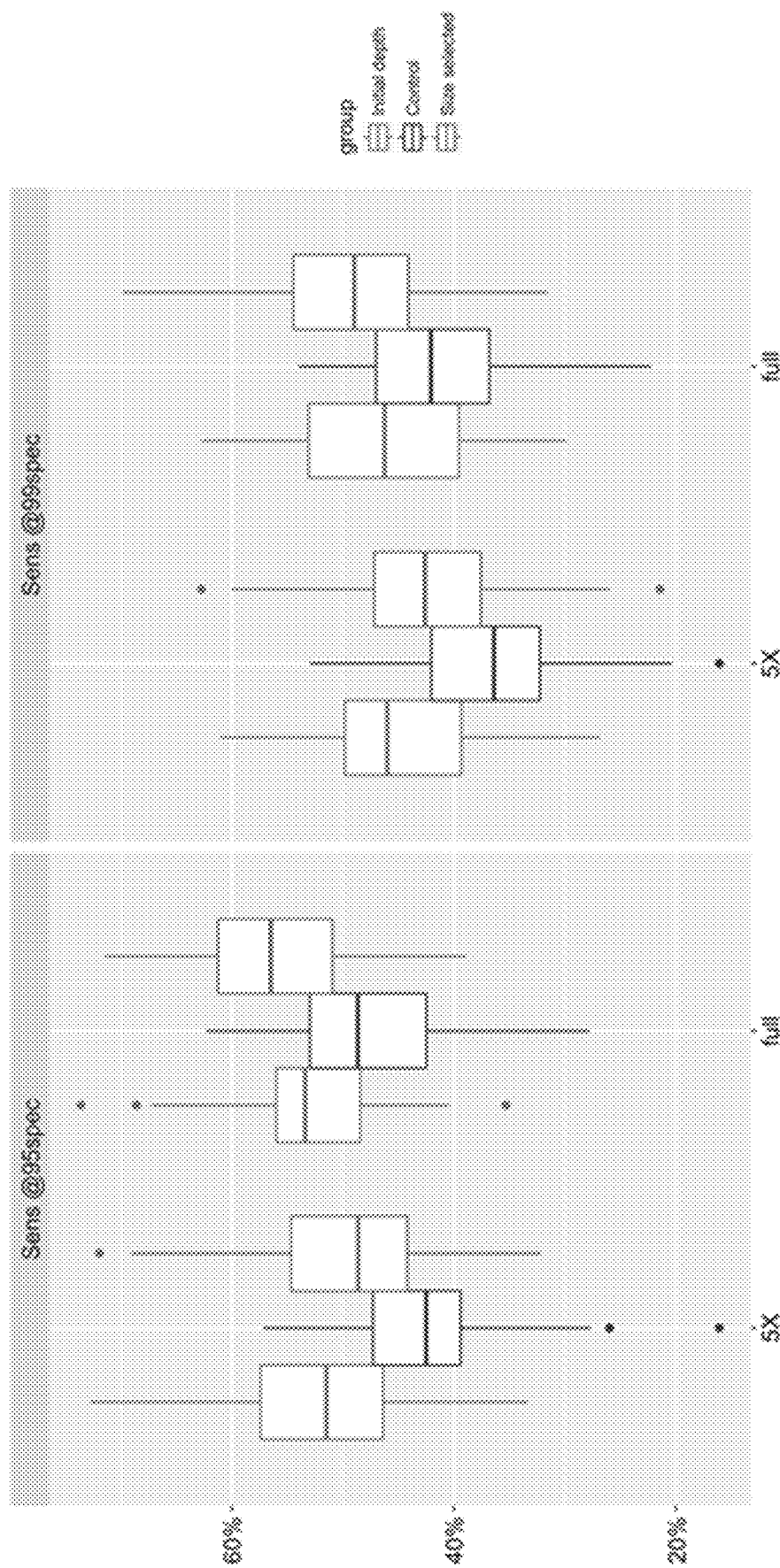
FIG. 9D illustrates box plots of the specificity of cancer classification using full (unfiltered) CCGA WGS data sets sub-sampled to 5× sequence coverage, size-selected (filtered) CCGA WGS data sets from the 5× sub-sampled data sets, and control data sets with randomly selected sequence reads from the full (unfiltered) CCG AWGS data sets sub-sampled to 5× to match the sequence coverage of the seize-selected (filtered) CCG AWGS data sets, as described in Example 6. The corresponding plots generated for the same size-selection in the full 35× samples, as shown in FIG. 8, is displayed for comparison purposes.

As seen in Example 4, the size-selected data sets again performed consistently better than the control data sets (compare the right plot of each grouping to the middle plot of each grouping in FIG. 9D). This is again consistent with the fact that the size-selected data sets should contain more sequence reads from cancer-derived cfDNA fragments than the control data set. However, unlike the case for the 35× sequence coverage data, the size-selected data sets did not improve the sensitivity of the classification as compared to the unfiltered 5× data sets (compare the right plot of each grouping to the left plot of each grouping in FIG. 9D). However, considering the very low sequence coverage of the size-selected data sets, e.g., 0.09× on average, the sensitivity of the classification is quite good, almost replicating the sensitivity of the classification performed at 5× sequence coverage with the unfiltered data.

Example 7—Cancer Classification Following in Silico Size-Selection

Further in silico size selection studies were performed as described in Example 4, starting from the full 35× sequence coverage data sets from the CCGA study. Briefly, size selection was performed to generate filtered data sets of sequence reads from cfDNA fragments having lengths of 100 nucleotides or less, from 90 to 140 nucleotides, or 140 nucleotides or less. As described in Example 4, control data sets randomly sampled to the same sequence coverage, but not sequence-selected, were also generated. The mean sequence coverage for the data sets is shown in FIG. 11. After classification, performed as described in Example 4, it was seen that all three ranges of size-selected data performed equally well, and with better sensitivity than the full data sets at 98% specificity (FIG. 11). In contrast, the control data sets performed worse than the full data sets at 98% specificity (FIG. 11).

Example 8—In Vitro Size-Selection

Figure 10:
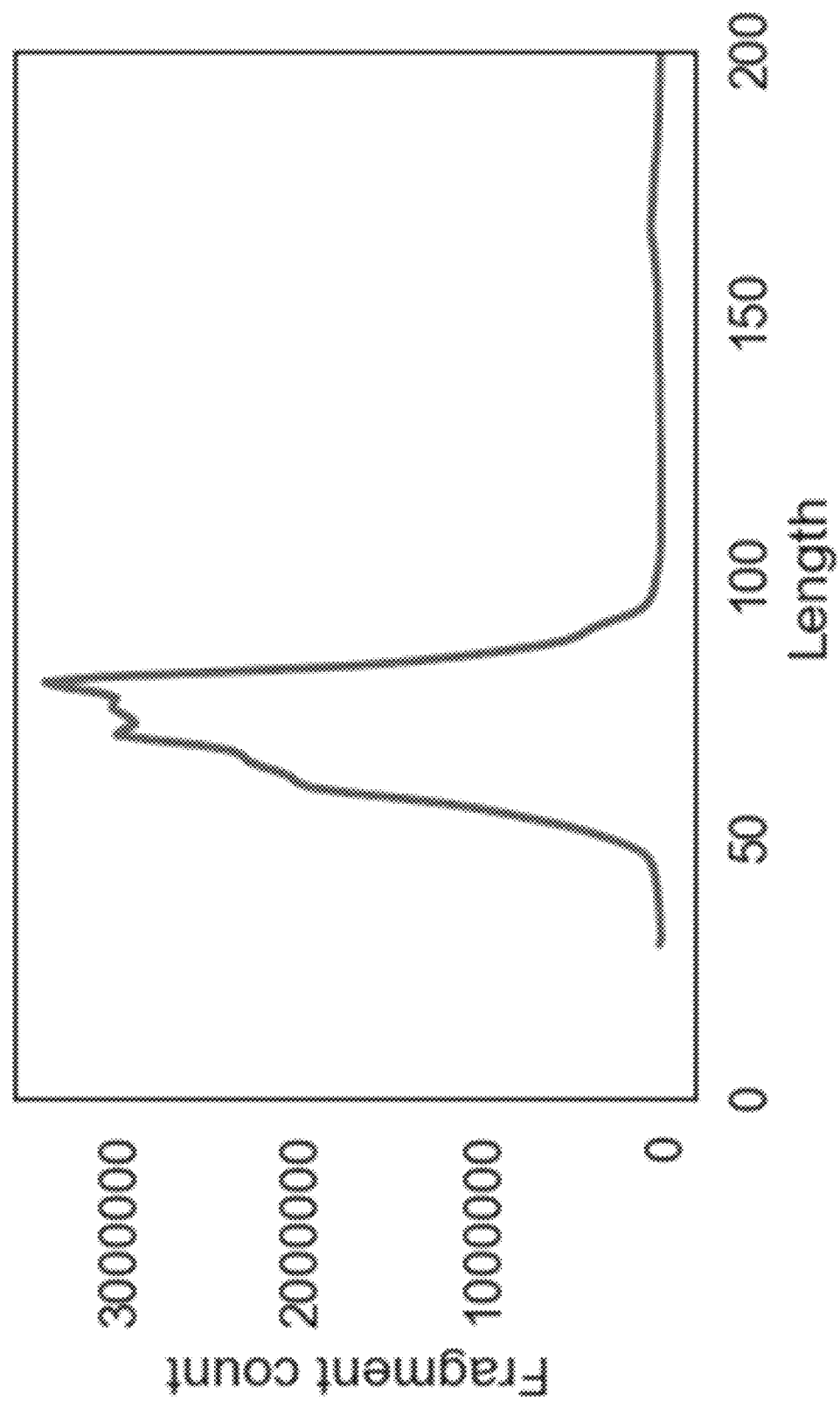
FIG. 10 illustrates the fragment count generated following in vitro size selection of a cfDNA library, as described in Example 8.

It was next determined whether in vitro size selection of DNA fragments prior to sequencing might be a viable alternative to in silico filtering after sequencing. Briefly, a cfDNA library was prepared from a cfDNA sample obtained from a healthy subject with tumor-derived cfDNA titrated in, e.g., as described above with reference to FIG. 2A. The DNA fragments in the cfDNA library were then size selected using a Pipen Prep® agarose gel electrophoretic-based size selection instrument (Sage Science) set at a base pair target value of 0-100+x nucleotides, where x is the number of nucleotides added to the cfDNA fragment during library preparation. The size selected fragments were then sequenced by WGS. As shown in FIG. 10, the generated sequence reads show an appropriate size selection and a sharp cut-off at about 100 nucleotides. Further, when the sequence reads were analyzed, an enrichment in sequence reads of the tumor-derived cfDNA were observed, similar to the in silico size-selection results. Further, other sequencing metrics, e.g., duplication rate and total read loss, were similar to the metrics observed without in vitro size selection.

Example 9—Cancer Classification Following In Vitro Size-Selection

It was next asked whether in vitro size-selection of DNA fragments, prior to sequencing, would provide a similar improvement in classification sensitivity as the in silico size-selection of sequence reads provided in Examples 4-7. Briefly, 65 cancer samples and 29 non-cancer samples were selected from collected CCGA samples across a variety of cancers and cancer stages, as shown in Tables 2 and 3. 38 of the selected cancers were samples of cancers that tend to shed more into the bloodstream.

TABLE 2

Cancer stage of the samples used in the in vitro size selection studies.

| Stage | Count |
|---|---|
| I | 13 |
| II | 15 |
| III | 21 |
| IV | 12 |
| Non-informative | 4 |

TABLE 3

Cancer type of the samples used in the in vitro size selection studies.

| Type | Count | Type | Count |
|---|---|---|---|
| Breast | 18 | Hepatobiliary | 3 |
| Colorectal | 13 | Lymphoma | 3 |
| Lung | 6 | Pancreas | 3 |
| Renal | 5 | Cervix | 2 |
| Head/Neck | 3 | Other | 9 |

Briefly, cfDNA libraries were prepared from the selected samples, as described above with reference to FIG. 2A. Adapters containing UMI sequences, primer hybridization sites, etc., added to the fragments increased the lengths of the cfDNA fragments by approximately 170 nucleotides. In vitro size selection was then performed according to standard protocols using a Pipen Prep® instrument (Sage Science), set to select a size range of either 200-310 nucleotides or 200-320 nucleotides, representing cfDNA fragments of 30-140 or 30-150 nucleotides ligated to 3' and 5' adaptors totaling 170 nucleotides. Sequence reads were then generated for the size-selected libraries, as described above with reference to FIG. 2A.

Figure 13:
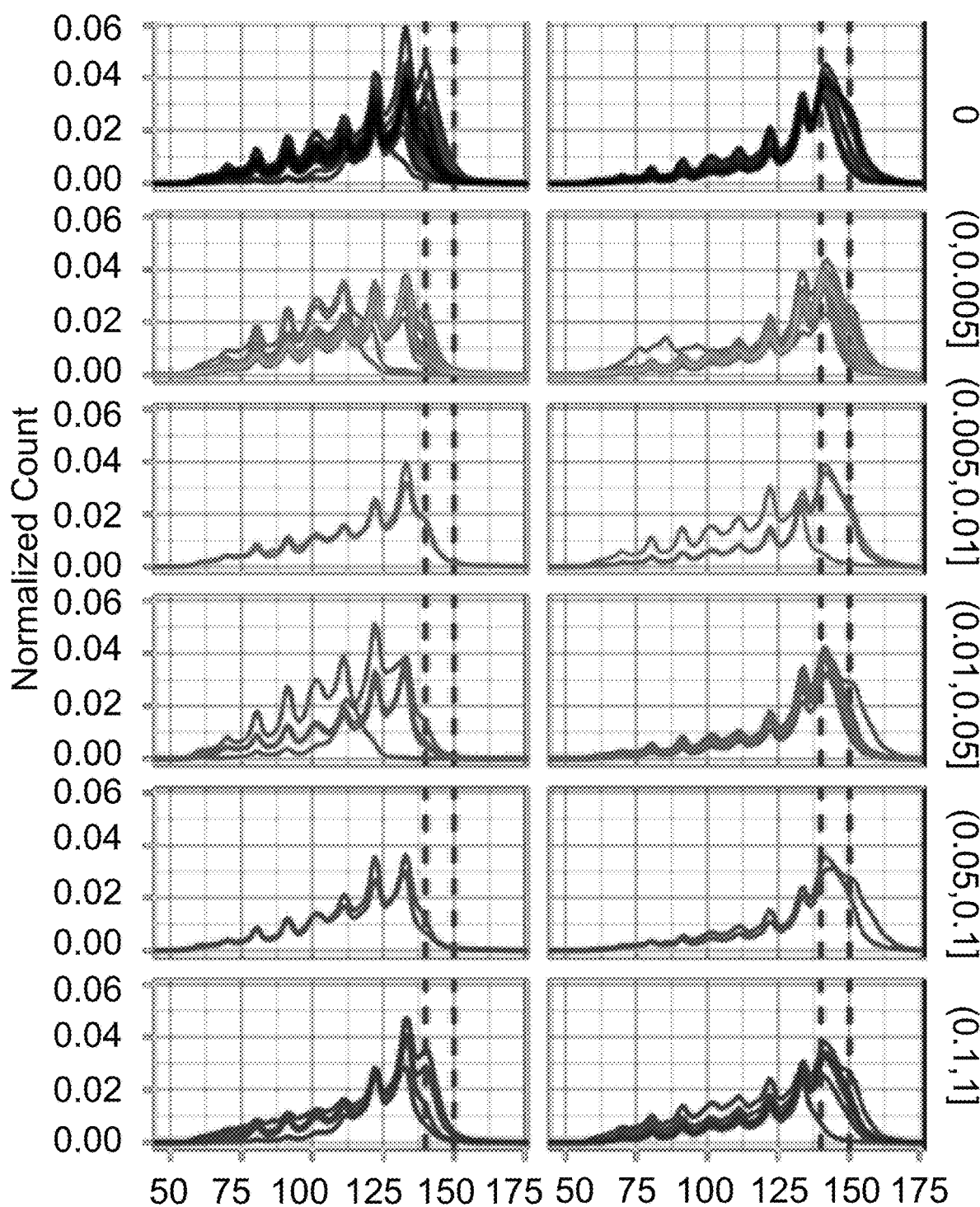
FIG. 13 illustrates the fragment length distribution of individual sequencing reactions of in vitro size selected cfDNA libraries, grouped by tumor fraction, as described in Example 9.

As shown in FIG. 12, there were no unexpected deviations in the sequencing metrics as compared to those generated from the test and training samples for the CCGA study. As expected, removal of longer DNA fragments decreased the average sequence coverage obtained from the samples (FIG. 12A) and total fragment count (FIG. 12C), since less material was available for sequencing. Similarly, size selection resulted in an increase in duplicate fragments lengths (FIG. 12B), again because less template was available for sequencing. As proof of concept, it is shown in FIG. 12D that the average fragment length detected in the size-selected sequencing reactions were reduced. Individual fragment length profiles for the samples are shown in FIG. 13, separated by the tumor fraction of the sample, as shown in parentheses to the right of the traces.

Example 10—Tumor Fraction Determination Following In Vitro Size-Selection

In order to better understand the patterns of enrichment of sequence reads from cancer-derived cfDNA fragments following in silico and in vitro enrichment, performed as discussed above, the fraction of such reads was estimated using cancer-derived variant detection. Briefly, sequencing reactions were performed for cfDNA samples of each of the 65 cancer subjects with and without in vitro size selection either between 30-140 nucleotides or 30-150 nucleotides. Sequencing reactions were also performed against genomic DNA preparations of tumor samples from each of the 35 cancer subjects. The fraction of cancer-derived sequence reads was then estimated by comparing cancer-derived variant alleles identified in the tumor sample with sequence reads of the cell-free DNA either from the size-selected sample or following in silico size selection. As shown in FIG. 14, in vitro size selection to a range of either 30-140 (closed circles) or 30-150 (open circles) nucleotides increased the estimated tumor fraction of almost every sample. In several cases, the increase resulted in a tumor fraction that is above a level of detection for the whole genome sequencing classifier, estimated to be about 0.5%, denoted as the dashed line in the Figure.

Figure 15:
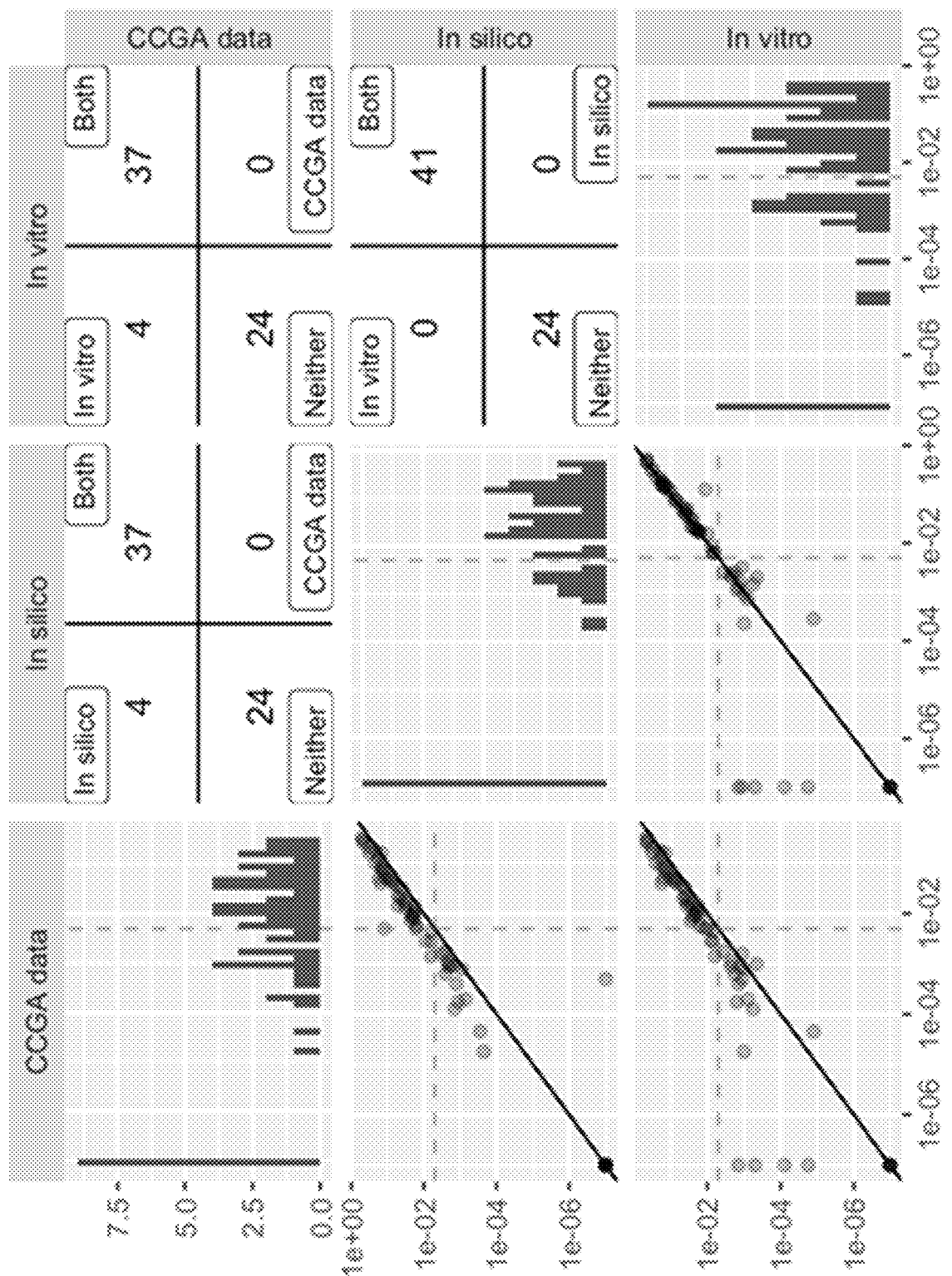
FIG. 15 illustrates comparison of tumor fraction improvement between in vitro and in silico size-selection, relative to unfiltered sequence reads ("CCGA data"). Briefly, the lower panels show pairwise scatterplots of estimated tumor fraction for each combination of sequence reads, with the estimated 0.5% level of detection for whole genome sequencing represented as a dashed line. The diagonal panels show a histogram of the estimated tumor fraction in each sample, with the estimated 0.5% level of detection for whole genome sequencing represented as a dashed line. The upper panel provides counts of the number of samples, using either or both combinations of sequence reads, with a tumor fraction above the estimated 0.5% level of detection for whole genome sequencing, as described in Example 10.

FIG. 15 shows a comparison of this improvement between in vitro and in silico size-selection, relative to unfiltered sequence reads ("CCGA data"). Briefly, the lower panels show pairwise scatterplots of estimated tumor fraction for each combination of sequence reads, with the estimated 0.5% level of detection for whole genome sequencing represented as a dashed line. The diagonal panels show a histogram of the estimated tumor fraction in each sample, with the estimated 0.5% level of detection for whole genome sequencing represented as a dashed line. The upper panel provides counts of the number of samples, using either or both combinations of sequence reads, with a tumor fraction above the estimated 0.5% level of detection for whole genome sequencing. As can be seen, in vitro and in silico size-selection increased the tumor fraction of four samples above the estimated level of detection for whole genome sequencing.

Figure 16:
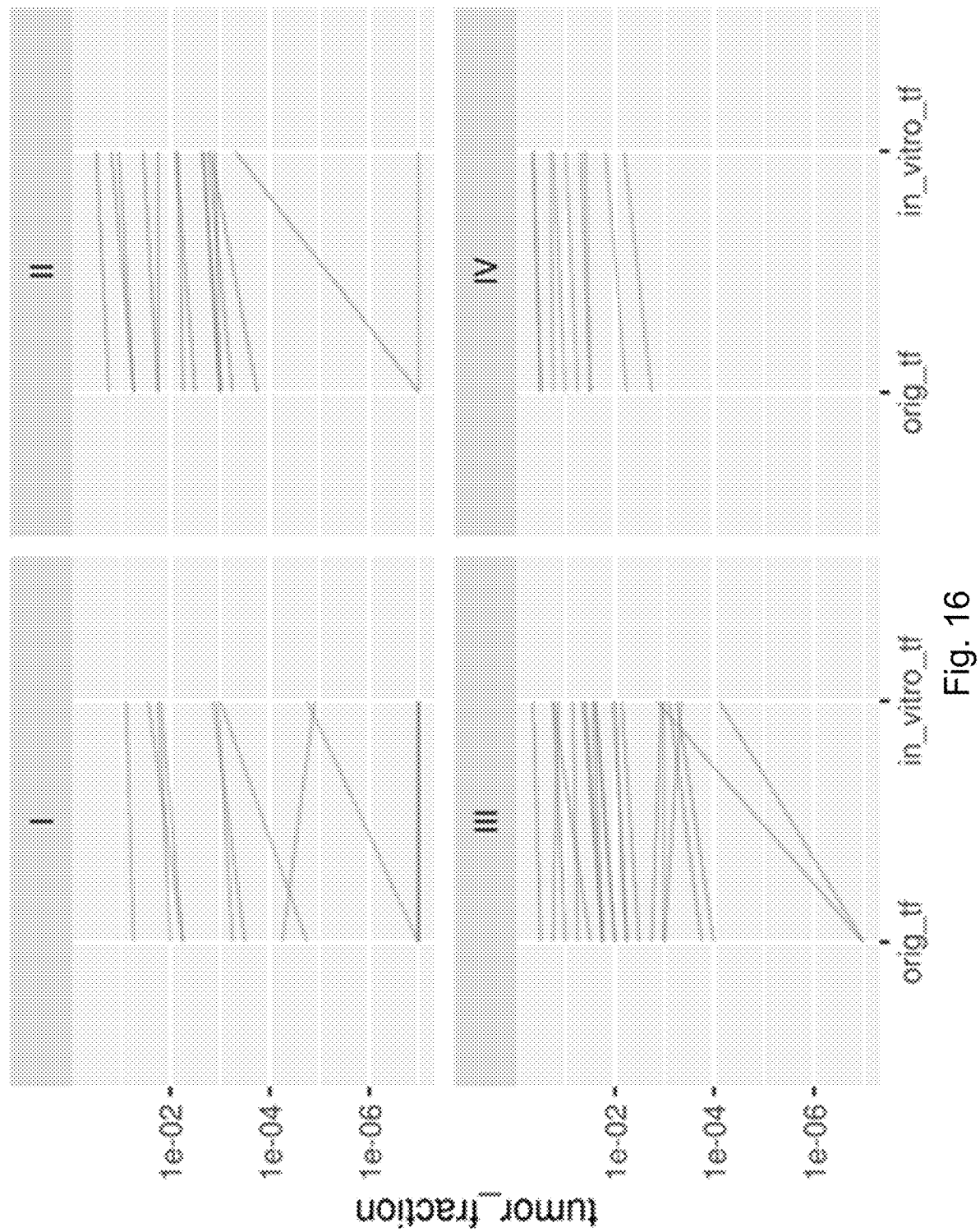
FIG. 16 illustrates the improvement in tumor fraction for the 65 cancer samples, following in vitro size selection, grouped by the stage of cancer (orig_tf is the estimated tumor fraction observed in sequencing reactions of the full cfDNA sample; in_vitro_tf is the estimated tumor fraction observed in sequencing reactions following in vitro size selection), as described in Example 10.
Figure 17:
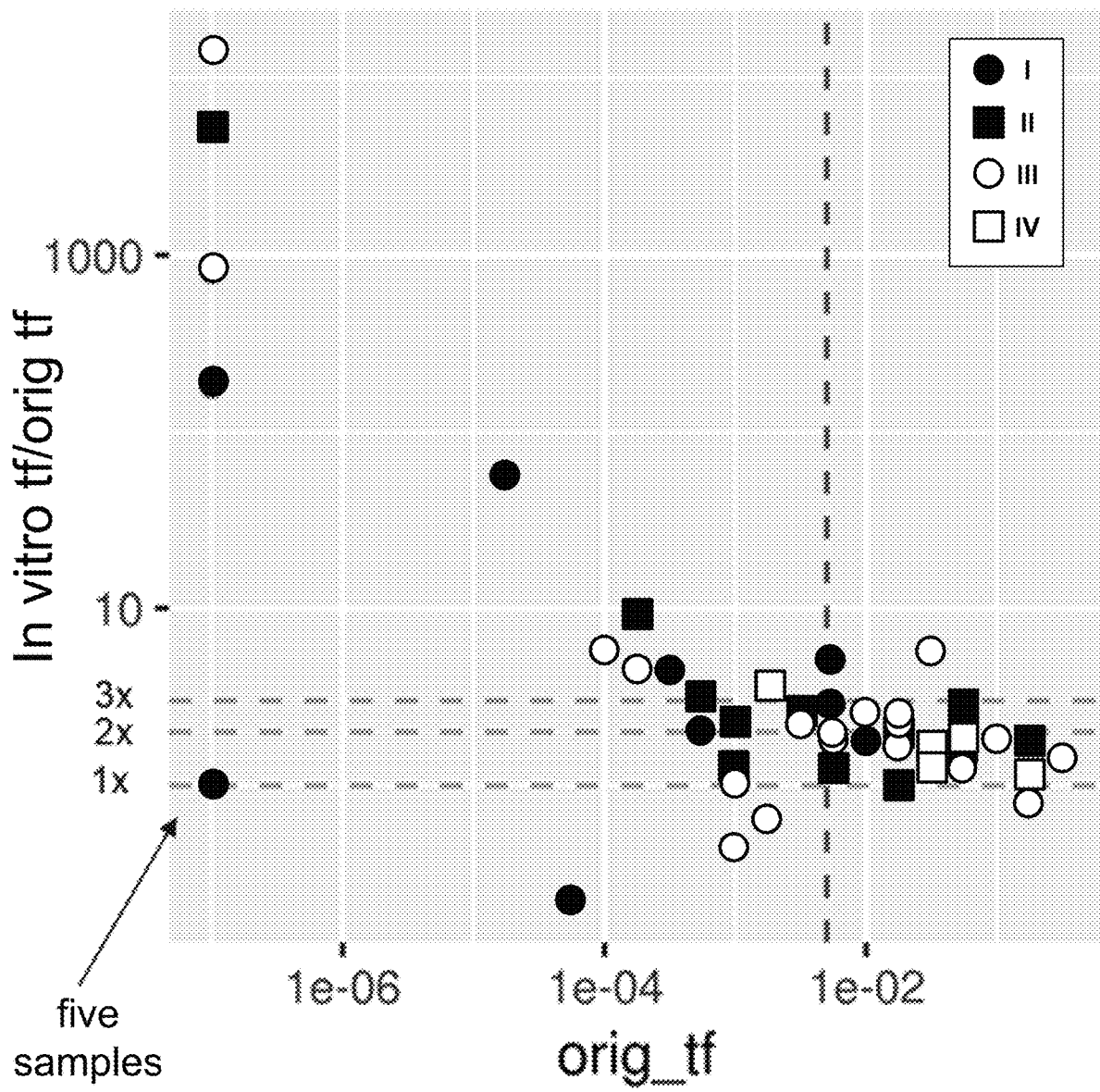
FIG. 17 illustrates the improvement in tumor fraction for the 65 cancer samples, following in vitro size selection, plotted as a function of the original tumor fraction of the sample, as described in Example 10.

FIG. 16 shows the improvement in tumor fraction for the 65 cancer samples, following in vitro size selection, grouped by the stage of cancer (orig_tf is the estimated tumor fraction observed in sequencing reactions of the full cfDNA sample; in_vitro_tf is the estimated tumor fraction observed in sequencing reactions following in vitro size selection). FIG. 17 plots the fold improvement in tumor fraction following in vitro size selection as a function of the original tumor fraction of the sample, grouped by cancer stage. Overall, the tumor fraction improvement is about two-fold across all samples. Tables 4 and 5, below, show the fold improvement in samples grouped by original tumor fraction and cancer stage, respectively.

TABLE 4

Median improvement in tumor fraction following in vitro size selection grouped by the original tumor fraction of the sample.

| Original TF | Median fold improvement |
|---|---|
| <=0.005 | 2.24 |
| <=0.01 | 2.38 |
| <=0.05 | 2.00 |
| <=0.1 | 1.78 |
| <=0.2 | 1.45 |
| <=0.5 | 1.41 |

TABLE 5

Median improvement in tumor fraction following in vitro size selection grouped by cancer stage.

| Stage | Median fold improvement |
|---|---|
| I | 1.89 |
| II | 2.12 |
| III | 2.24 |
| IV | 1.58 |
| NI | 2.24 |

Figure 24A:
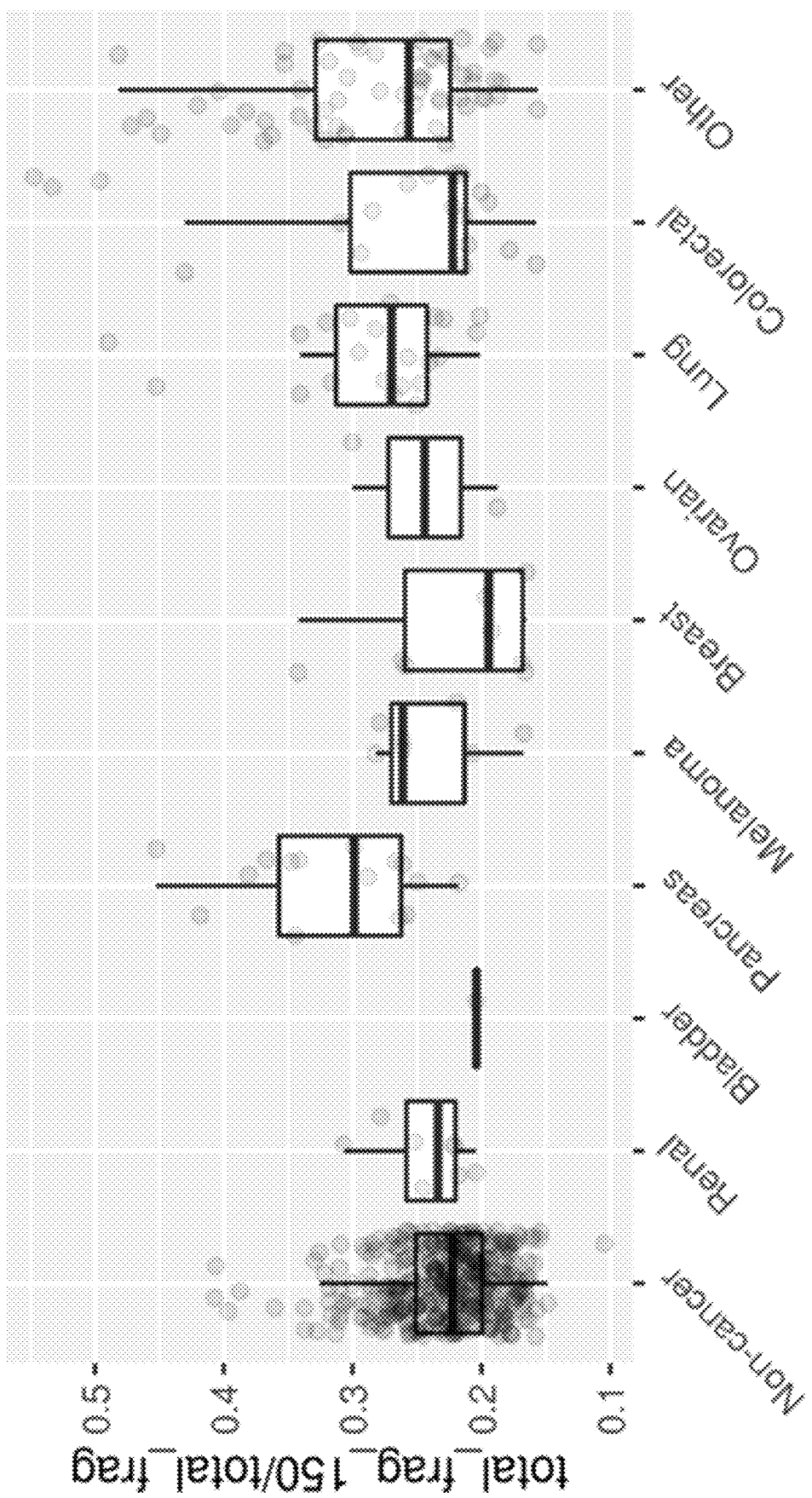
FIGS. 24A and 24B illustrate analyses of the proportion of cfDNA fragments that are smaller than 150 nucleotides in cfDNA samples from subjects with late stage (FIG. 24A) or any stage (FIG. 24B) cancer.
Figure 24B:
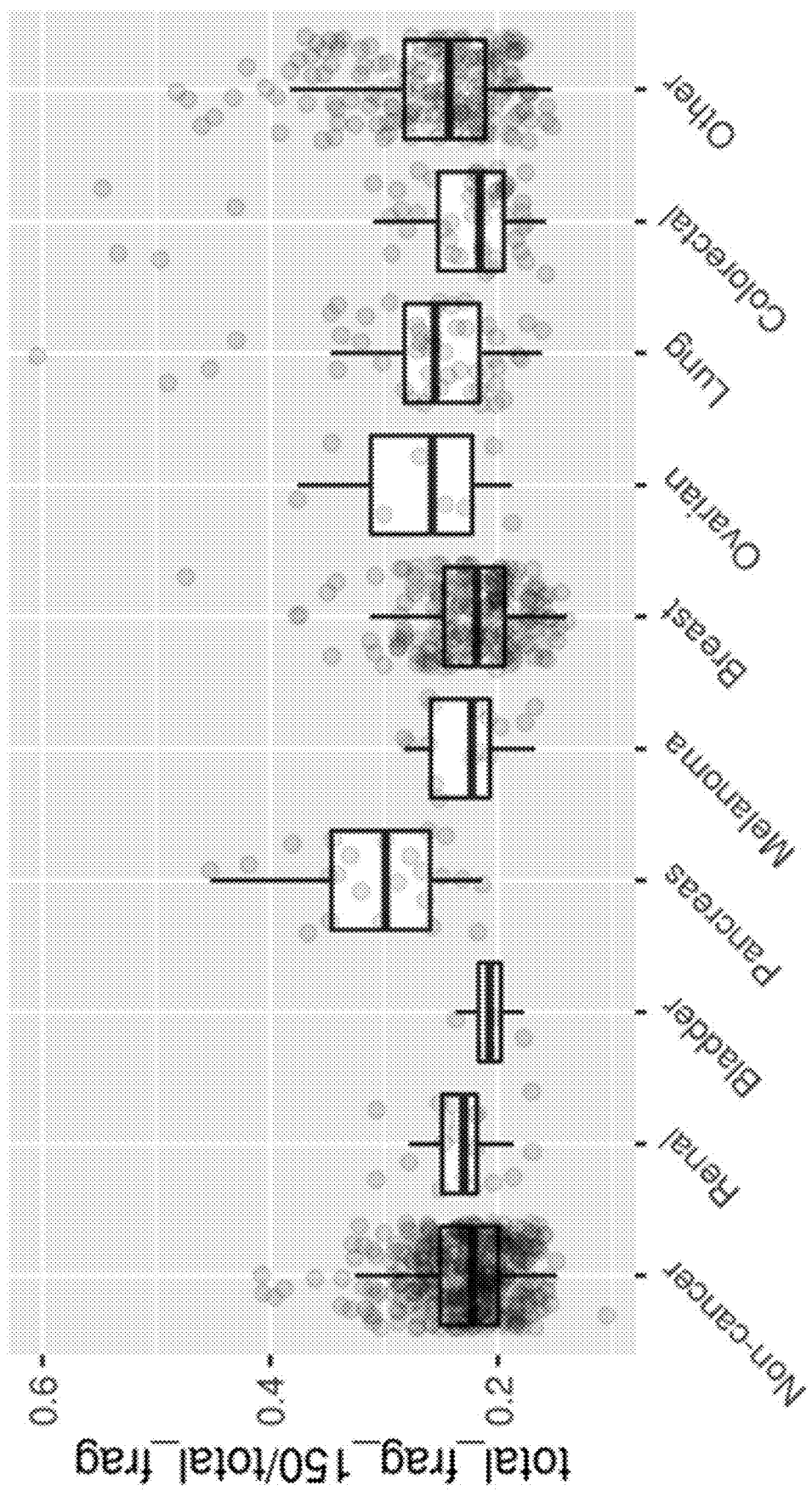

Surprisingly, as shown by this data, size-selection of cfDNA resulted in an enrichment in the fraction of cancer-derived cfDNA is all cancer types. These include cancer types, such as renal cancer, bladder cancer, and pancreatic cancer, for which Mouliere et al., Sci Transl Med., 10(466) (2018), concluded that size-selection would not enrich for tumor-derived cfDNA fragments. Contrary to Mouliere, it was found that cfDNA samples from all cancers had appreciable fractions of smaller cfDNA fragments. For example, FIGS. 24A and 24B illustrate analyses of the proportion of cfDNA fragments that are smaller than 150 nucleotides in cfDNA samples from subjects with late stage (FIG. 24A) or any stage (FIG. 24B) cancer. In fact, as shown in FIG. 24, samples from subjects with pancreatic cancer had the highest proportion of smaller cfDNA fragments.

Figure 18:
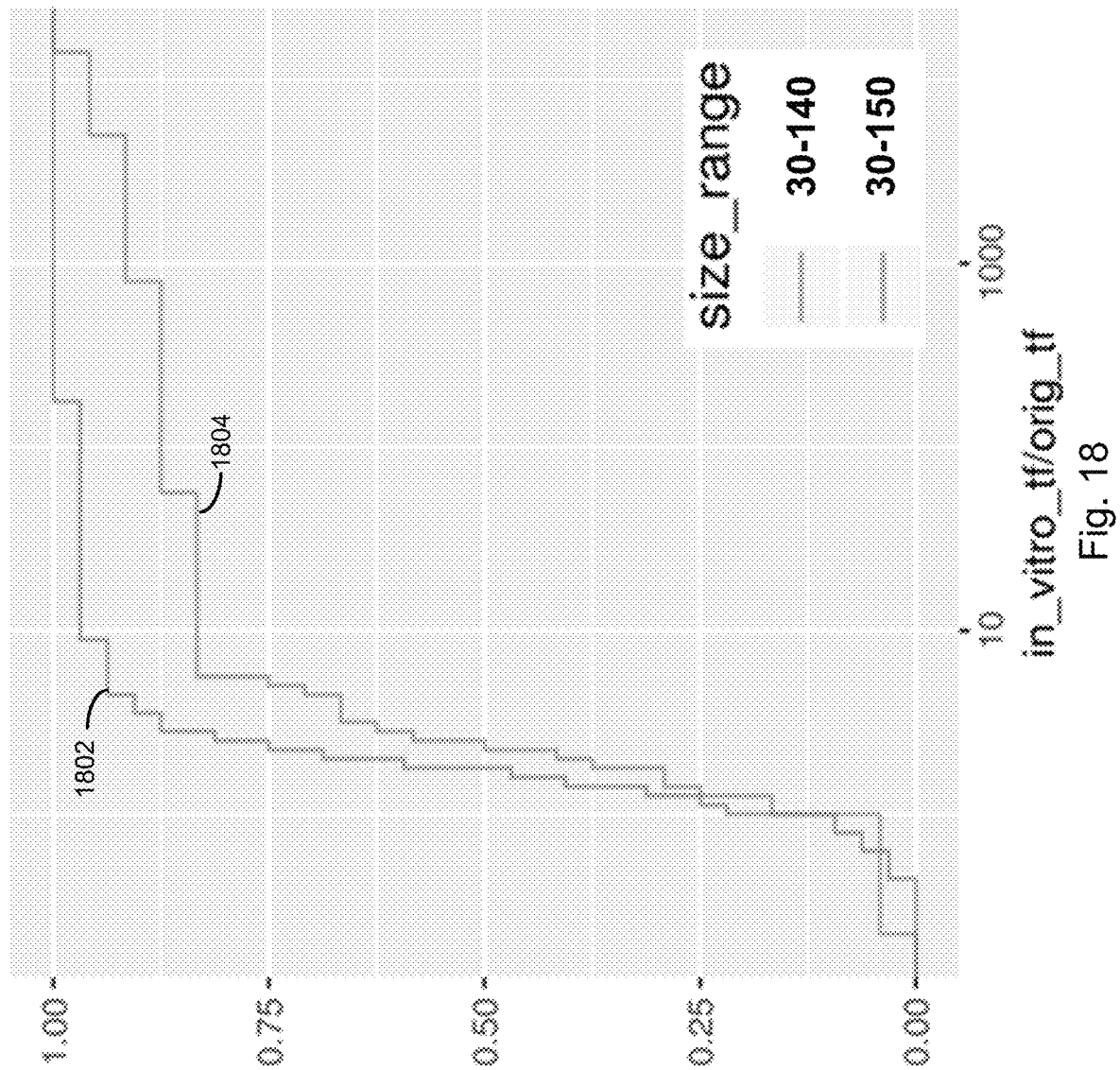
FIG. 18 illustrates cumulative distributions of fold-tumor fraction enrichment following in vitro size selection to either 30-140 nucleotides (1804) or 30-150 nucleotides (1802), as described in Example 10.
Figure 19:
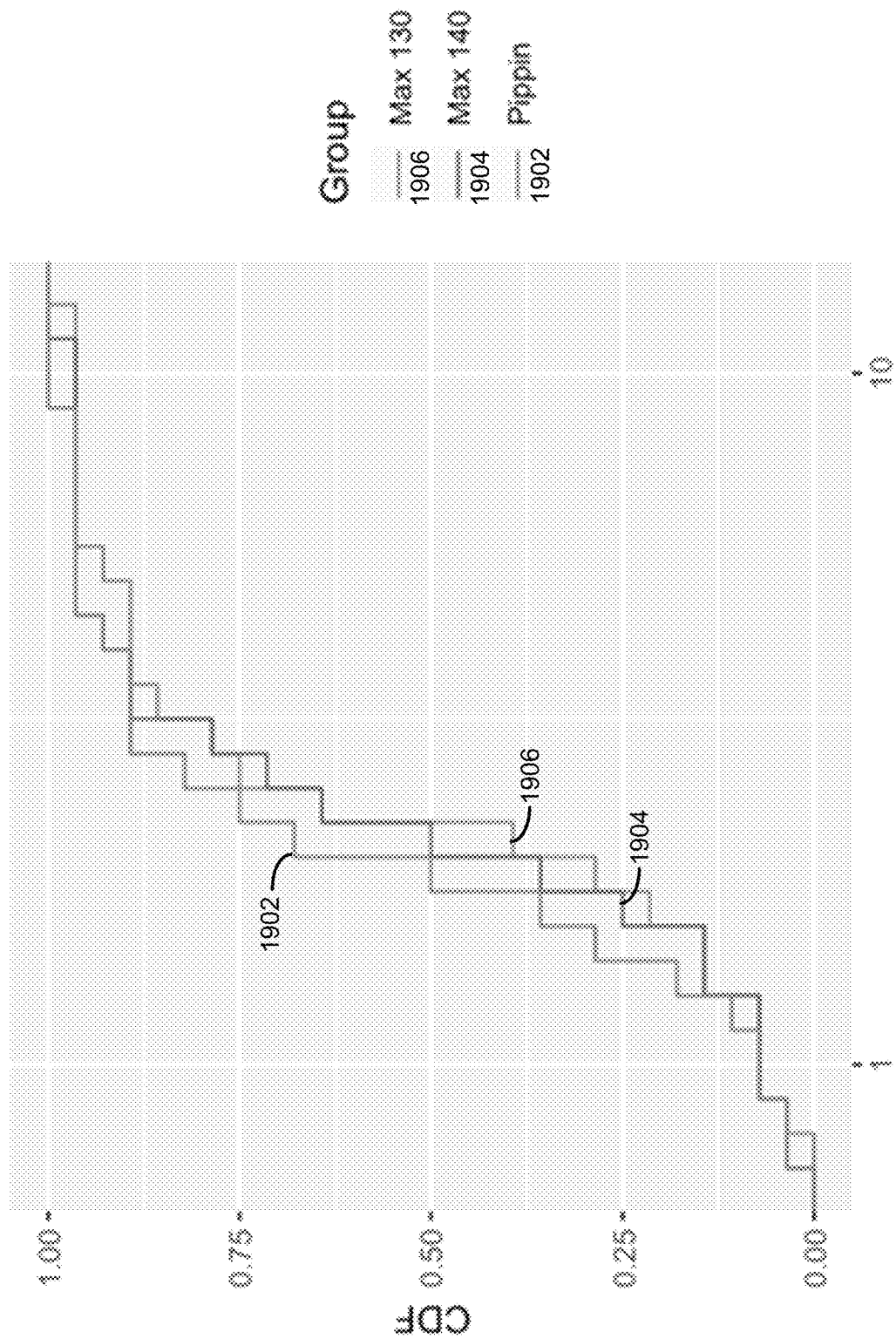
FIG. 19 illustrates cumulative distributions of fold-tumor fraction enrichment following in vitro size selection to 30-150 nucleotides (1902), followed by in silico filtration to maximum lengths of 140 (1904) or 130 (1906) nucleotides, as described in Example 10.

Cumulative distributions of fold-tumor fraction enrichment following in vitro size selection to either 30-140 nucleotides (1804) or 30-150 nucleotides (1802) are plotted in FIG. 18. As can be seen, size selection to between 30-140 nucleotides provides greater fold-improvement in tumor fraction than does size selection to between 30-150 nucleotides. This suggests that size selection of increasingly shorter fragments should further enrich tumor fraction.

Figure 20:
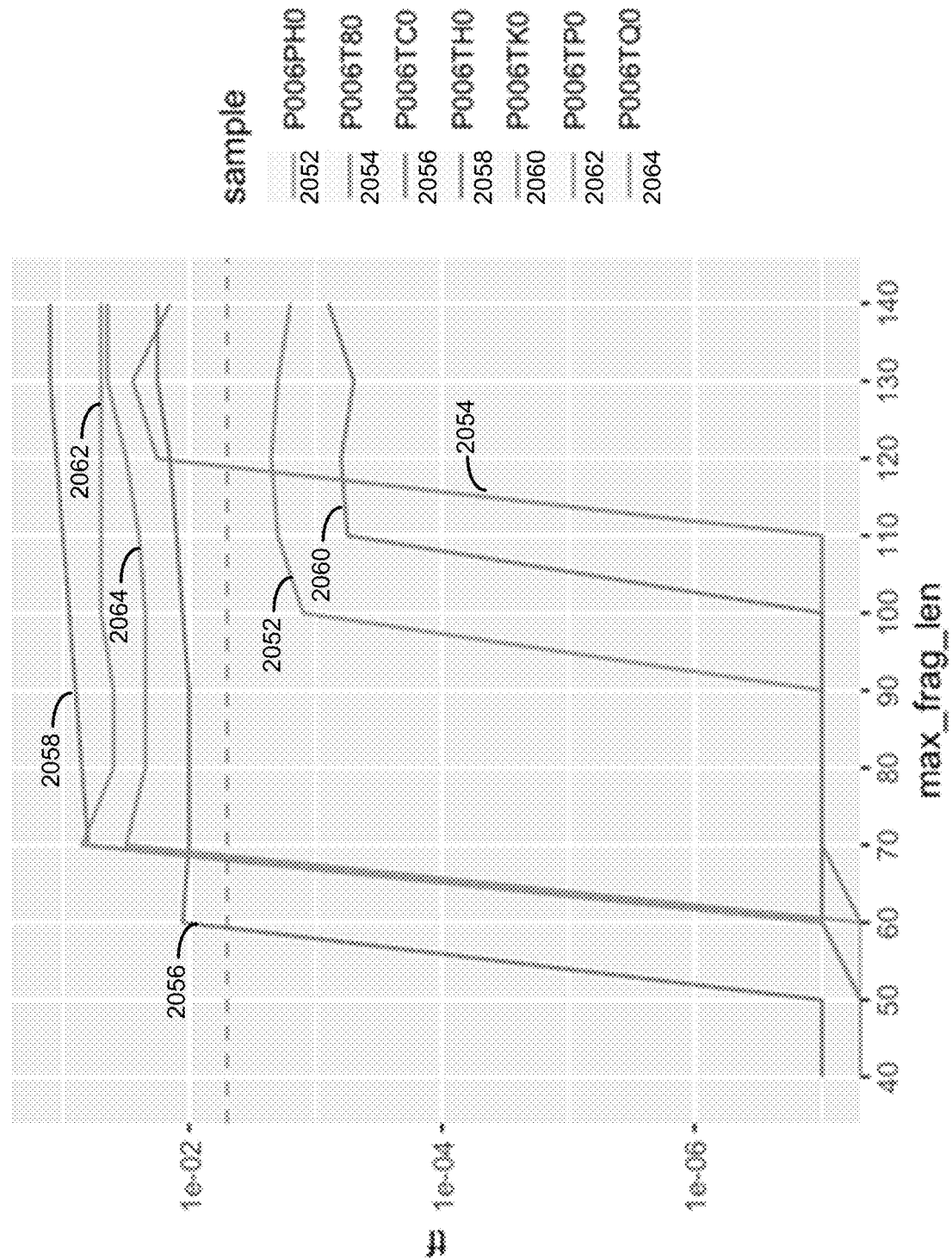
FIG. 20 illustrates the tumor fraction of sequence reads generated following in vitro size selection to 30-150 nucleotides and in silico size selection to increasingly smaller fragments, as described in Example 10.

To test this hypothesis, sequence reads from samples following in vitro size selection between a range of 30-150 nucleotides were further filtered in silico to remove sequence reads from cfDNA fragments larger than 140 nucleotides and 130 nucleotides. As shown by the cumulative distributions of the estimated tumor fraction in these data sets, in silico selection to a maximum length of 140 nucleotides (1904) further improved tumor-fraction enrichment, but in silico selection to a maximum length of 130 nucleotides (1906) did not further enrich tumor fraction, relative to the tumor fraction of the in vitro only size selected data set (1902). Further analysis of the effect of in silico size selection to increasingly smaller cfDNA fragments of sequence reads generated for individual samples after in vitro size selection between a range of 30-150 nucleotides did not show further enrichment of tumor fraction below a maximum of 140 nucleotides (FIG. 20).

Figure 21:
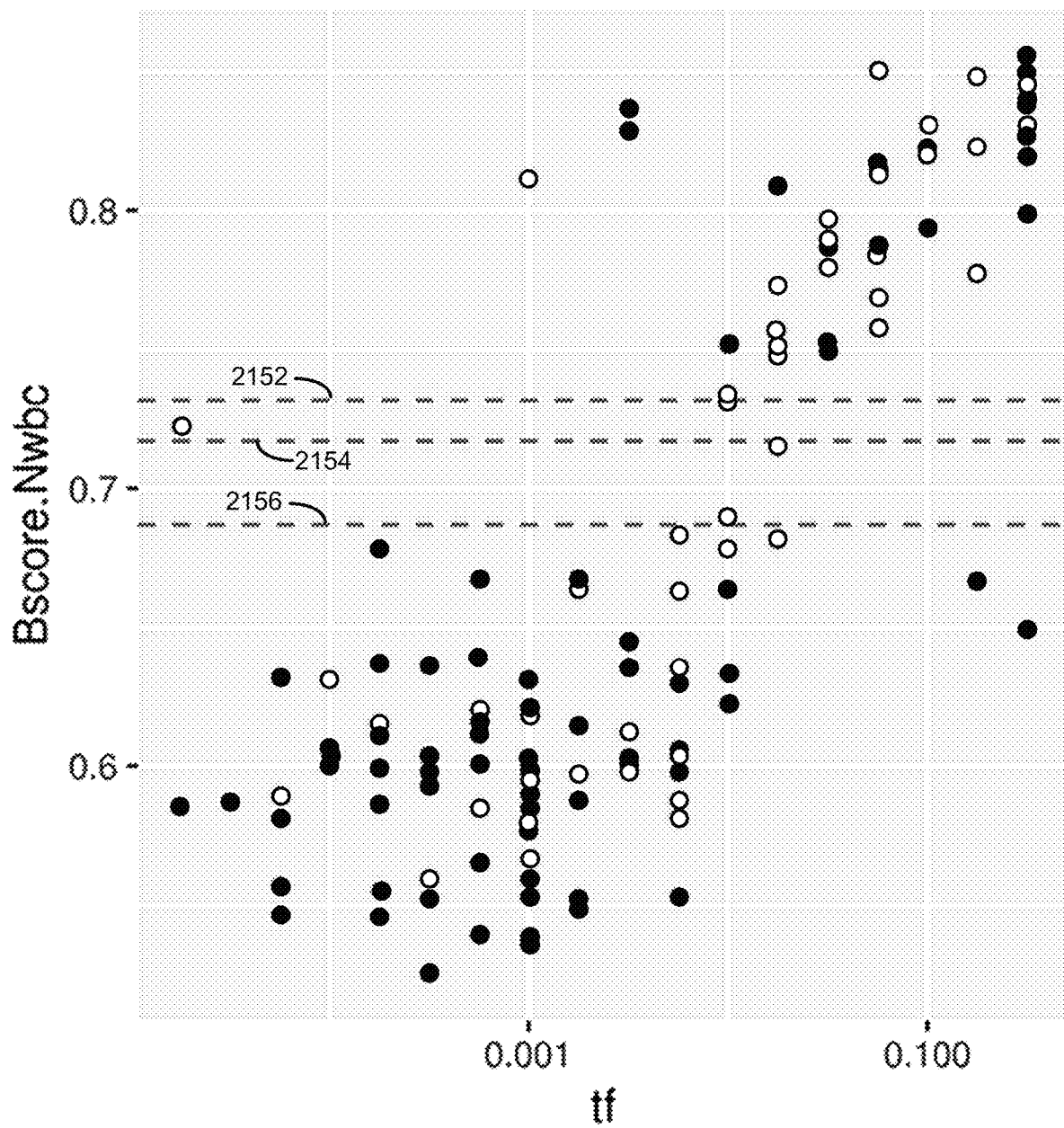
FIG. 21 illustrates classification scores generated using sequence reads from full cfDNA samples and in vitro size-selected cfDNA samples, plotted as a function of the original tumor fraction of the sample, as described in Example 11.

Example 11—Classification Sensitivity Improvement Following In Vitro Size-Selection The sequence read data sets generated on the full cfDNA samples and on the cfDNA samples following in vitro size selection from all 65 cancer samples were input into the cancer classifier trained against copy number variation across a plurality of predetermined genomic bins, each representing a predefined portion of the human genome, as described above and with reference to U.S. Provisional Patent Application Ser. No. 62/642,461, to generate a 'B-score' for each data set. The resulting classification scores (cancer=closed circles; non-cancer=open circles) were then plotted against the original tumor fraction of the sample, as shown in FIG. 21. Specificities of 95% (2156), 98% (2154), and 99% (2152) were determined based on the classification scores and the tumor fraction of samples at those classification scores were determined to be LOD levels. The sensitivities of the classifications using the full data sets or the in vitro size-selected data set were then estimated at each specificity based on the determined LOD levels. As reported in Table 6, in vitro size selection of the cfDNA fragments improved the sensitivity of the assay by about 20-30% at all three specificities.

TABLE 6

Classification sensitivity following in vitro size selection.

| Specificity | Median TF in $(p - \delta, p + \delta)$ | Original sensitivity | In vitro sensitivity | Ratio |
|---|---|---|---|---|
| 95% | 0.008 | 0.46 | 0.56 | 1.22 |
| 98% | 0.010 | 0.46 | 0.54 | 1.18 |
| 99% | 0.014 | 0.39 | 0.51 | 1.30 |

Example 12—Changes in Detectable Cancer Signals

Figure 23A:
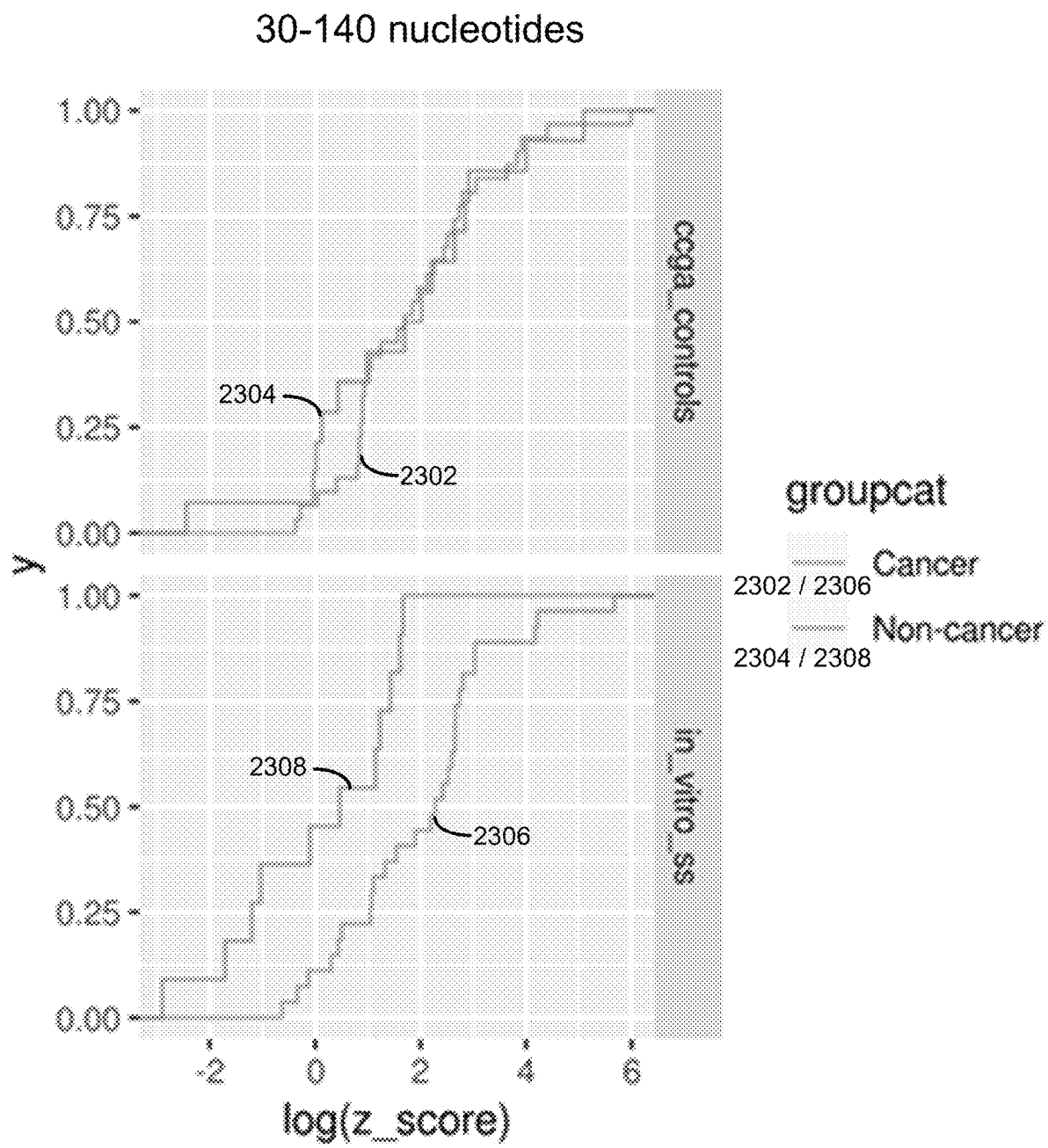
FIGS. 23A and 23B illustrate cumulative distributions of MAPD Z-scores for cancer and non-cancer samples from the non-size-selected samples (top panel) and size-selected samples (bottom panel), both for size selection between 30-150 nucleotides (FIG. 23A) and 30-140 nucleotides (FIG. 23B).
Figure 23B:
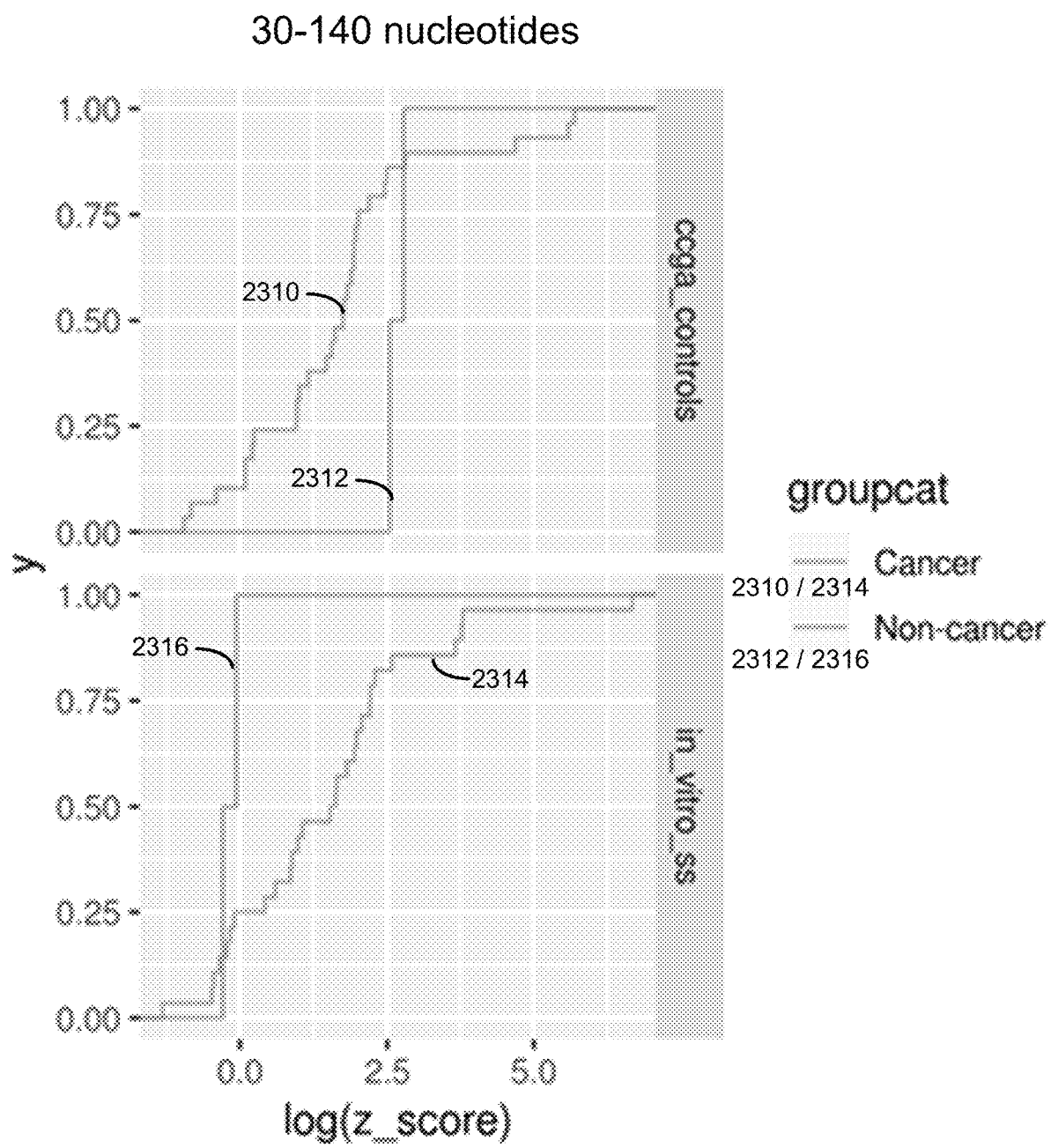

It was next asked whether other changes in detectable cancer signals could be observed after in vitro size selection. Briefly, the sequence reads generated from the full cfDNA samples and cfDNA samples following in vitro size selection (both 30-140 and 30-150 nucleotides) for the 65 cancer samples and 29 non-cancer samples, as described in the Examples above, were re-normalized against sequencing data from non-cancer samples. Median absolute pairwise difference (MAPD) for adjacent genomic locations were then calculated for each data set and the MAPD values determined for the size-selected data sets were plotted as a function of the MAPD for the matching non-size-selected data set. As shown in FIG. 22, MAPD increased in the size-selected data sets. The Z-score of the MAPD values were then used as a proxy for a classifier to distinguish between cancerous samples and non-cancerous samples. As shown by cumulative distribution plots of MAPD Z-score for cancer and non-cancer samples from the non-size-selected samples (top panel) and size-selected samples (bottom panel), both for size selection between 30-150 nucleotides (FIG. 23A) and 30-140 nucleotides (FIG. 23B), there is more difference between cancer samples (2302, 2306, 2310, and 2314) and non-cancer samples (2304, 2308, 2312, and 1216) after size-selection. This suggests that classification models built against size-selected data would provide higher sensitivity, as suggested in several Examples above.

Example 13—Enrichment of Tumor Fraction Following In Silico and In Vitro Size-Selection Detection of somatic copy number aberrations in individuals with cancer via whole-genome sequencing (WGS) of cfDNA is challenging at low tumor fractions. Given that tumor-derived cfDNA fragments are, on average, shorter than those from healthy tissues, e.g., as shown in FIG. 5, exploratory analysis was performed to evaluate the effect of size selection on cancer detection sensitivity. As described above, in silico and in vitro size selection of cfDNA samples from the CCGA study were used for this purpose.

For the in silico experiments, a clinically evaluable CCGA training set of cfDNA samples (n=1420: 560 non-cancer [NC], 860 cancer [C] stages 0-IV/NI) and a hold-out set of individuals under the age of 30 without a cancer diagnosis (referred to as the "calibration set", n=169) (Table 7) were used. All of these samples passed standard assay quality control. The set included only the solid cancer samples and cancers with single or multiple primaries. Two samples (1 C, 1 NC) were removed due to a sample swap. WGS libraries were produced for all samples, achieving 36× depth.

For every sample, including the calibration set, fragments between 90-150 bp were used for analysis, reducing sequencing depth for size-selected samples to 6.91±2.64× depth. For every in silico size-selected sample, a depth-matched control was generated that included all fragment lengths. The calibration set was then used to re-normalize the training set samples to remove assay effects for both size-selected and down-sampled data.

TABLE 7

Sample Counts for in silico and in vitro Experiments by Stage and Cancer Type

| | In Silico Classifier Count | In Silico Count With Tissue | In Vitro Count |
|---|---|---|---|
| Stage | | | |
| I | 283 | 195 | 13 |
| II | 235 | 178 | 15 |
| III | 156 | 99 | 21 |
| IV | 157 | 75 | 12 |
| Others | 29 | 39 | 4 |
| Cancer Type | | | |
| Breast | 345 | 283 | 18 |
| Colorectal | 49 | 33 | 13 |
| Lung | 121 | 47 | 6 |
| Gastric | 12 | 6 | 2 |
| Pancreas | 26 | 8 | 3 |
| Other* | 307 | 209 | 23 |

*Anorectal; renal; cervical; esophageal; head/neck; hepatobiliary; lymphoma; melanoma; ovarian; prostate; thyroid; uterine; unknown primary.

For the in vitro experiments, tumor fraction changes were evaluated following physical size-selection using Pippin Prep (Sage Science, Inc, Beverly, MA). Size selection was performed after library preparation and amplification, providing several advantages over pre-amplification size-selection workflows. For example, more material is available for size selection after amplification, which reduces loss of rare tumor-derived fragments. Further, adapter ligation increases fragment size by 150 bp, which is more separable by conventional size-selection methods, including Pippin Prep. Finally, size selection can be performed on pooled libraries after the incorporation of sample indices, making the process highly scalable.

The in vitro analyses used a subset of the CCGA test set samples (n=93: 28 non-cancer, 65 cancer stages I-IV/NI), including C cases sampled across a range of tumor fractions (Table 7). NC samples were age matched to C samples.

For each sample, 1 μg of the WGS library preparation was run on a 3% agarose gel cassette. The eluted library was diluted, pooled, and sequenced without further cleanup. The mapped fragment length of size-selected libraries showed a decrease in fragment size compared to libraries sequenced prior to size selection, e.g., as shown in FIG. 13. When sequencing, the number of fragments was matched to that of the original CCGA samples, which resulted in a lower depth of 23±4.45× due to an enrichment of shorter fragments.

Figure 25A:
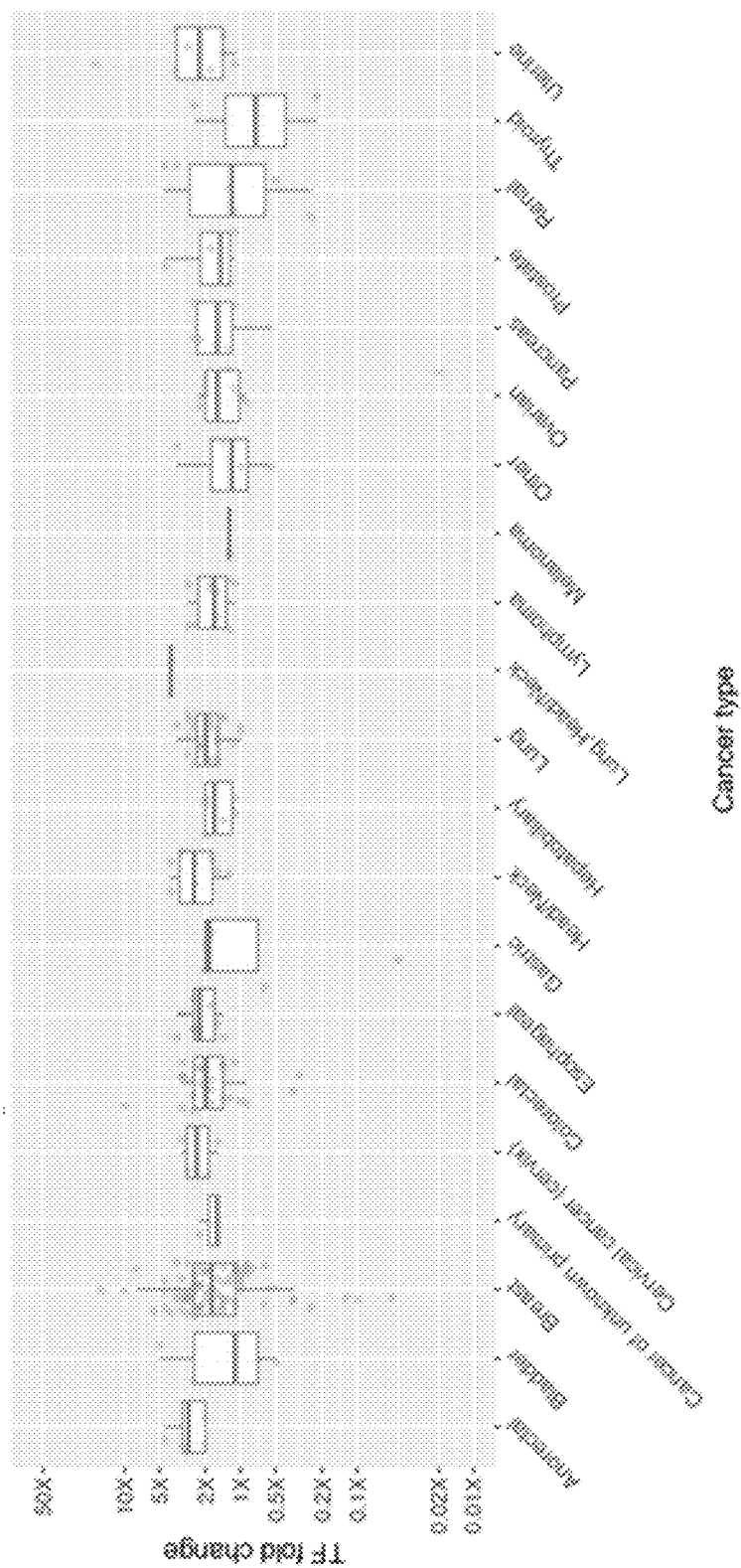
FIGS. 25A and 25B illustrate the fold-change in tumor fraction following in silico (FIG. 25A) and in vitro (FIG. 25B) size selection of cfDNA, across various tumor types, as described in Example 13.
Figure 25B:
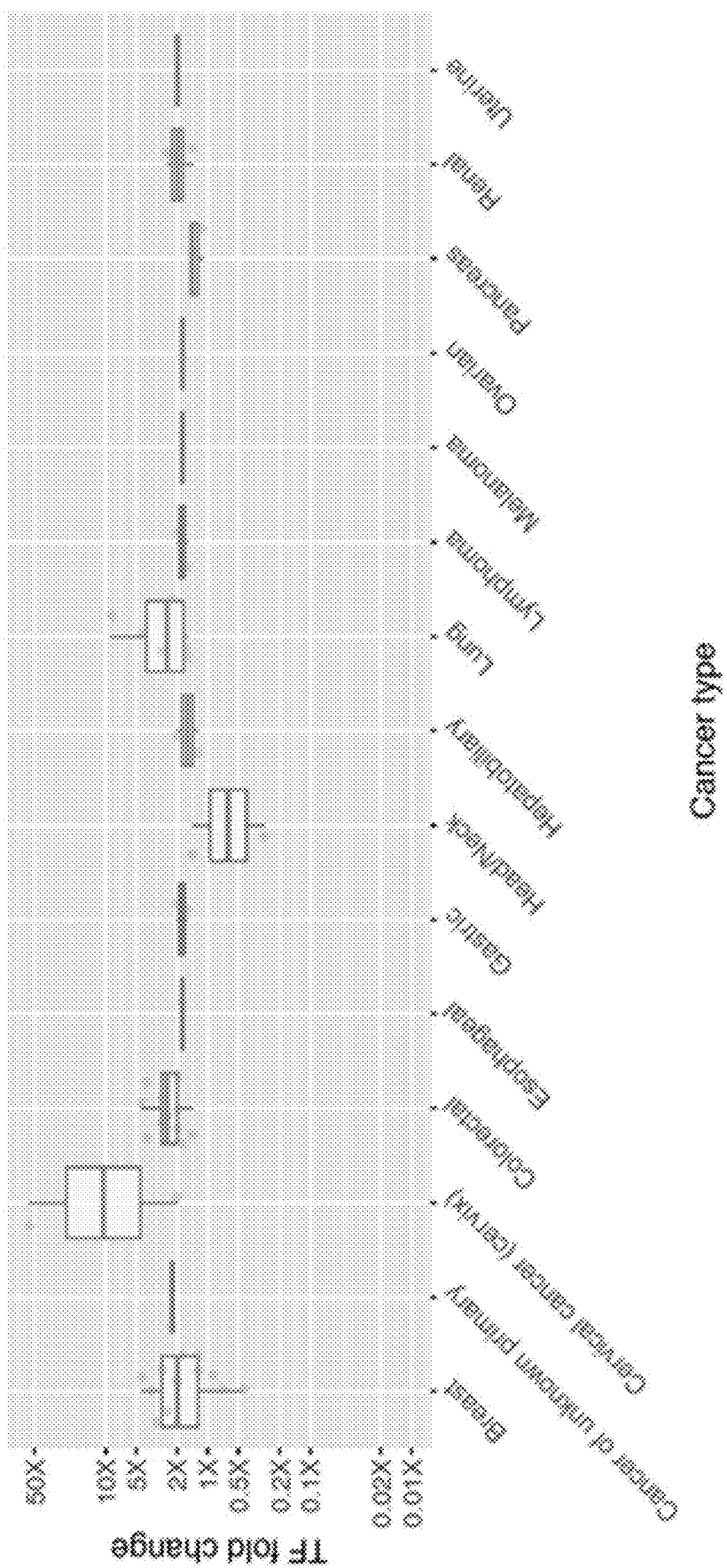
Figure 26A:
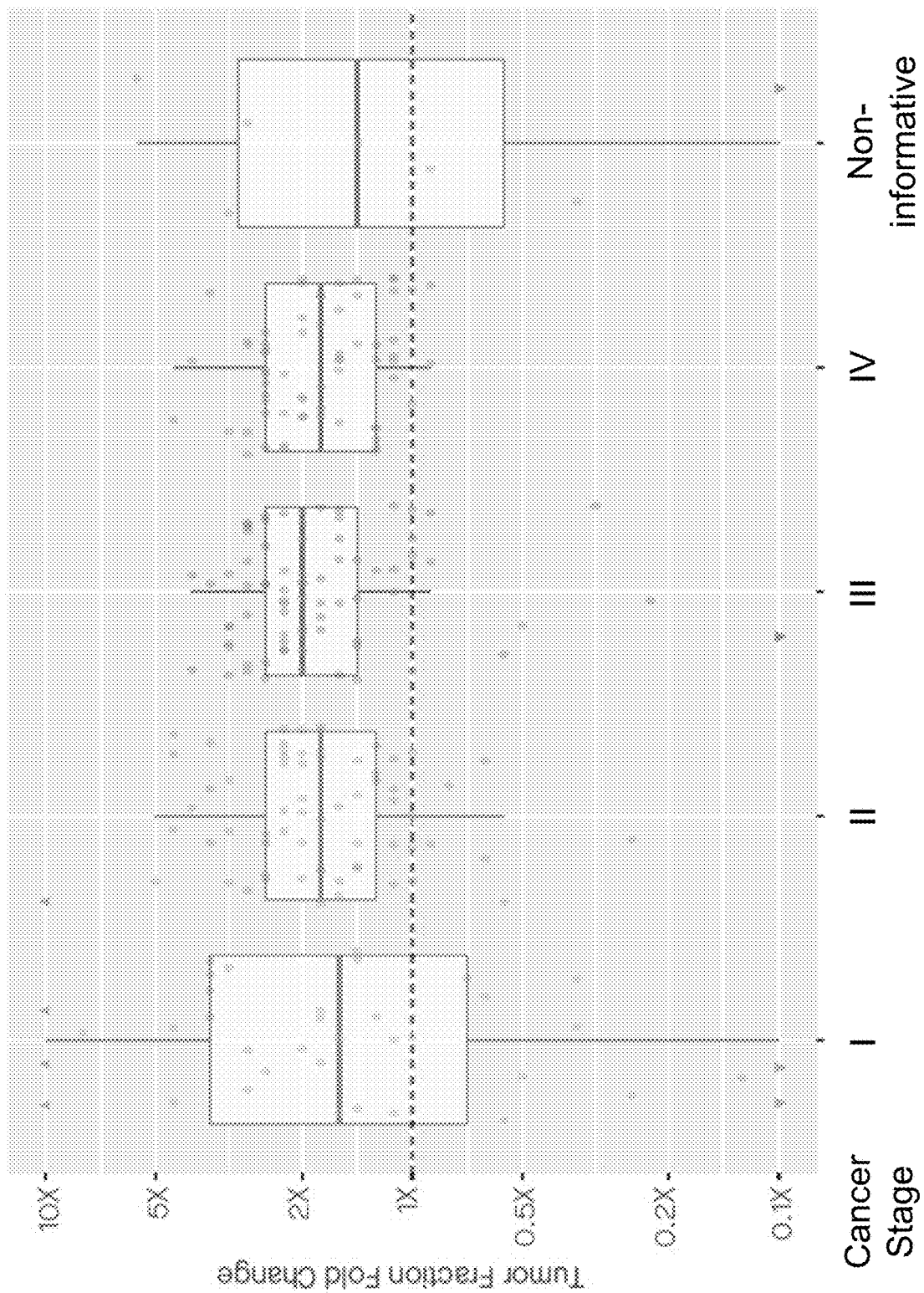
FIGS. 26A and 26B illustrate the fold-change in tumor fraction following in silico (FIG. 26A) and in vitro (FIG. 26B) size selection of cfDNA, across various tumor types, as described in Example 13.
Figure 26B:
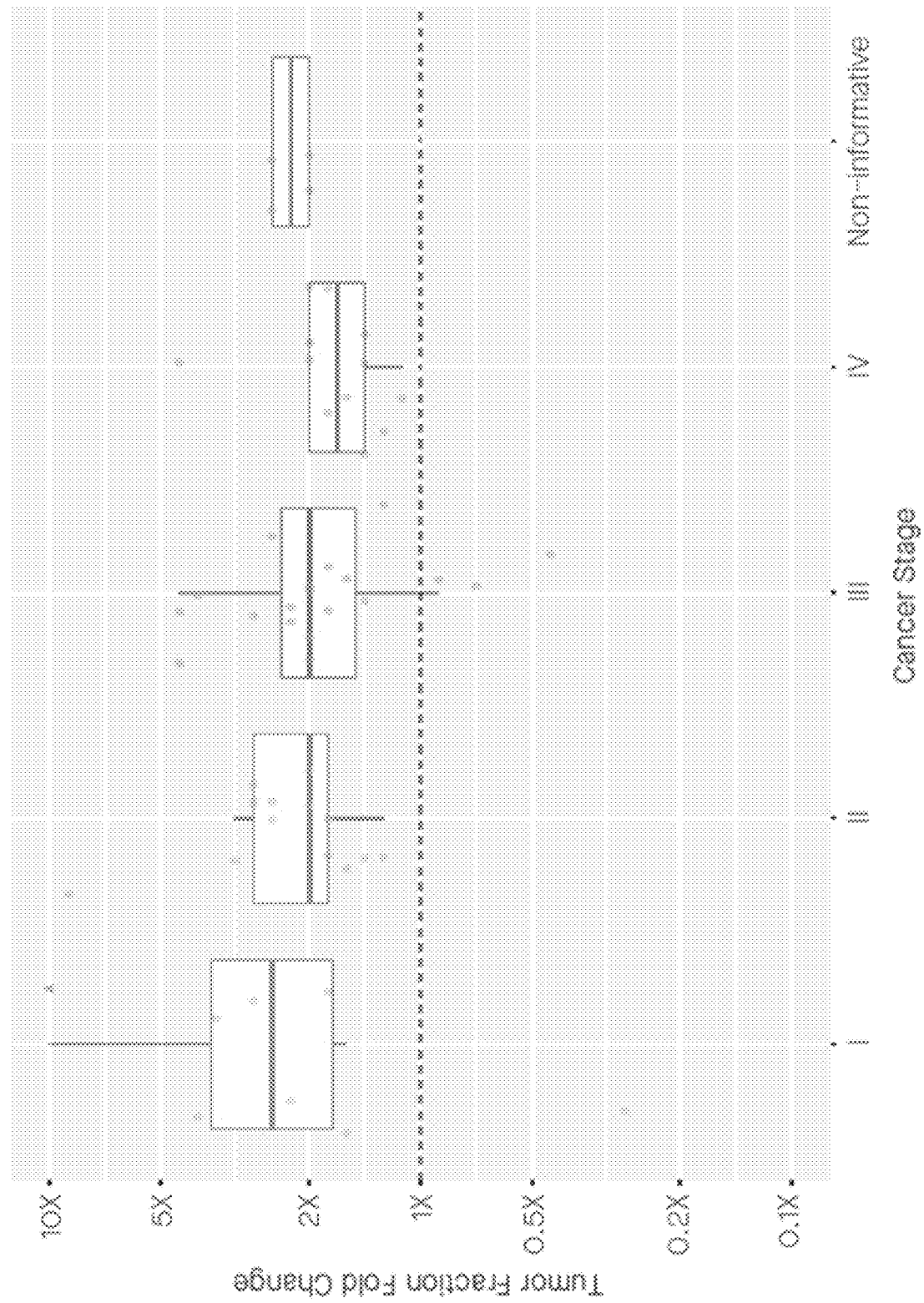

The in silico and in vitro analyses showed median 2.00±0.58-fold and 2.00±0.52-fold increases in overall tumor fraction, respectively (compared to original CCGA non-size-selected samples). Tumor fraction fold change was consistent across tumor types (e.g., in silico: 1.78±0.73 breast, 2.00±0.58 CRC, 2.00±0.41 lung, as shown in FIG. 25A; in vitro: 2.00±0.82 breast, 2.51±0.52 CRC, 2.53±0.94 lung, as shown in FIG. 25B). These results are in contrast with Mouliere et al., Sci Transl Med., 10(466) (2018), which defined a group of "low ctDNA" cancer types that may not benefit from size selection. The tumor fraction increase was also consistent across the stage of cancer. For example, the in silico experiments showed a median tumor fraction increase of 2.00±0.74 fold for stage I-III cancers and 1.78±0.52 fold for stage IV cancers, as shown in FIG. 26A. Similarly, the in vitro experiments showed a median tumor fraction increase of 2.00±0.55 fold for stage I-III cancers and 1.68±0.29 fold for stage IV cancers, as shown in FIG. 26B.

Figure 27:
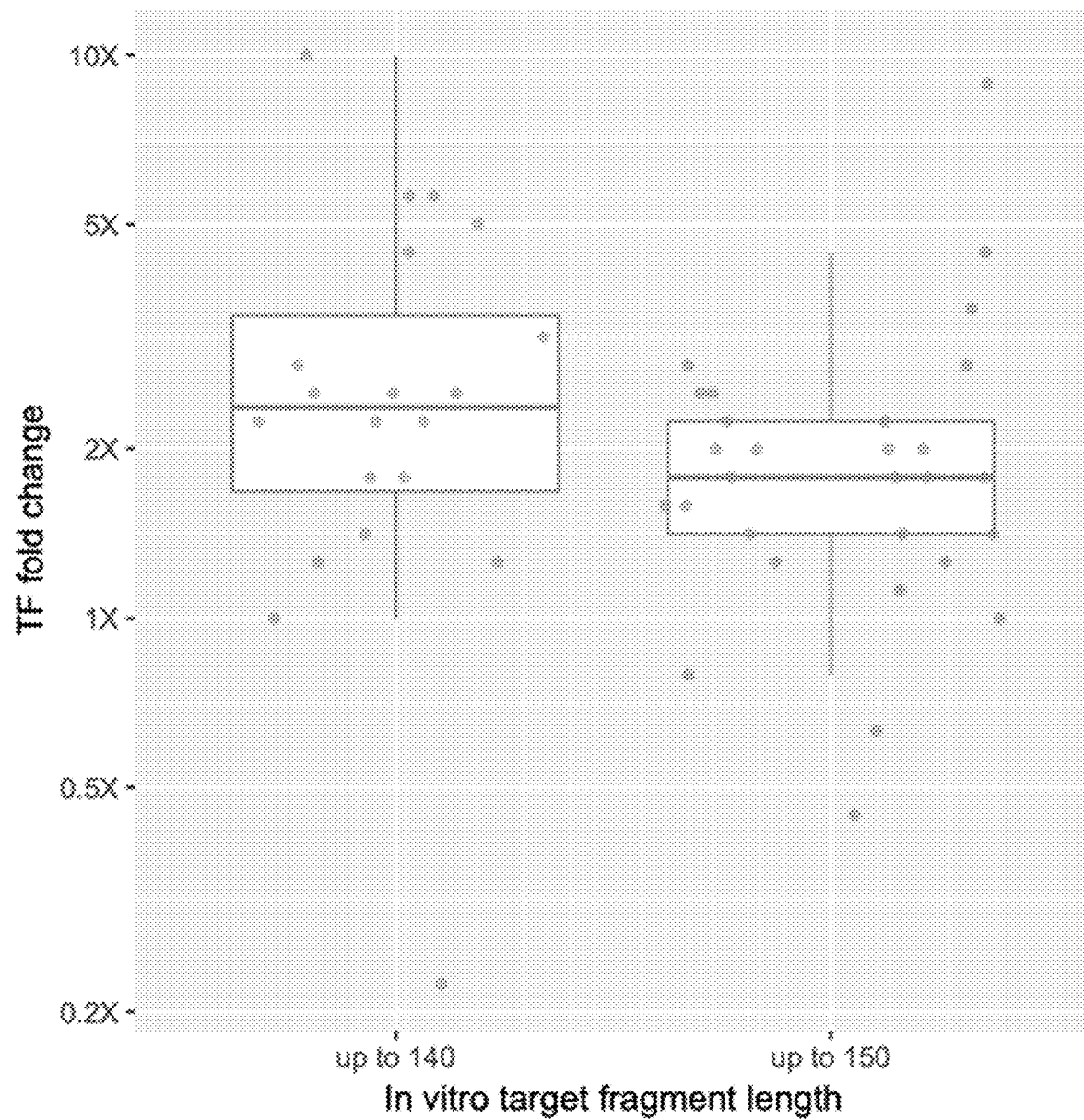
FIG. 27 illustrates the fold-change in tumor fraction following in vitro size selection to no more than 140 bp or 150 bp, as described in Example 13.

To test whether size-selecting to shorter fragment lengths resulted in further increases in tumor fraction, tumor fraction was measured on in vitro size-selected samples that were further in silico size-selected to shorter fragment lengths, starting at 140 bp and incrementing down to a maximum fragment length of 50 bp in intervals of 10 bp. When filtering in vitro samples to retain only shorter fragments, tumor fraction did not significantly change relative to the original estimate, data not shown. When comparing tumor fraction between in vitro samples that were size-selected to 140 bp or 150 bp, samples that were size-selected to 140 bp have higher tumor fraction on average, as shown in FIG. 27.

Significantly, a classifier trained on the in silico size-selected data had increased sensitivity of 37.8% at 98% specificity compared to sensitivity of 32.9% on the full-depth data, and 32.1% on the down-sampled set (p<1e-5).

As is demonstrated by the above examples, in silico and in vitro size selection consistently increased tumor fraction across all tested cancer types and stages, and this increase was maximized by tuning size selection. Classification performance improved significantly relative to both full-depth data and data down-sampled to match depth after size-selection. Given that tumor fraction appeared maximal when size-selecting to lengths up to 140 bp, these data suggest that size selection of even modest amounts targeting cfDNA under 140 bp may enhance cfDNA-based cancer detection in WGS assays.

REFERENCES CITED AND ALTERNATIVE EMBODIMENTS

All references cited herein are incorporated herein by reference in their entirety and for all purposes to the same extent as if each individual publication or patent or patent application was specifically and individually indicated to be incorporated by reference in its entirety for all purposes.

The present invention can be implemented as a computer program product that comprises a computer program mechanism embedded in a non-transitory computer readable storage medium. For instance, the computer program product could contain the program modules shown in any combination of FIG. 1, and/or as described in FIGS. 3 and 4. These program modules can be stored on a CD-ROM, DVD, magnetic disk storage product, USB key, or any other non-transitory computer readable data or program storage product.

Many modifications and variations of this invention can be made without departing from its spirit and scope, as will be apparent to those skilled in the art. The specific embodiments described herein are offered by way of example only. The embodiments were chosen and described in order to best explain the principles of the invention and its practical applications, to thereby enable others skilled in the art to best utilize the invention and various embodiments with various modifications as are suited to the particular use contemplated. The invention is to be limited only by the terms of the appended claims, along with the full scope of equivalents to which such claims are entitled.

What is claimed is:

1. A method of determining a cancer class of a subject, comprising:
   extracting a plurality of cell-free DNA molecules in a biological sample acquired from a subject;
   removing, from the plurality of cell-free DNA molecules, cell-free DNA molecules longer than a first threshold length to obtain a pool of size-selected cell-free DNA molecules, wherein the first threshold length is less than 160 nucleotides;
   sequencing the biological sample based on the pool of size-selected cell-free DNA molecules to obtain a plurality of size-selected sequence reads, wherein the plurality of size-selected sequence reads comprise at least 60,000 sequence reads;
   identifying, from the plurality of size-selected sequence reads, a relative copy number at each respective genomic location in at least fifty genomic locations in the genome of the subject; and
   applying the identified relative copy numbers into a machine learning model trained to determine the cancer class for the subject based on the relative copy number at each respective genomic location, wherein the machine learning model is trained with a training dataset labeled by cancer class.

2. The method of claim 1, wherein the cancer class of the subject comprises whether or not the subject has cancer.

3. The method of claim 1, wherein the cancer class of the subject comprises a stage of a cancer.

4. The method of claim 1, wherein the cancer class of the subject comprises a type of a cancer.

5. The method of claim 1, wherein the cancer class of the subject comprises a prognosis for a cancer.

6. The method of claim 1, wherein the subject has not been diagnosed as having cancer.

7. The method of claim 1, wherein the biological sample is a blood sample.

8. The method of claim 1, wherein the first threshold length is between 140 nucleotides and 150 nucleotides.

9. The method of claim 1, wherein the first threshold length is 140 nucleotides.

10. The method of claim 1, wherein the at least 60,000 sequence reads, prior to removal of the cell-free DNA molecules with sequence reads longer than the first threshold length, include sequence reads having a length falling between a second threshold length and a third threshold length, wherein:

the second threshold length is from 240 nucleotides to 260 nucleotides, and the third threshold length is from 290 nucleotides to 310 nucleotides.

11. The method of claim 1, wherein the plurality of size-selected sequence reads includes more than 5000 sequence reads.

12. The method of claim 1, wherein the machine learning model comprises a multinomial classifier that provides a plurality of likelihoods responsive to the identification of the relative copy number at each respective genomic location, wherein each respective likelihood in the plurality of likelihoods is a likelihood that the subject has a corresponding cancer class in a plurality of cancer classes.

13. The method of claim 1, wherein the genomic locations are selected from a precursor set of genomic locations by a method comprising removing respective genomic locations in the precursor set having a variance that exceeds a threshold variance in relative copy number within a training set of electronic sequence reads.

14. The method of claim 1, wherein the applying the identified relative copy numbers into the machine learning model comprises applying a methylation state at a locus in the genome of the subject to the machine learning model.

15. The method of claim 1, wherein:

the cancer class of the subject is determined with a first degree of confidence, and the first degree of confidence is greater than a second degree of confidence obtainable by application of genetic information consisting of relative copy number at each respective genomic location in the plurality of genomic locations obtained from a second plurality of sequence reads from the biological sample, to the machine learning model, wherein the second plurality of sequence reads encodes (i) cell-free DNA molecules that are shorter than the first threshold length and (ii) cell-free DNA molecules that are longer than the first threshold length.

* * * * *